United States Patent
Park et al.

(10) Patent No.: US 9,290,513 B2
(45) Date of Patent: *Mar. 22, 2016

(54) COMPOUND CONTAINING 5-MEMBERED HETEROCYCLES, ORGANIC ELECTRONIC DEVICE USING SAME, AND TERMINAL COMPRISING THE LATTER

(71) Applicant: DUK SAN NEOLUX CO., LTD., Cheonan-si, Chungcheongnam-do (KR)

(72) Inventors: Junghwan Park, Seoul (KR); Daesung Kim, Yongin-si (KR); Jungcheol Park, Jinhae-si (KR); Yongwook Park, Anyang-si (KR); Hwasoon Jung, Chuncheon-si (KR); Soungyun Mun, Yongin-si (KR); Daehyuk Choi, Suwon-si (KR); Dongha Kim, Seongnam-si (KR); Bumsung Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/791,643

(22) Filed: Jul. 6, 2015

(65) Prior Publication Data

US 2015/0307514 A1 Oct. 29, 2015

Related U.S. Application Data

(63) Continuation-in-part of application No. 13/390,043, filed as application No. PCT/KR2010/005206 on Aug. 9, 2010, now Pat. No. 9,079,920.

(30) Foreign Application Priority Data

Aug. 11, 2009 (KR) .................... 10-2009-0073915

(51) Int. Cl.
| | | |
|---|---|---|
| *C07D 495/14* | (2006.01) |
| *C07D 491/147* | (2006.01) |
| *C07D 487/14* | (2006.01) |
| *H01L 51/00* | (2006.01) |
| *H01L 51/50* | (2006.01) |

(52) U.S. Cl.
CPC ............ *C07D 495/14* (2013.01); *C07D 487/14* (2013.01); *C07D 491/147* (2013.01); *H01L 51/0071* (2013.01); *H01L 51/0072* (2013.01); *H01L 51/006* (2013.01); *H01L 51/0058* (2013.01); *H01L 51/0061* (2013.01); *H01L 51/0067* (2013.01); *H01L 51/0074* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 9,079,920 B2 * | 7/2015 | Park .................... | C07D 491/147 |
| 2006/0124921 A1 * | 6/2006 | Ong ..................... | C07D 487/04 257/40 |

* cited by examiner

*Primary Examiner* — J. L. Yang
(74) *Attorney, Agent, or Firm* — Vorys, Sater, Seymour & Pease LLP; Mih Suhn Koh

(57) ABSTRACT

Disclosed is a compound represented by Formula 1 or Formula 2, and an organic electric element comprising a first electrode, a second electrode, and an organic material layer between the first electrode and the second electrode, wherein the organic material layer comprises the compound of Formula 1 or 2 to improve luminous efficiency, stability, and life span.

20 Claims, 6 Drawing Sheets

COMPOUND CONTAINING 5-MEMBERED HETEROCYCLES, ORGANIC ELECTRONIC DEVICE USING SAME, AND TERMINAL COMPRISING THE LATTER

CROSS-REFERENCE TO RELATED APPLICATION

This application is a continuation in part of U.S. patent application Ser. No. 13/390,043 filed on Feb. 10, 2012, which was a National Phase Application filed under 35 U.S.C. §371 of PCT/KR2010/005206 filed on Aug. 9, 2010, which claims priority to Korean Patent Application No. 10-2009-0073915 filed on Aug. 11, 2009, which are incorporated herein by reference in their entirety.

BACKGROUND OF THE INVENTION

1. Field of the invention

The present invention relates to a compound containing 5-membered heterocycles, an organic electronic device using the same, and a terminal including the latter.

2. Description of the Prior Art

In general, an organic light emitting phenomenon indicates conversion of electric energy into light energy by means of an organic material. An organic electronic device using the organic light emitting phenomenon generally has a structure including an anode, a cathode, and an organic material layer interposed therebetween. In many cases, the organic material layer has a multi-layered structure having respectively different materials in order to improve efficiency and stability of an organic electronic device. For example, it may include a hole injection layer, a hole transport layer, a light emitting layer, an electron transport layer, an electron injection layer, or the like.

Materials used as an organic material layer in an organic electronic device may be classified into a light emitting material and a charge transport material, for example, a hole injection material, a hole transport material, an electron transport material, an electron injection material, etc. according to their functions. Then, the light emitting material may be divided into a high molecular weight type and a low molecular weight type according to their molecular weight, and may be divided into a fluorescent material from electronic singlet excited states and a phosphorescent material from electronic triplet excited states according to their light emitting mechanism. Further, the light emitting material can be classified into a blue, green or red light emitting material and a yellow or orange light emitting material required for giving a more natural color, according to a light emitting color.

Meanwhile, when only one material is used as a light emitting material, an efficiency of a device is lowered owing to a maximum luminescence wavelength being moved to a longer wavelength due to the interaction between the molecules, the deterioration of color purity and the reduction in light emitting efficiency. Therefore, a host/dopant system can be used as the light emitting material for the purpose of enhancing the color purity and the light emitting efficiency through energy transfer. It is based on the principle that if a small amount of a dopant having a smaller energy band gap than a host forming a light emitting layer is mixed with the light emitting layer, excitons which are generated in the light emitting layer are transported to the dopant, thus emitting a light having a high efficiency. Here, since the wavelength of the host is moved according to the wavelength of the dopant, a light having a desired wavelength can be obtained according the kind of the dopant.

In order to allow the organic electronic device to fully exhibit the above-mentioned excellent characteristics, a material constituting the organic material layer in the device, for example, a hole injection material, a hole transport material, a light emitting material, an electron transport material and an electron injection material should be essentially composed of a stable and efficient material. However, the development of a stable and efficient organic material layer material for the organic electronic device has not yet been fully realized. Accordingly, the development of new materials is continuously desired.

SUMMARY OF THE INVENTION

In order to solve the above-mentioned problems in prior art, the inventors of the present invention found that when a novel-structural compound including three or more 5-membered heterocycles is employed in an organic electronic device, it is possible to significantly improve luminous efficiency, stability, and a life span of the device.

Accordingly, an object of the present invention is to provide a novel compound containing 5-membered heterocycles, an organic electronic device using the same, and a terminal including the latter.

In accordance with an aspect of the present invention, a compound represented by the following formula is provided:

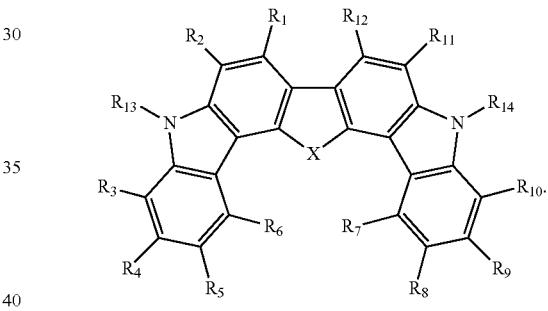

In accordance with another aspect of the present invention, another compound represented by the following formula is provided:

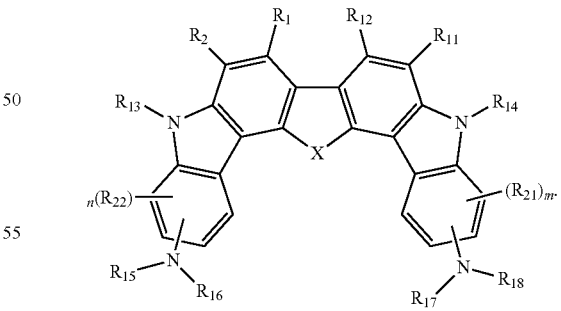

The inventive novel-structural compound of the formula above having three or more 5-membered heterocycles in the structure, may be used as a hole injection material, a hole transport material, a light emitting material, and/or an electron transport material appropriate for a fluorescent or phosphorescent device of all colors (such as red, green, blue, white, etc.), and is useful as a host material for various colors of a phosphorescent dopant.

Further, in accordance with an aspect of the present invention, an organic electronic device comprising either of the compounds represented by the formula above, and a terminal comprising the organic electronic device are provided.

According to an embodiment of the present invention, the compound having three or more 5-membered heterocycles in the structure can perform various roles in an organic electronic device and a terminal thereof. In particular, it is useful as a hole injection material, a hole transport material, a light emitting material, and/or an electron transport material appropriate for a fluorescent or phosphorescent device of all colors (such as red, green, blue, white, etc.), and preferably useful as a host material for various colors of a phosphorescent dopant.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Figure 1:
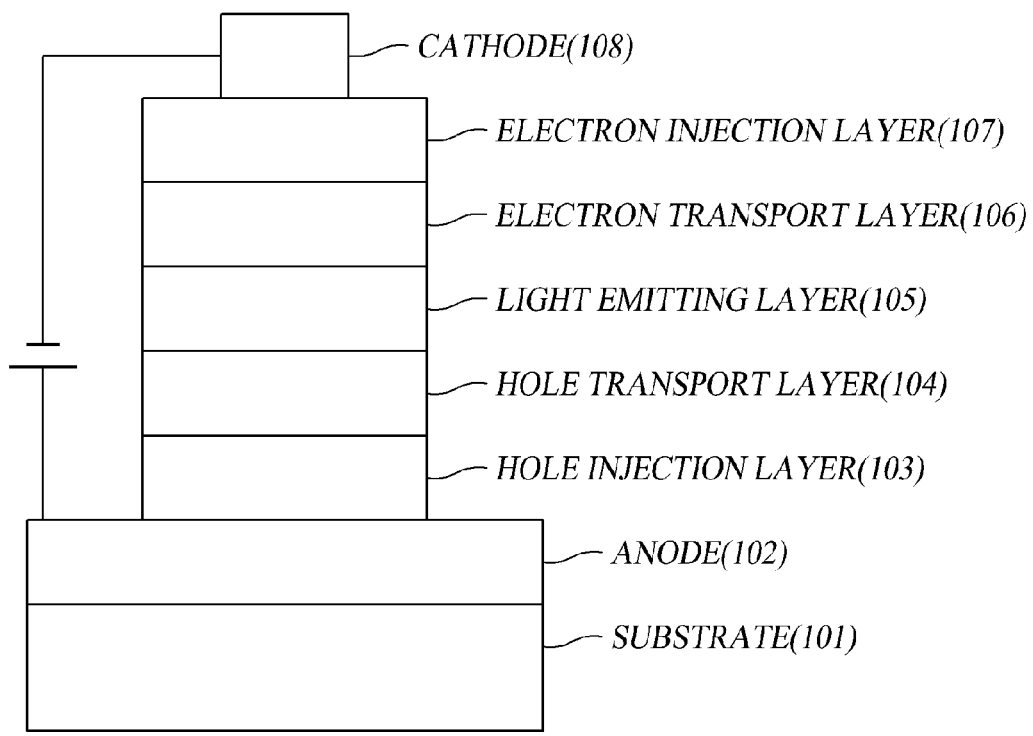
FIGS. 1 to 6 each show an example of an organic electroluminescence device which can employ a compound according to the present invention.

Hereinafter, exemplary embodiments of the present invention will be described with reference to the accompanying drawings. In the following description, the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

The present invention provides a compound represented by Formula 1 below:

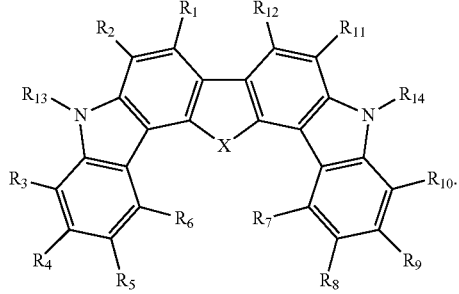

[Formula 1]

In Formula 1, (1) $R_1, R_2, R_3, R_4, R_5, R_6, R_7, R_8, R_9, R_{10}, R_{11}$ and $R_{12}$ each are independently selected from the group consisting of a hydrogen atom, a halogen atom, a cyano group, an alkoxy group, a thiol group, a substituted or unsubstituted alkyl group having 1 to 50 carbon atoms, a substituted or unsubstituted alkoxy group having 1 to 50 carbon atoms, a substituted or unsubstituted alkenyl group having 1 to 50 carbon atoms, a substituted or unsubstituted arylene group having 5 to 60 carbon atoms, a substituted or unsubstituted aryl group having 5 to 60 carbon atoms, a substituted or unsubstituted aryloxy group having 5 to 60 carbon atoms, a substituted or unsubstituted $C_1$~$C_{50}$ alkyl group having at least one of sulfur (S), nitrogen (N), oxygen(O), phosphorous (P) and silicon (Si), a substituted or unsubstituted $C_5$~$C_{60}$ heteroaryl group having at least one of sulfur (S), nitrogen (N), oxygen(O), phosphorous (P) and silicon (Si), and a substituted or unsubstituted $C_5$~$C_{60}$ heteroaryloxy group having at least one of sulfur, nitrogen, oxygen, phosphorous and silicon.

(2) $R_{13}$ and $R_{14}$ each are independently selected from the group consisting of a hydrogen atom, a substituted or unsubstituted alkyl group having 1 to 50 carbon atoms, a substituted or unsubstituted alkoxy group having 1 to 50 carbon atoms, a substituted or unsubstituted alkenyl group having 1 to 50 carbon atoms, a substituted or unsubstituted arylene group having 5 to 60 carbon atoms, a substituted or unsubstituted aryl group having 5 to 60 carbon atoms, a substituted or unsubstituted aryloxy group having 5 to 60 carbon atoms, a substituted or unsubstituted $C_1$~$C_{50}$ alkyl group having at least one of sulfur (S), nitrogen (N), oxygen(O), phosphorous (P) and silicon (Si), a substituted or unsubstituted $C_5$~$C_{60}$ heteroaryl group having at least one of sulfur (S), nitrogen (N), oxygen(O), phosphorous (P) and silicon (Si), and a substituted or unsubstituted $C_5$~$C_{60}$ heteroaryloxy group having at least one of sulfur, nitrogen, oxygen, phosphorous and silicon.

(3) X may include carbon (CRaRb), nitrogen (NRc), oxygen (O), phosphorous (PRd), sulfur (S), silicon (SiReRf) or germanium (GeRgRh), wherein Ra, Rb, Rc, Rd, Re, Rf, Rg and Rh each are independently selected from the group including an alkyl group having 1 to 50 carbon atoms, and an aryl group having 6 to 60 carbon atoms.

(4) At least one of $R_1$ and $R_2$, $R_3$ and $R_4$, $R_4$ and $R_5$, $R_5$ and $R_6$, $R_7$ and $R_8$, $R_8$ and $R_9$, $R_9$ and $R_{10}$, and $R_{11}$ and $R_{12}$, but not all of them, may form a saturated or unsaturated cyclic ring together with an adjacent group.

(5) $R_2$ and $R_{13}$, and/or $R_{11}$ and $R_{14}$ may form a saturated or unsaturated cyclic ring together with an adjacent group.

(6) The compound represented by Formula 1 may have a symmetric or asymmetric structure with respect to X.

(7) The compound having the structural formula represented by Formula 1 may be used in a soluble process.

Also, in another aspect, the present invention provides a compound represented by Formula 2:

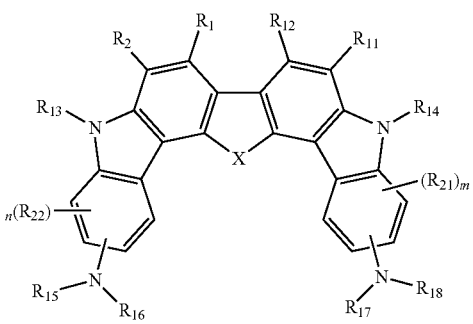

[Formula 2]

wherein, (1) $R_1$, $R_2$, $R_{11}$ and $R_{12}$ each are independently selected from the group consisting of a hydrogen atom, a halogen atom, a cyano group, an alkoxy group, a thiol group, a substituted or unsubstituted alkyl group having 1 to 50 carbon atoms, a substituted or unsubstituted alkoxy group having 1 to 50 carbon atoms, a substituted or unsubstituted alkenyl group having 1 to 50 carbon atoms, a substituted or unsubstituted arylene group having 5 to 60 carbon atoms, a substituted or unsubstituted aryl group having 5 to 60 carbon atoms, a substituted or unsubstituted aryloxy group having 5 to 60 carbon atoms, a substituted or unsubstituted $C_1$~$C_{50}$ alkyl group having at least one of sulfur (S), nitrogen (N), oxygen (O), phosphorous (P) and silicon (Si), a substituted or unsubstituted $C_5$~$C_{60}$ heteroaryl group having at least one of sulfur (S), nitrogen (N), oxygen(O), phosphorous (P) and silicon (Si), and a substituted or unsubstituted $C_5$~$C_{60}$ heteroaryloxy group having at least one of sulfur (S), nitrogen (N), oxygen (O), phosphorous (P) and silicon (Si).

(2) $R_{13}$ and $R_{14}$ each are independently selected from the group consisting of a hydrogen atom, a substituted or unsubstituted alkyl group having 1 to 50 carbon atoms, a substituted or unsubstituted alkoxy group having 1 to 50 carbon atoms, a substituted or unsubstituted alkenyl group having 1 to 50 carbon atoms, a substituted or unsubstituted arylene group having 5 to 60 carbon atoms, a substituted or unsubstituted aryl group having 5 to 60 carbon atoms, a substituted or unsubstituted aryloxy group having 5 to 60 carbon atoms, a substituted or unsubstituted $C_1$-$C_{50}$ alkyl group having at least one of sulfur (S), nitrogen (N), oxygen(O), phosphorous (P) and silicon (Si), a substituted or unsubstituted $C_5$~$C_{60}$ heteroaryl group having at least one of sulfur (S), nitrogen (N), oxygen(O), phosphorous (P) and silicon (Si), and a substituted or unsubstituted $C_5$~$C_{60}$ heteroaryloxy group having at least one of sulfur (S), nitrogen (N), oxygen (O), phosphorous (P) and silicon (Si).

(3) $R_{15}$, $R_{16}$, $R_{17}$ and $R_{18}$ each are independently selected from the group consisting of a hydrogen atom, a substituted or unsubstituted alkyl group having 1 to 50 carbon atoms, a substituted or unsubstituted aryl group having 5 to 60 carbon atoms, a substituted or unsubstituted aryloxy group having 5 to 60 carbon atoms, a substituted or unsubstituted $C_1$~$C_{50}$ alkyl group having at least one of sulfur (S), nitrogen (N), oxygen (O), phosphorous (P) and silicon (Si), a substituted or unsubstituted $C_5$~$C_{60}$ heteroaryl group having at least one of sulfur (S), nitrogen (N), oxygen (O), phosphorous (P) and silicon (Si), and a substituted or unsubstituted $C_5$~$C_{60}$ heteroaryloxy group having at least one of sulfur (S), nitrogen (N), oxygen (O), phosphorous (P) and silicon (Si).

(4) $R_{21}$ and $R_{22}$ are each independently selected from the group consisting of deuterium, halogen, a cyano group, a $C_6$-$C_{60}$ aryl group, a fluorenyl group, a fused ring group of a $C_3$-$C_{60}$ aliphatic ring and a $C_6$-$C_{60}$ aromatic ring, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, a $C_1$-$C_{30}$ alkoxy group, a $C_6$-$C_{30}$ aryloxy group, and -L-N(R')(R'').

(5) X may include carbon (CRaRb), nitrogen (NRc), oxygen (O), phosphorous (PRd), sulfur (S), silicon (SiReRf) or germanium (GeRgRh), wherein Ra, Rb, Rc, Rd, Re, Rf, Rg and Rh each are independently selected from the group including an alkyl group having 1 to 50 carbon atoms, and an aryl group having 6 to 60 carbon atoms.

(6) $R_1$ and $R_2$, or $R_{11}$ and $R_{12}$ may form a saturated or unsaturated cyclic ring together with an adjacent group.

(7) The compound having the structural formula represented by Formula 2 may be used in a soluble process.

According to one embodiment of the present invention, the compound of Formula 1 or 2 includes, but not limited to, the following specific compounds of Compound 1 to Compound 81, which is represented herein by Formula 3.

[Formula 3]

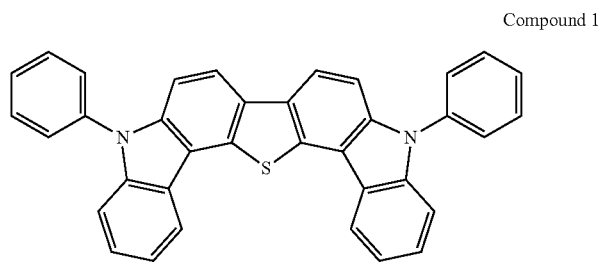

Compound 1

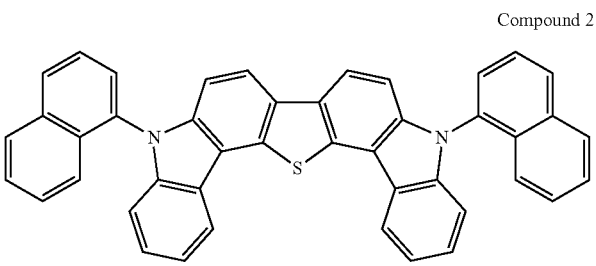

Compound 2

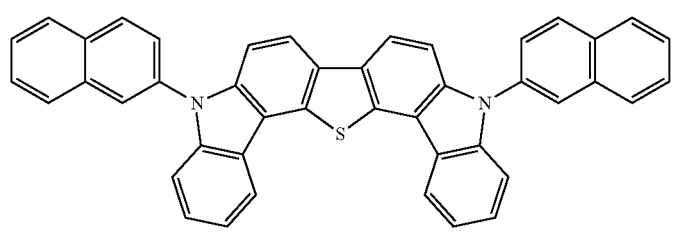

Compound 3

-continued
Compound 4
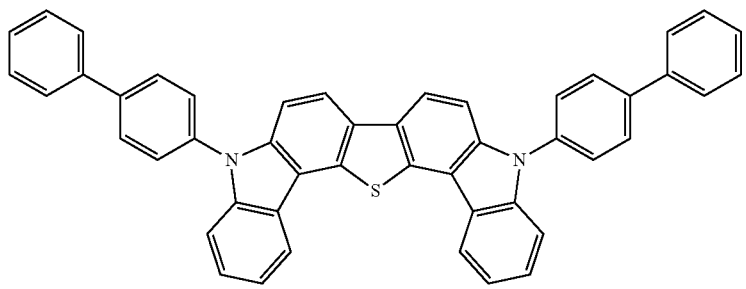
Compound 5
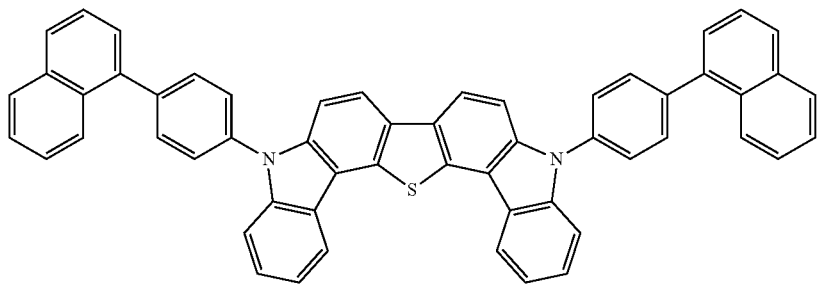
Compound 6
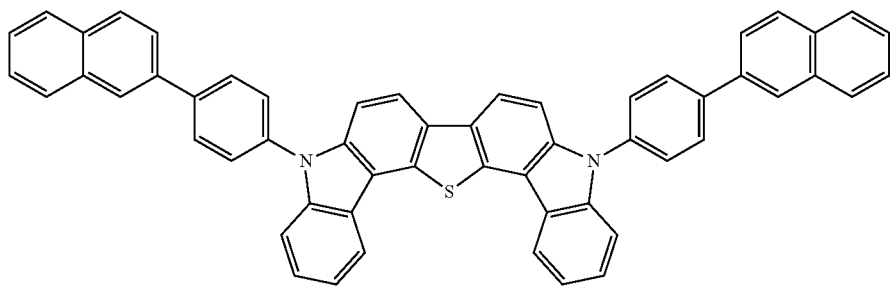
Compound 7
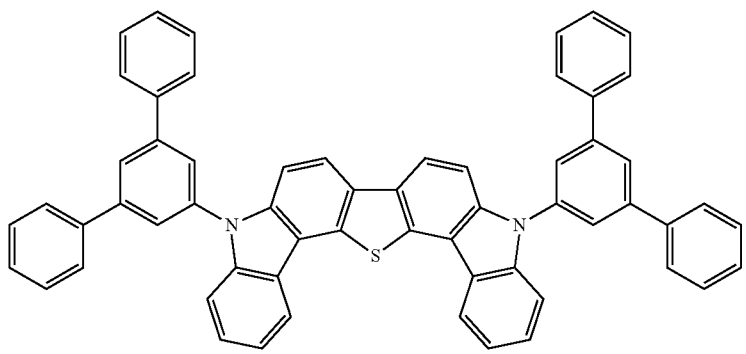
Compound 8
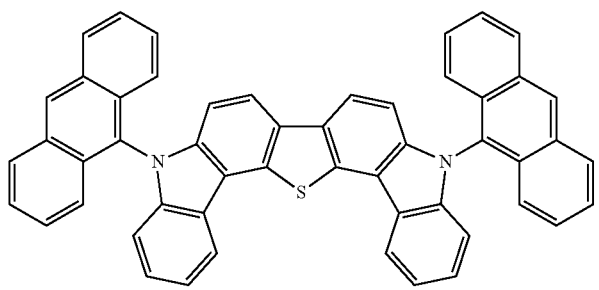
Compound 9
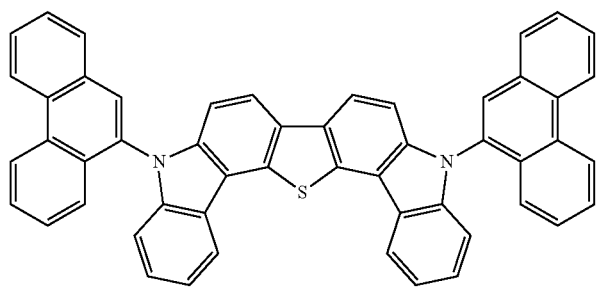

-continued
Compound 10
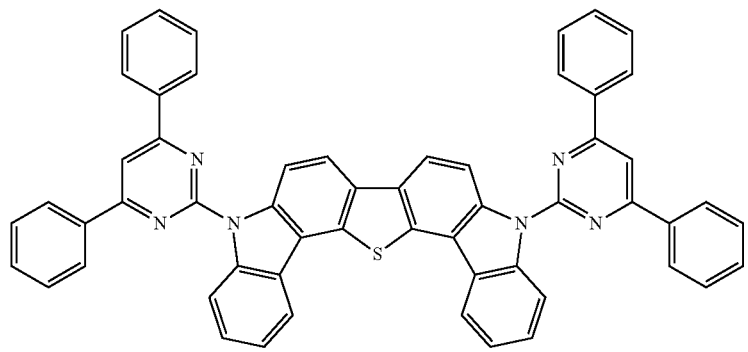
Compound 11
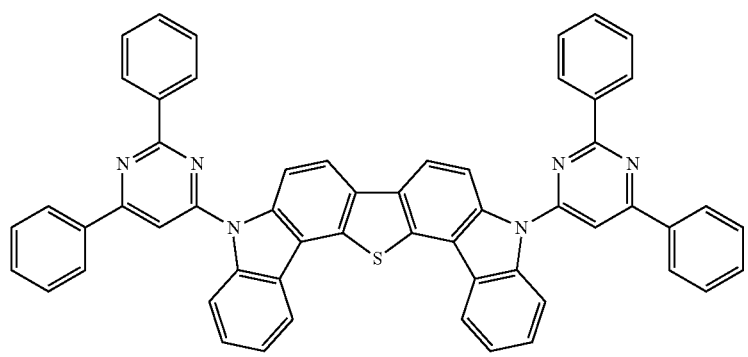
Compound 12
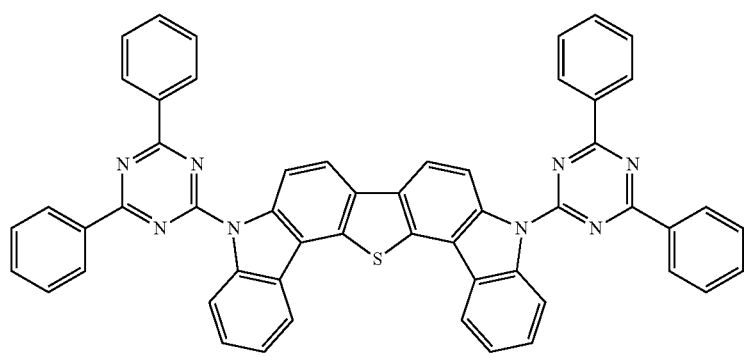
Compound 13
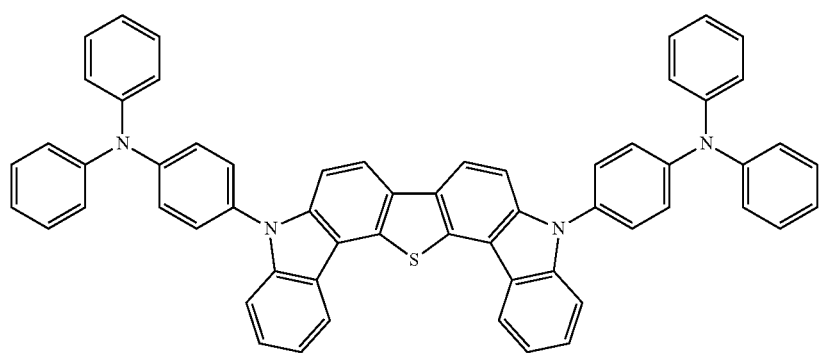

-continued
Compound 14
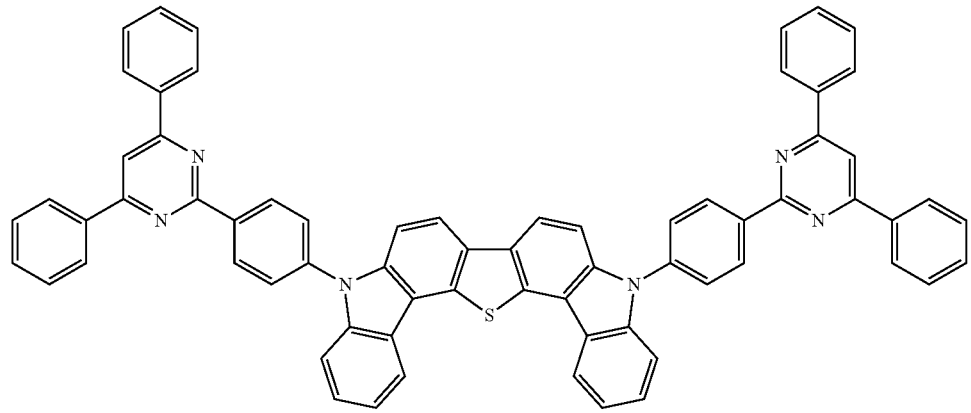
Compound 15
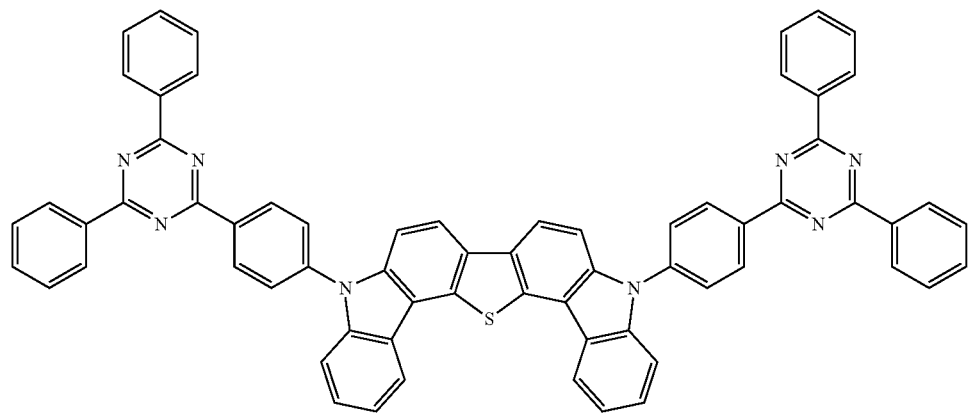
Compound 16
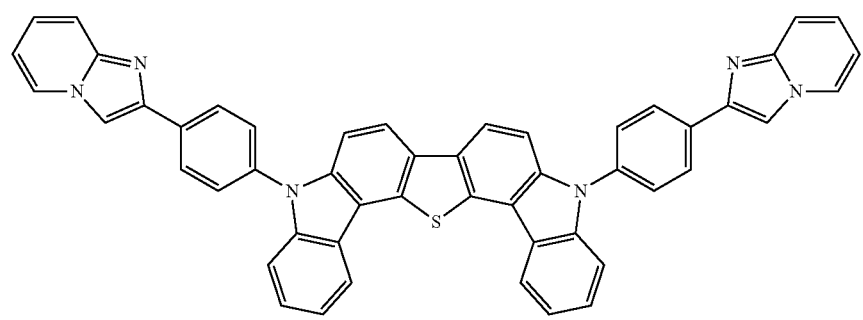
Compound 17
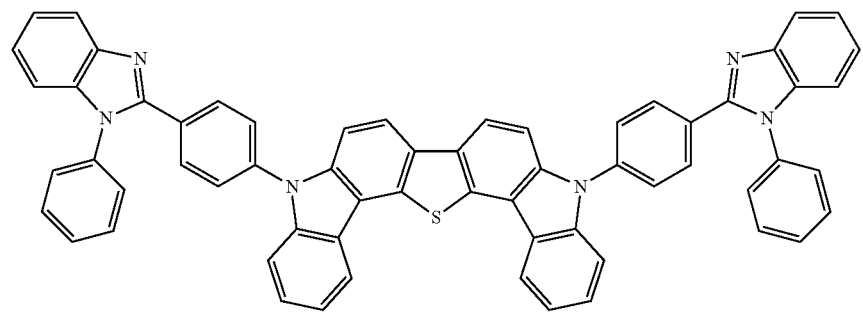

-continued
Compound 18
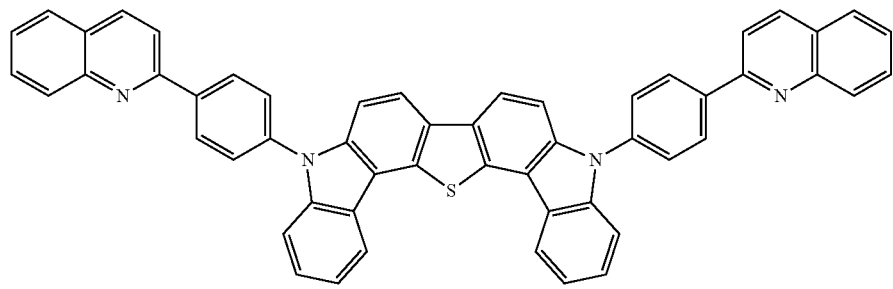
Compound 19
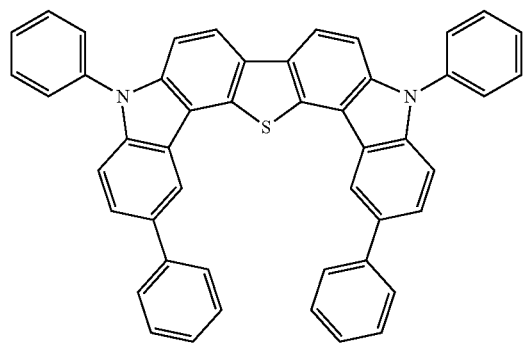
Compound 20
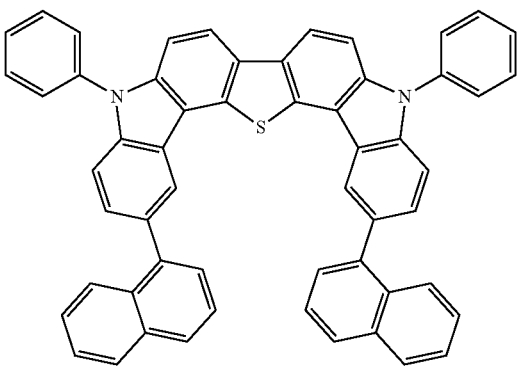
Compound 21
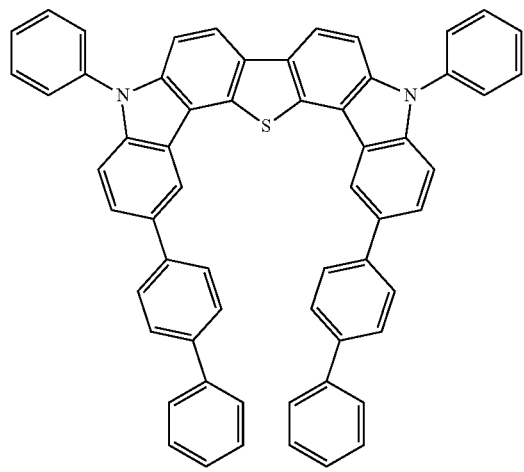
Compound 22
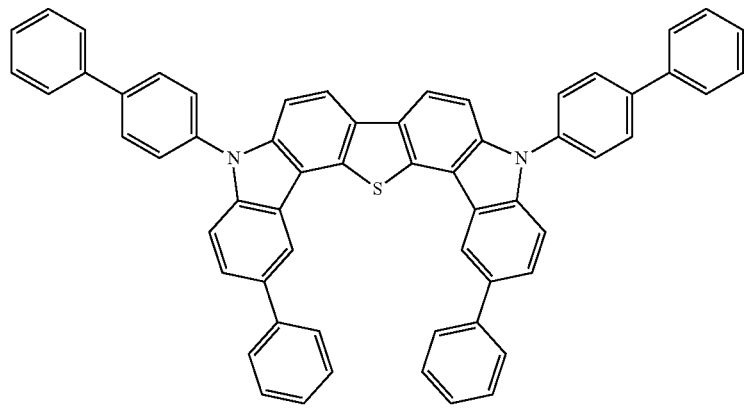

-continued
Compound 23
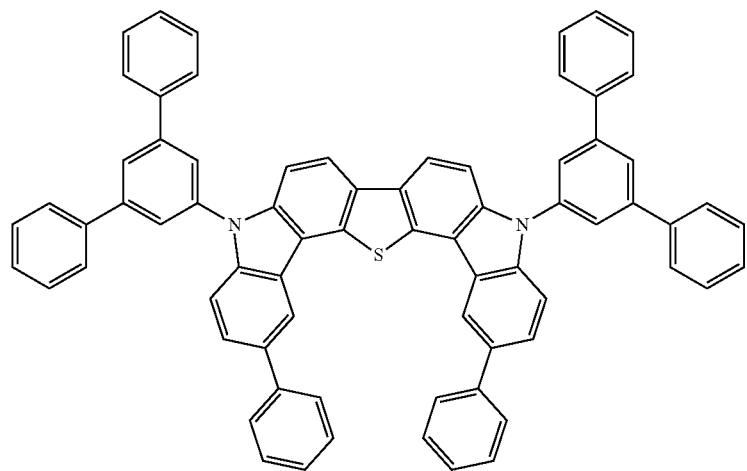
Compound 24
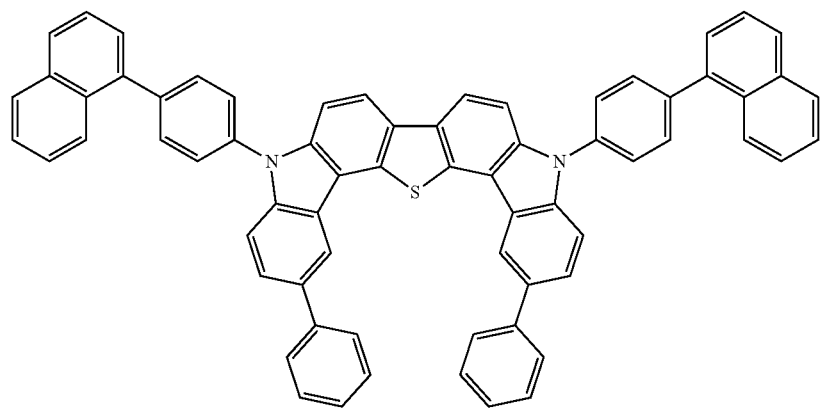
Compound 25
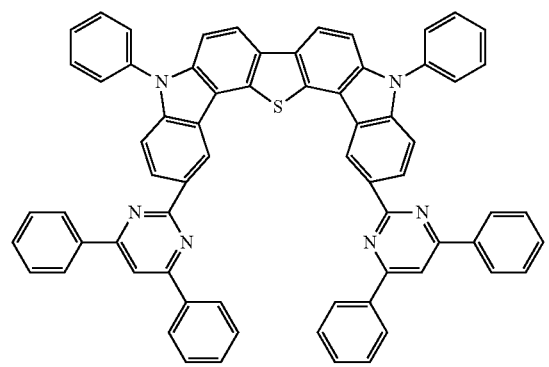
Compound 26
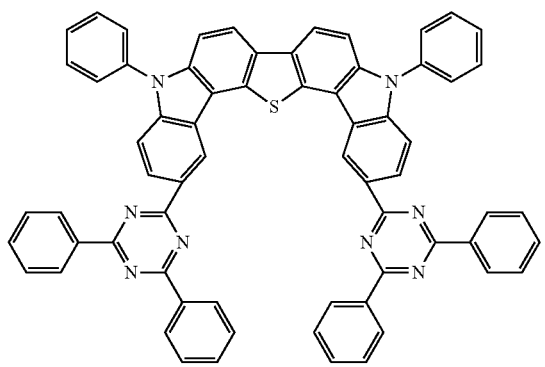

-continued
Compound 27
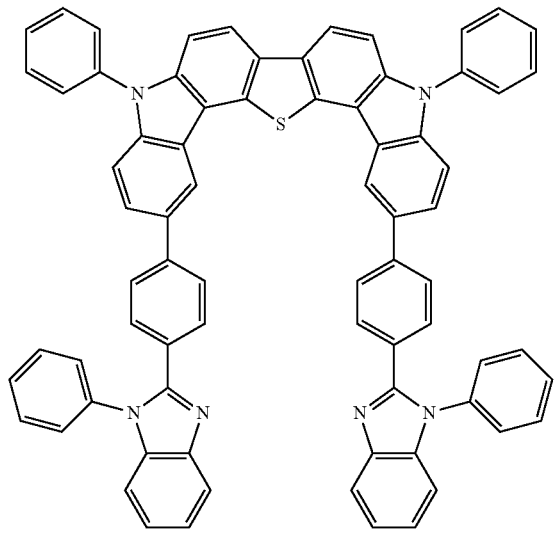
Compound 28
Compound 29
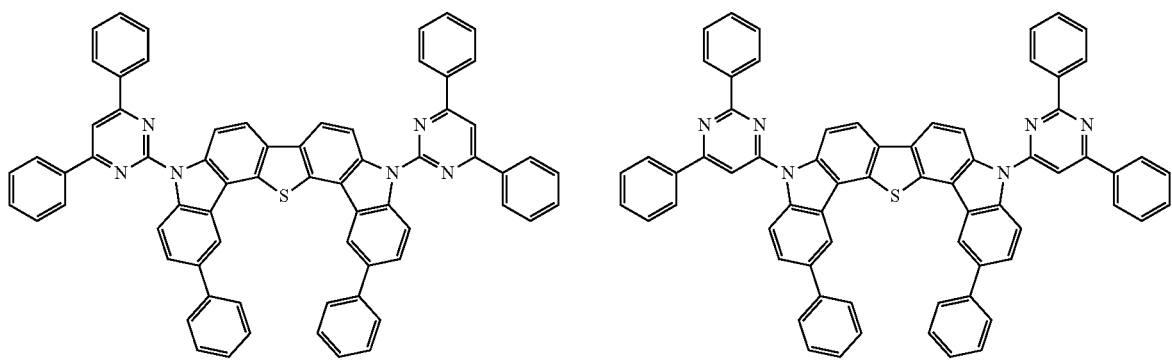
Compound 30
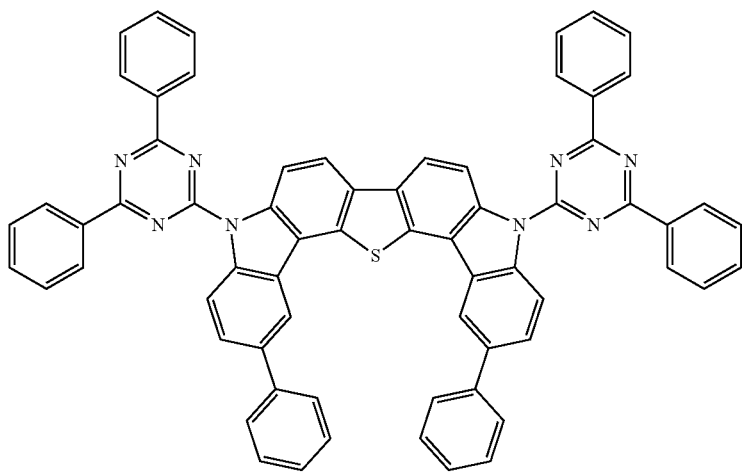

-continued
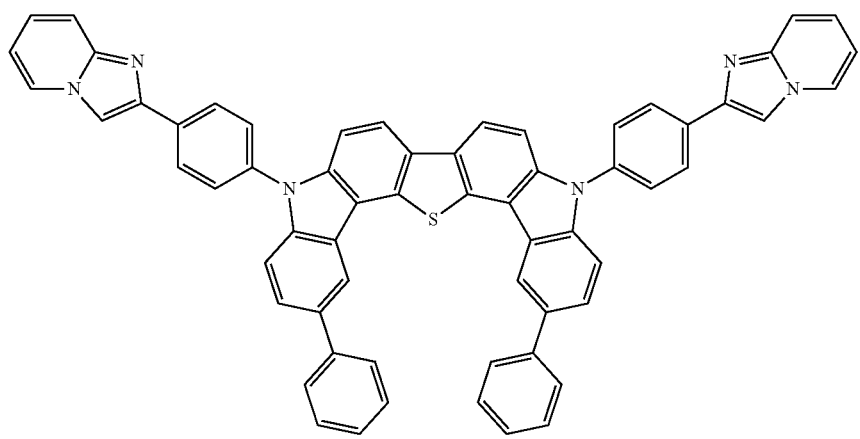
Compound 31
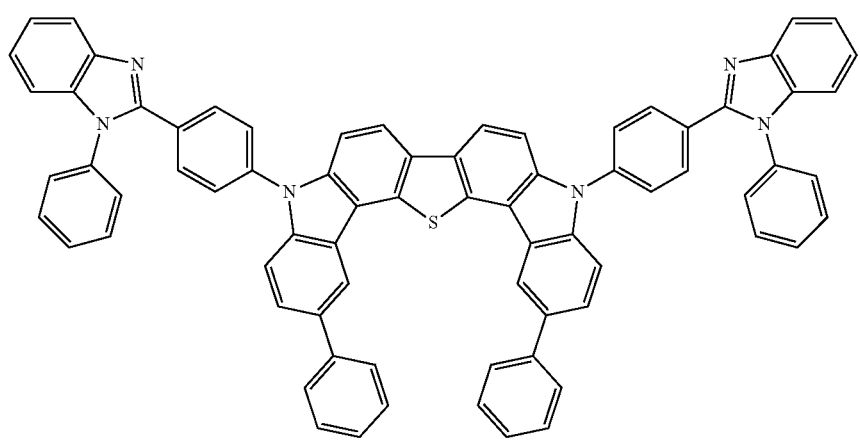
Compound 32
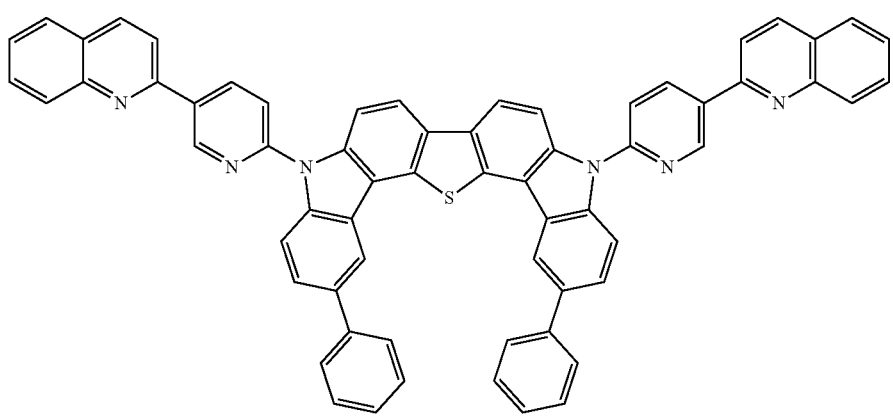
Compound 33

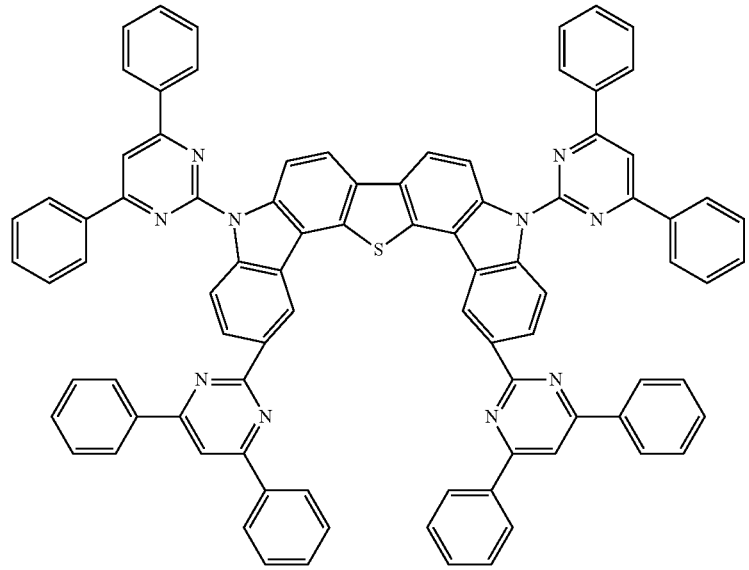
Compound 34
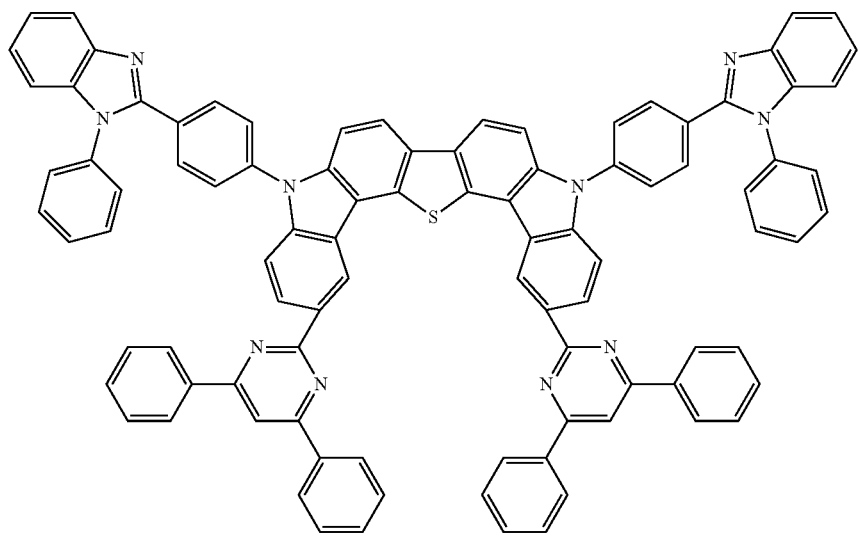
Compound 35

Compound 36
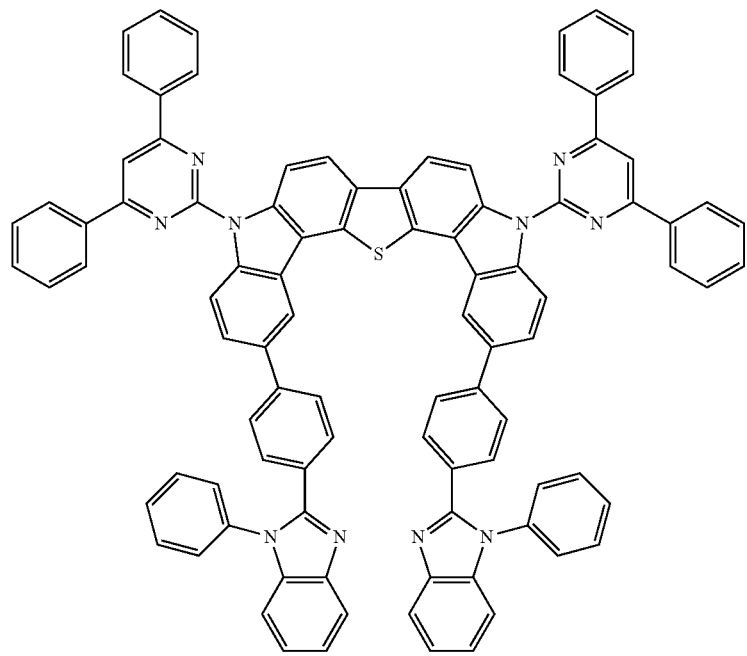
Compound 37
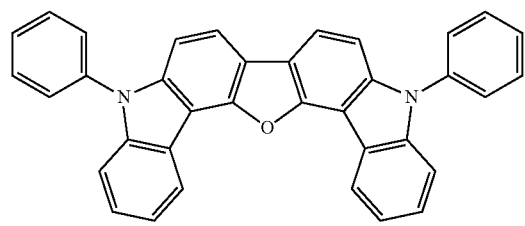
Compound 38
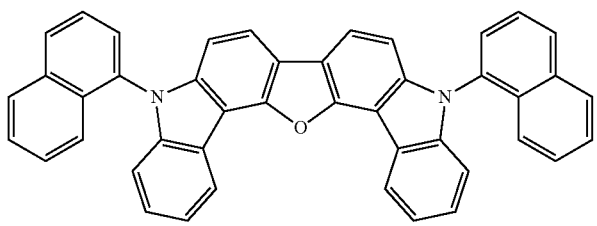
Compound 39
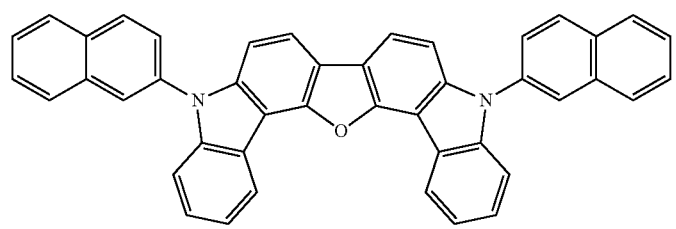
Compound 40
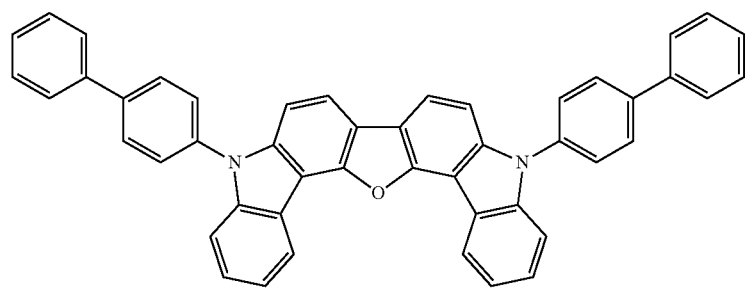

-continued
Compound 41
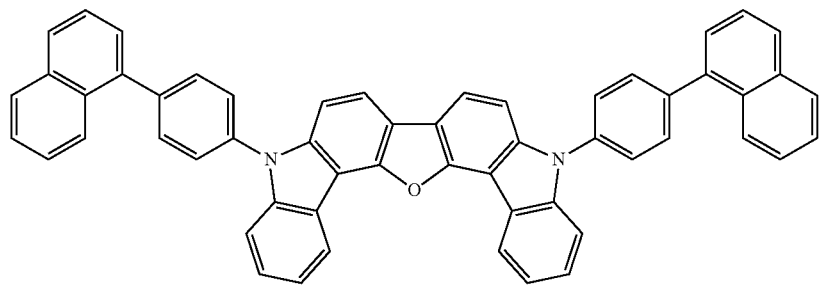
Compound 42
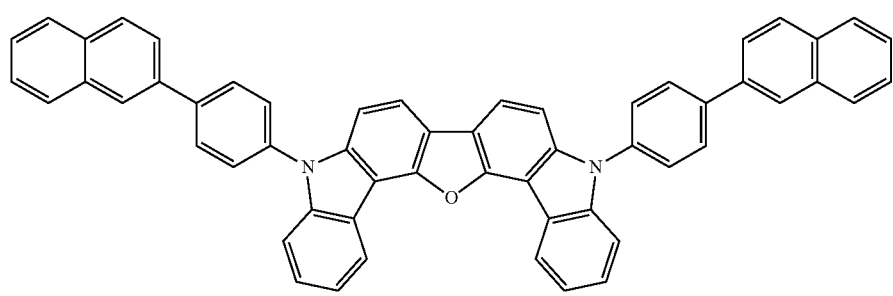
Compound 43
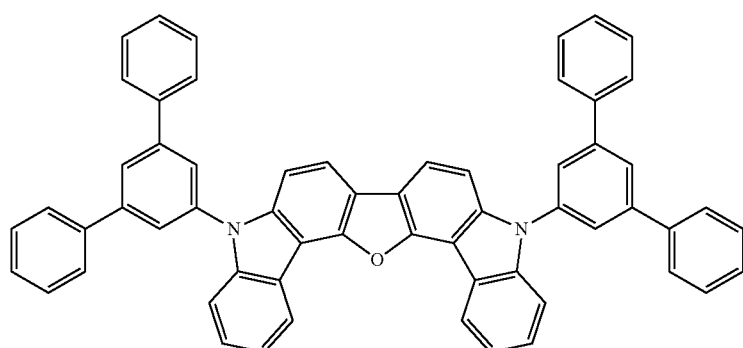
Compound 44                                                                Compound 45
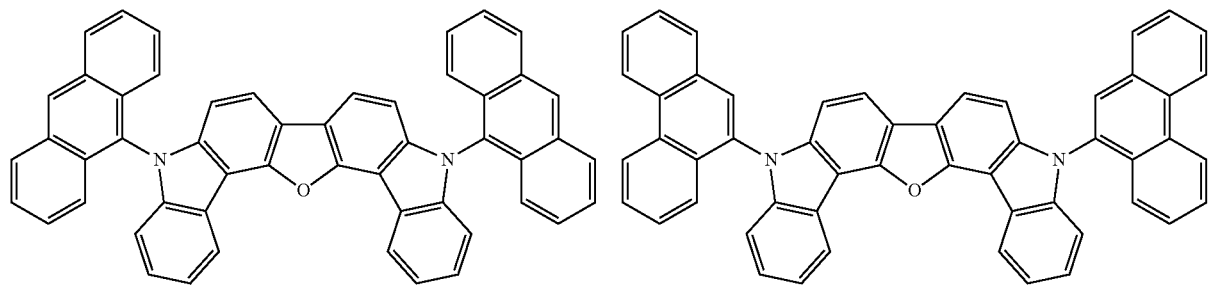
Compound 46                                  Compound 47
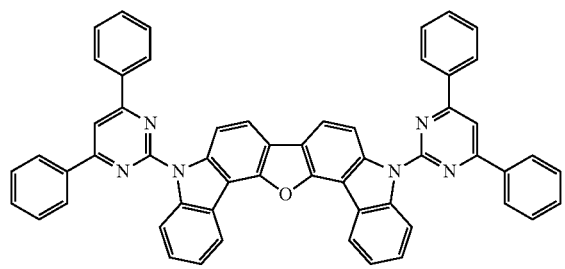 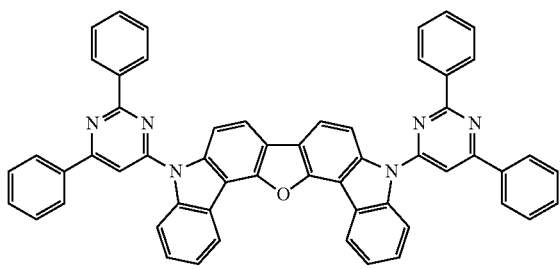

Compound 48
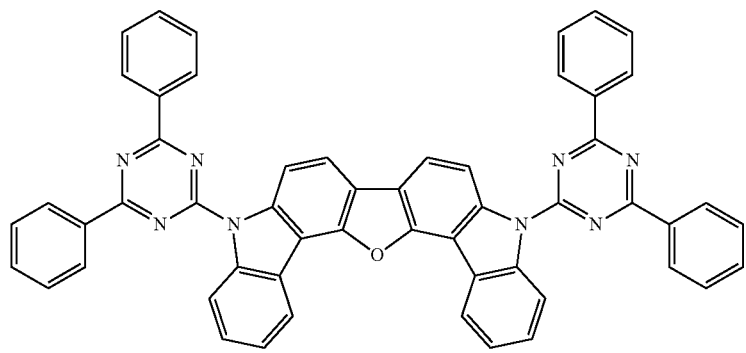
Compound 49
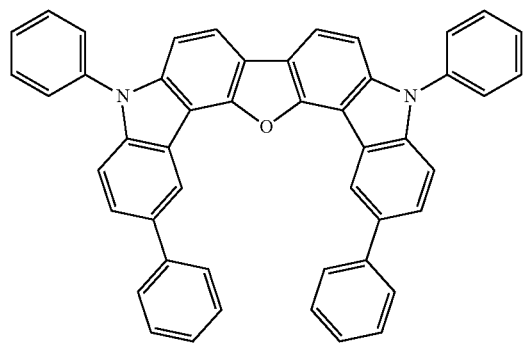
Compound 50
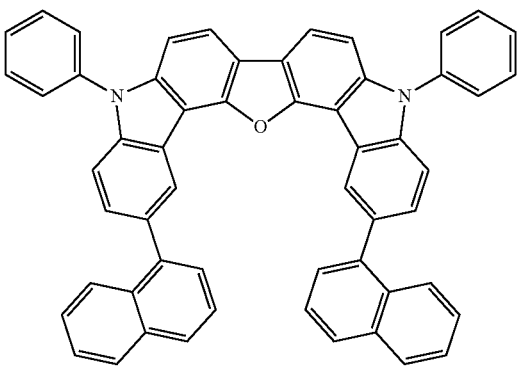
Compound 51
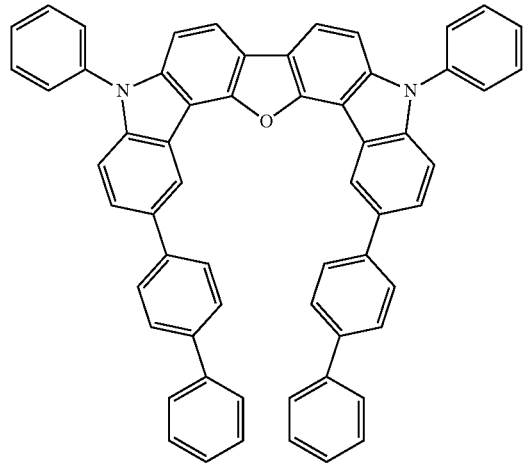
Compound 52
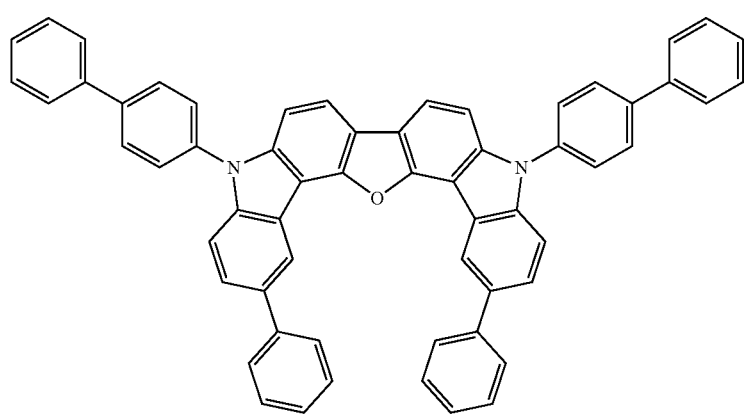

Compound 53
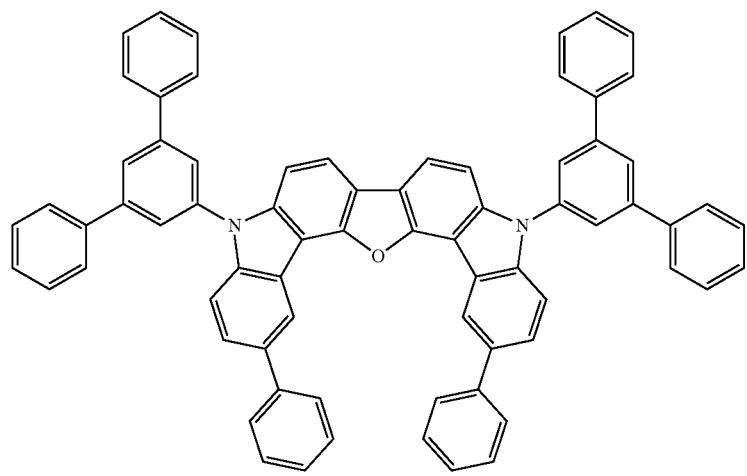
Compound 54
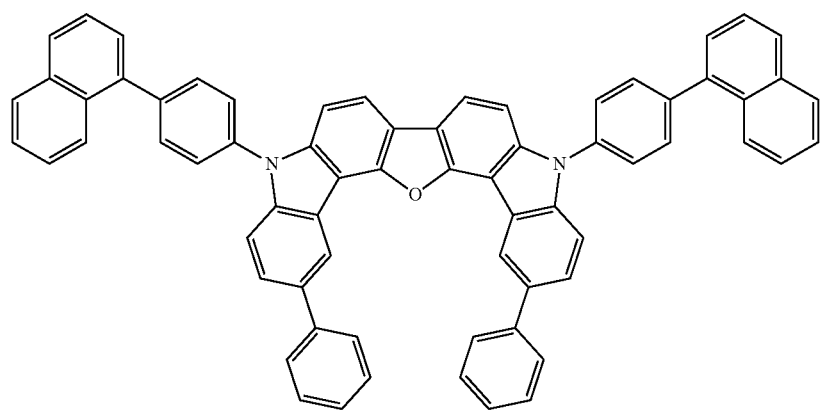
Compound 55
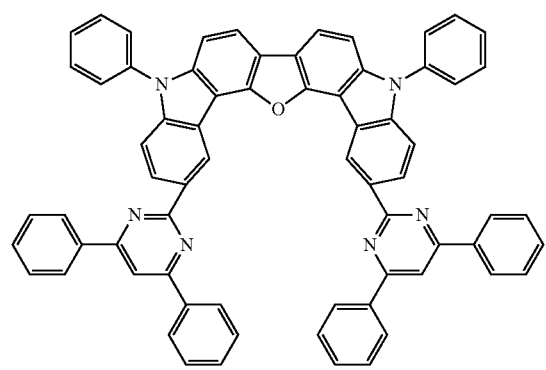
Compound 56
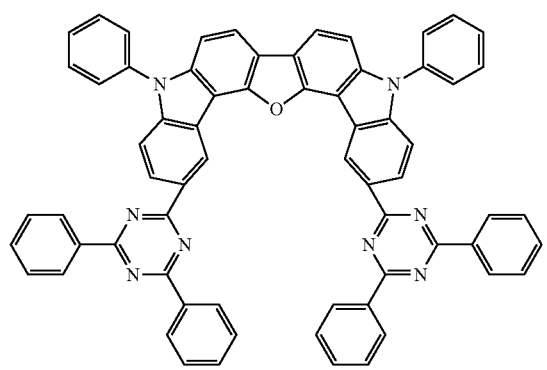

Compound 57
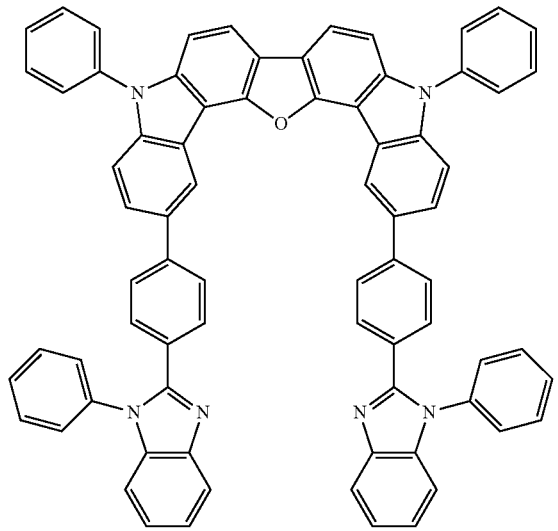
Compound 58
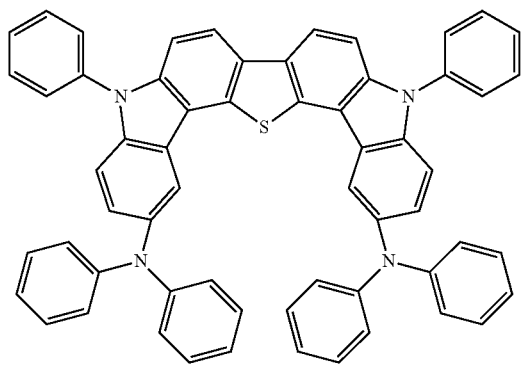
Compound 59
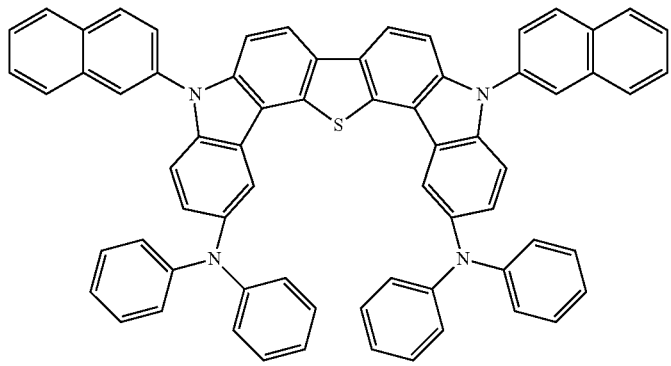

Compound 60
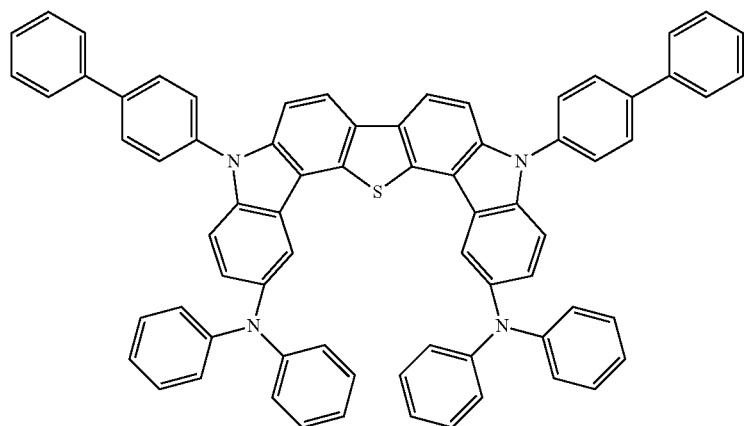
Compound 61
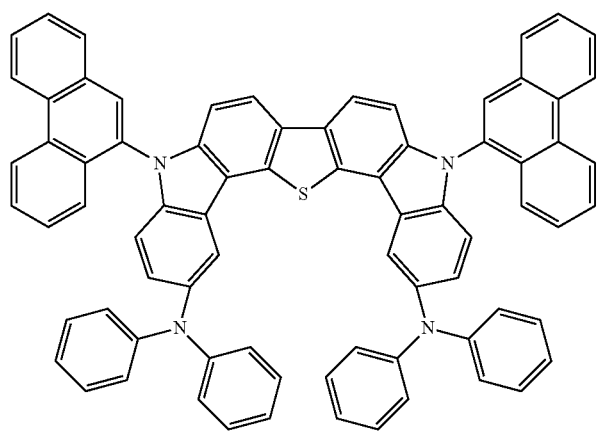
Compound 62
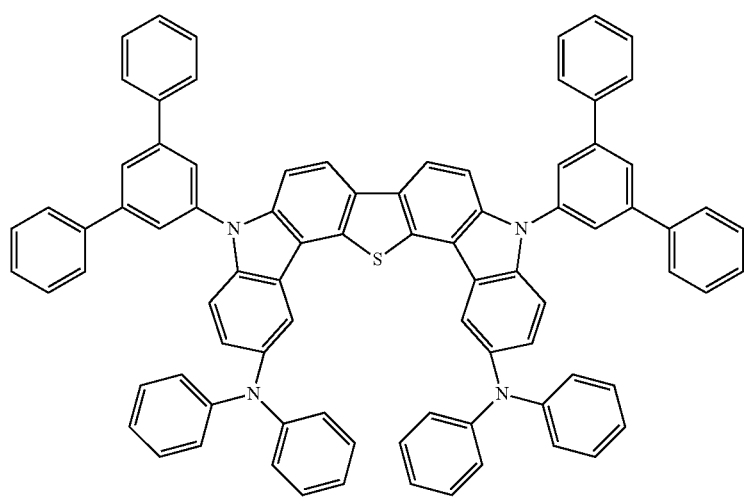

-continued
Compound 63
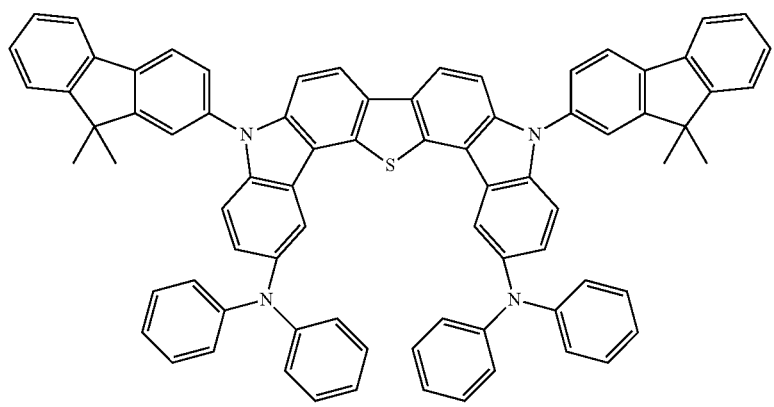
Compound 64
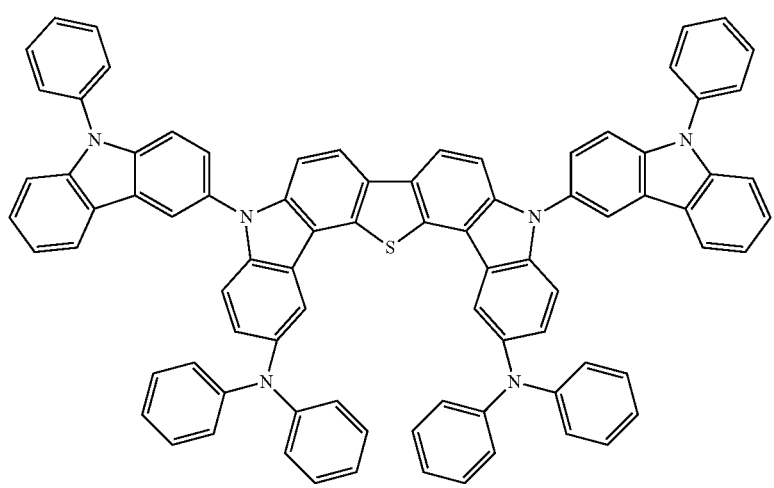
Compound 65
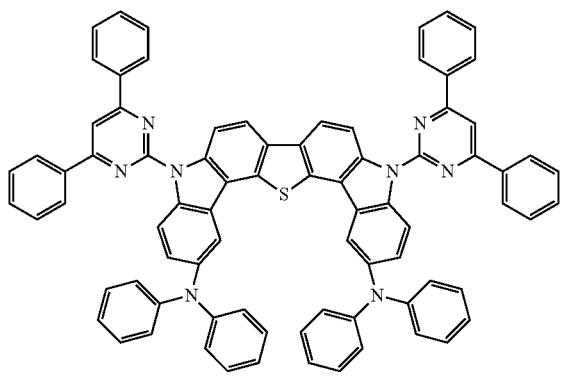
Compound 66
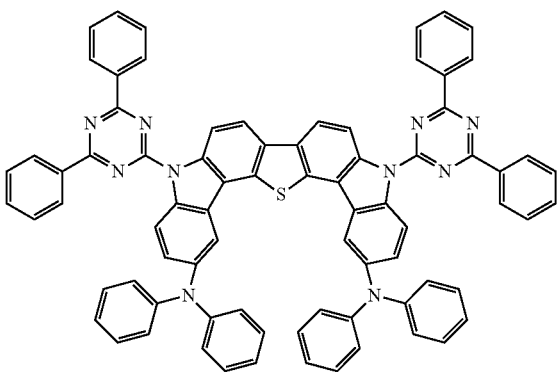
Compound 67
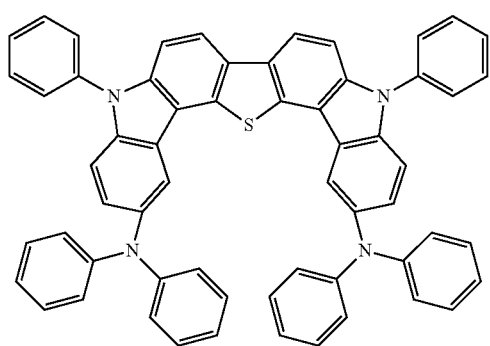
Compound 68
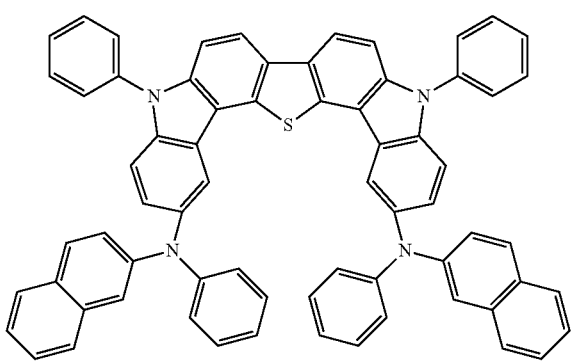

Compound 69
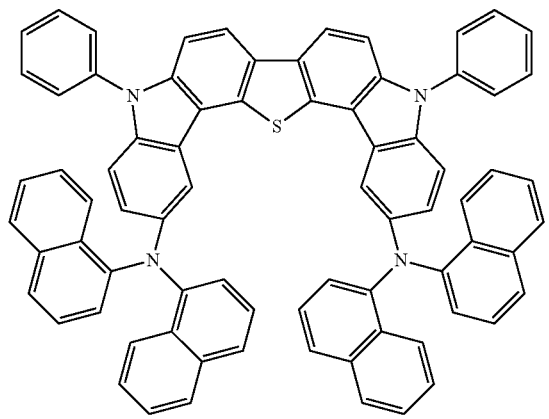
Compound 70
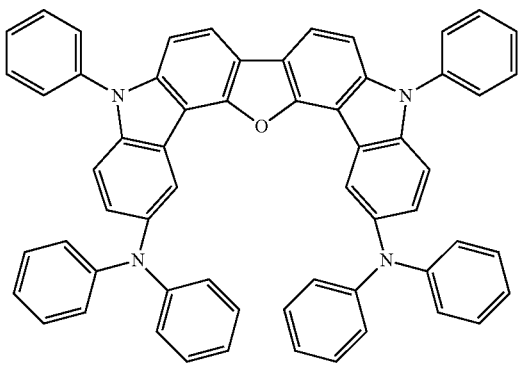
Compound 71
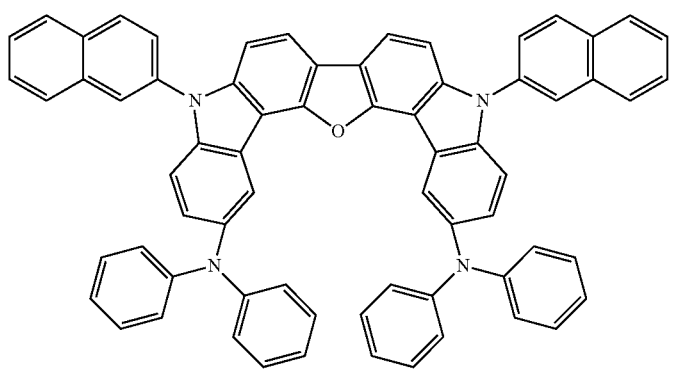
Compound 72
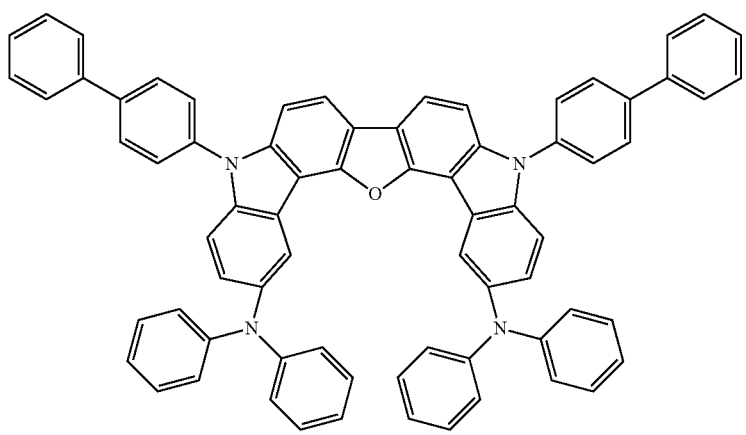

-continued
Compound 73
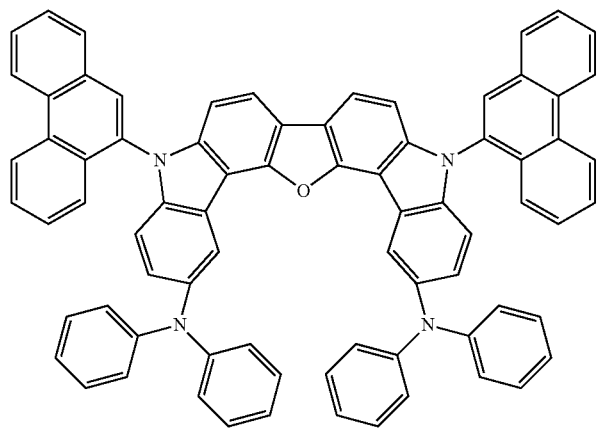
Compound 74
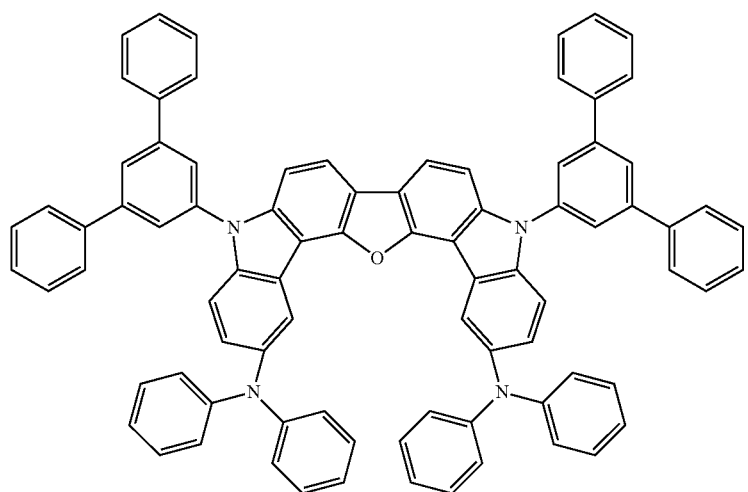
Compound 75
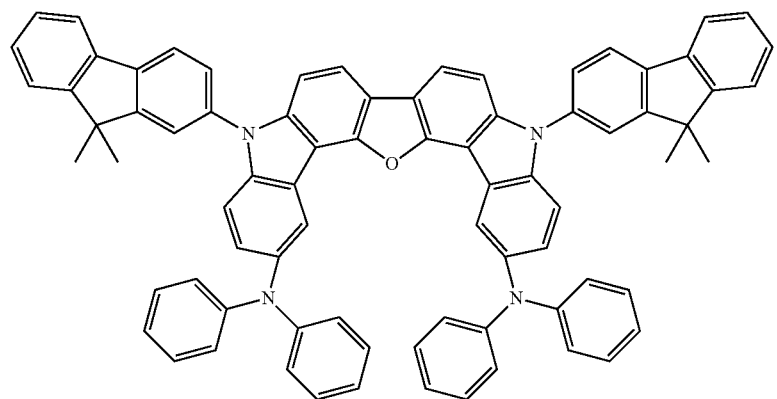

-continued
Compound 76
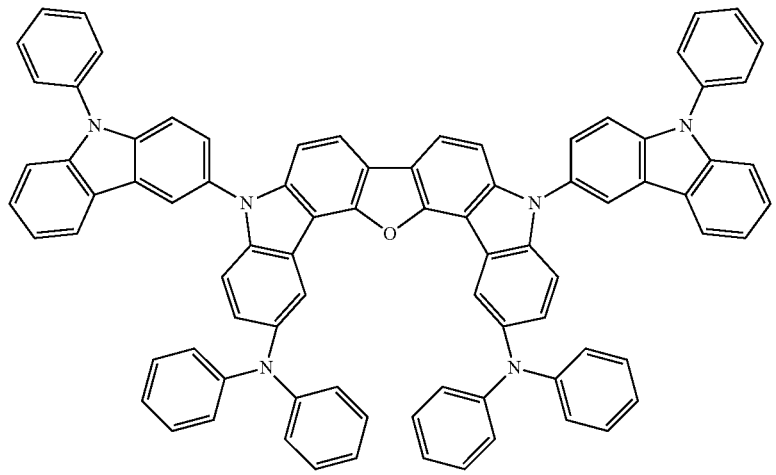
Compound 77
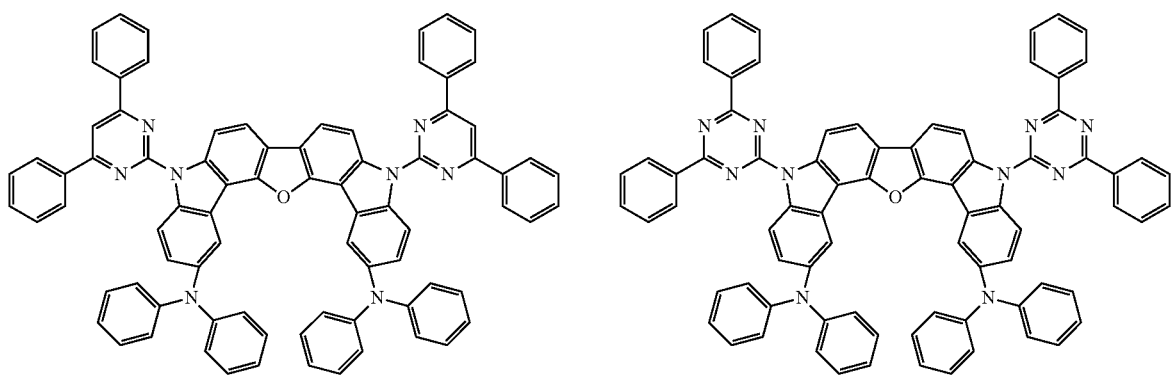
Compound 78
Compound 79
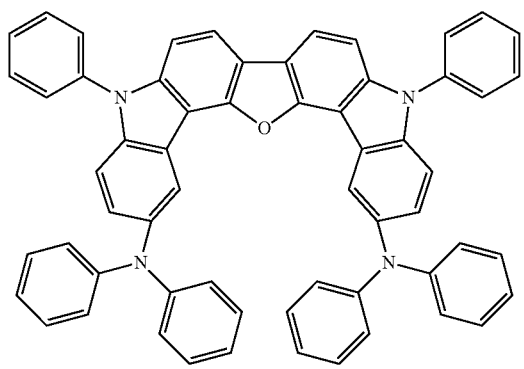
Compound 80
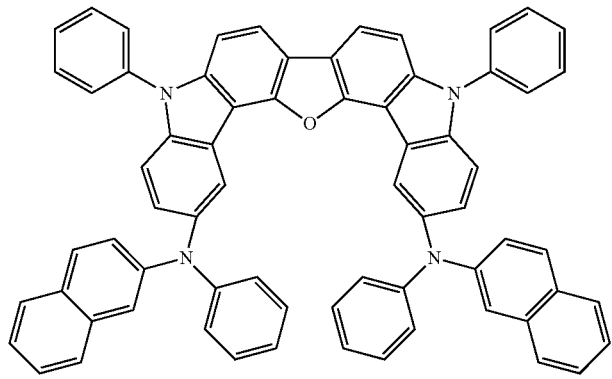

-continued
Compound 81
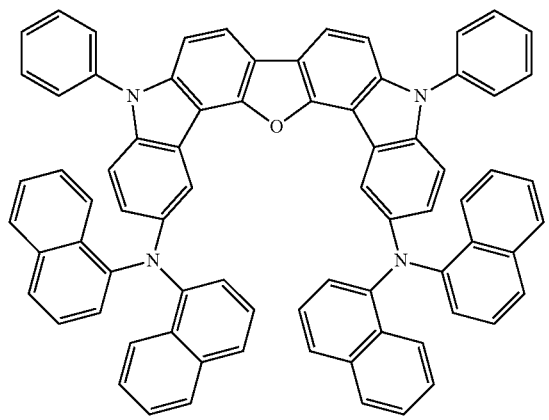
Compound 82
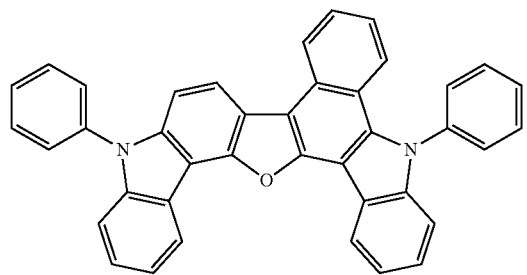
Compound 83
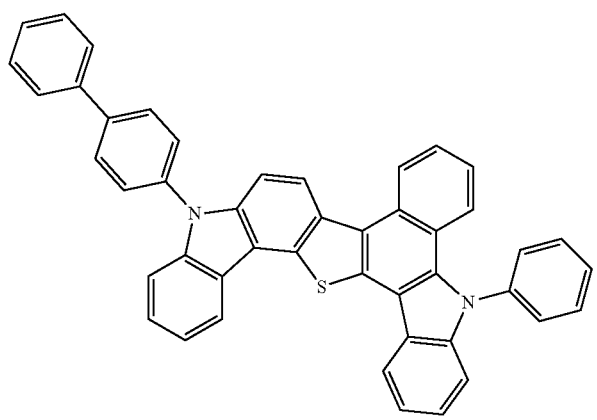
Compound 84
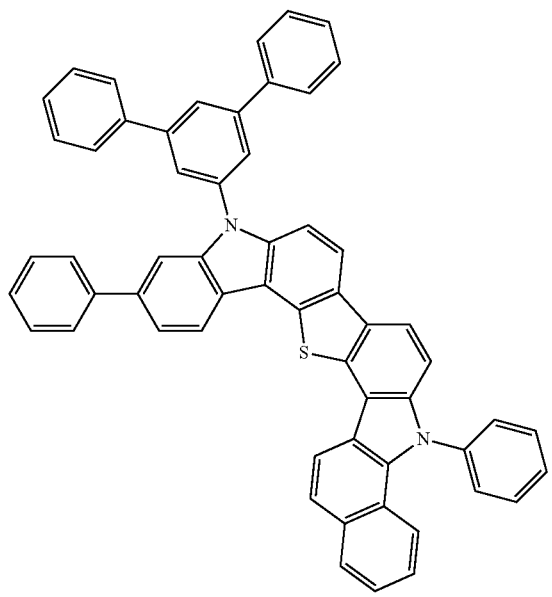
Compound 85
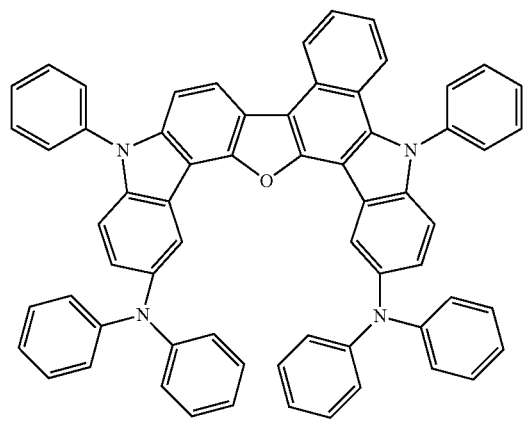

-continued
COMPOUND 86
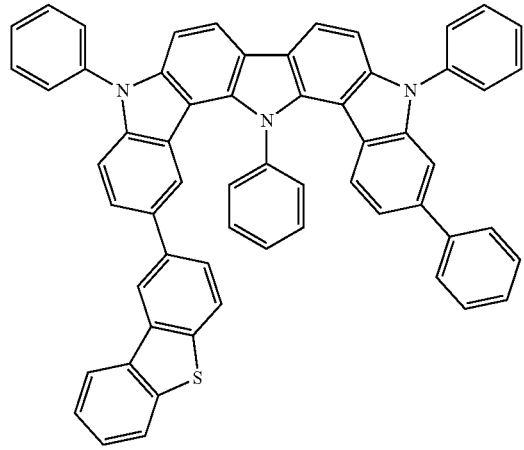
COMPOUND 87
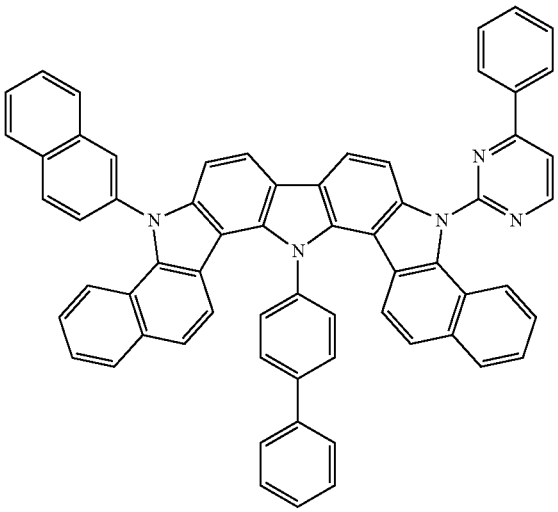
COMPOUND 88
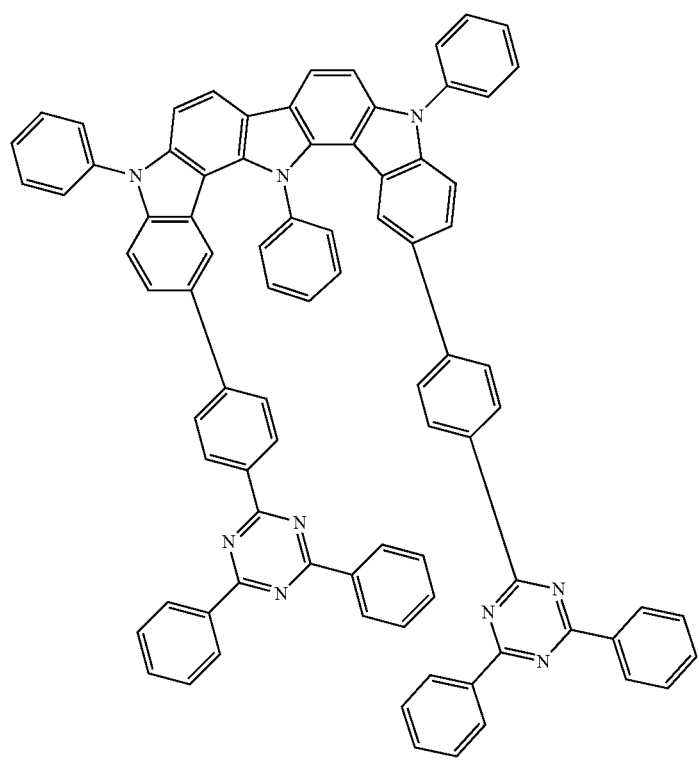
COMPOUND 89
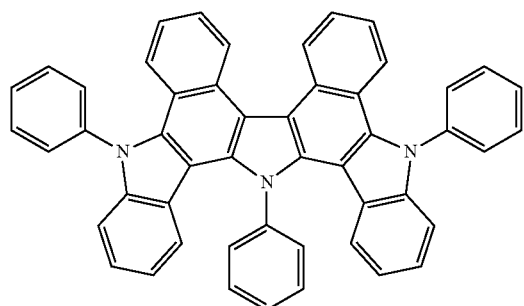

COMPOUND 90
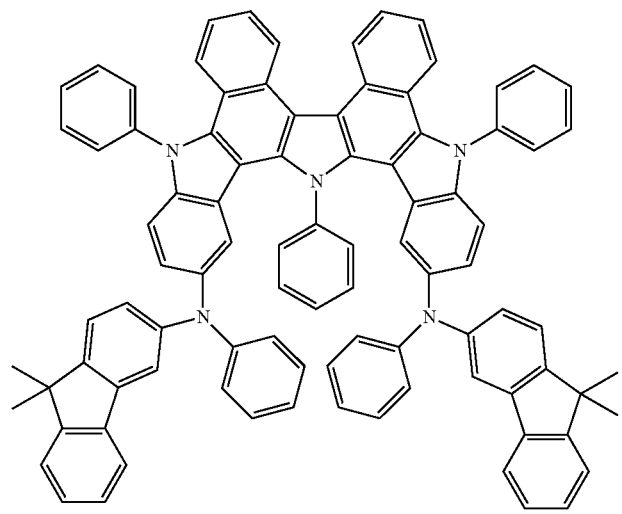
COMPOUND 91
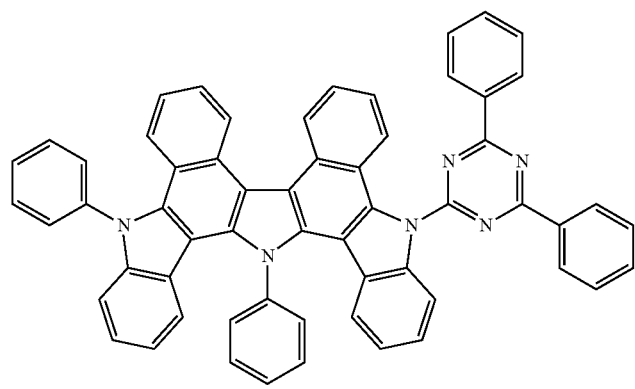
COMPOUND 92
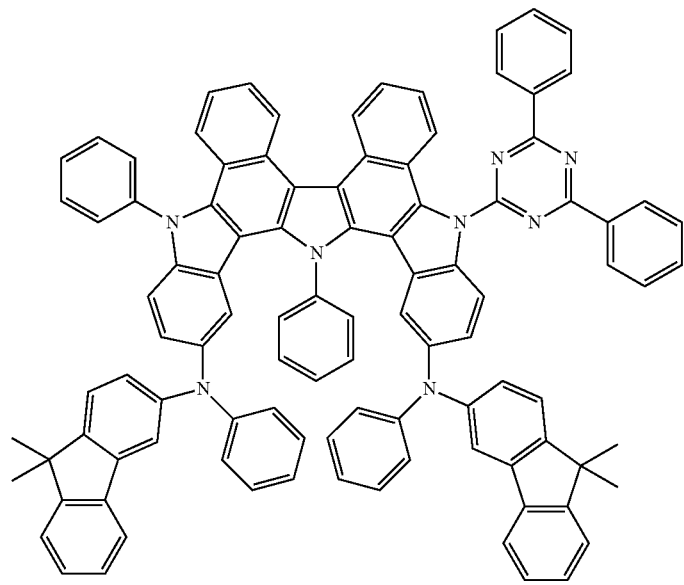

COMPOUND 93
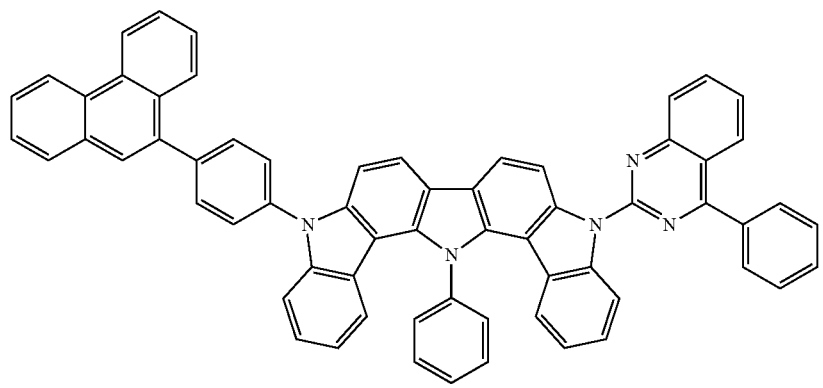
COMPOUND 94
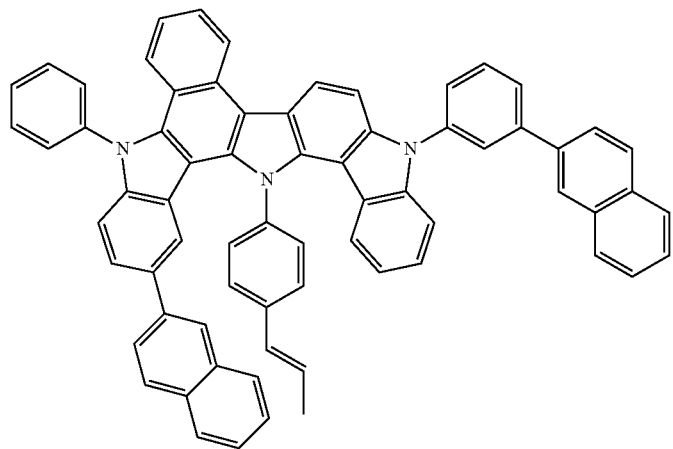
COMPOUND 95
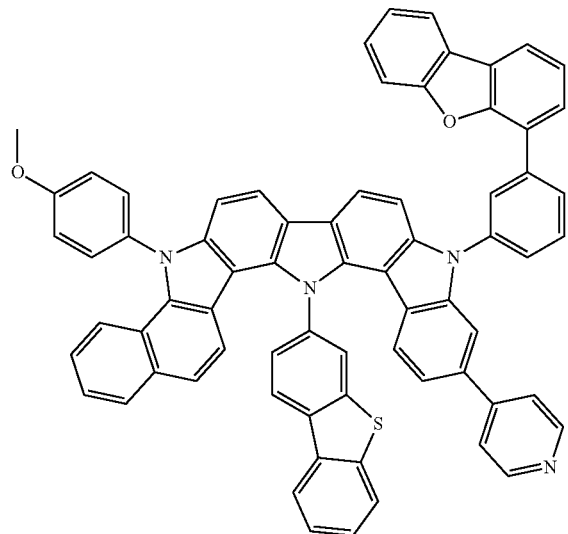

COMPOUND 96

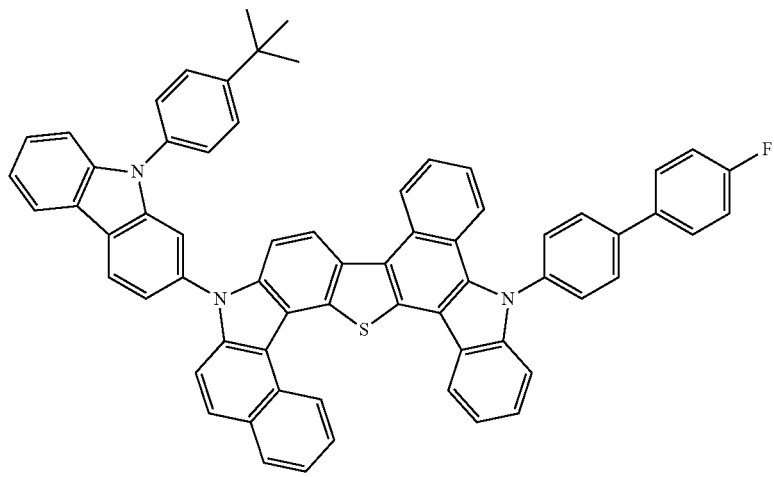

There exist various organic electronic devices which employ compounds including three or more 5-membered heterocycles, as described with reference to Formulas 1 to 3, as an organic material layer. The organic electronic devices in which compounds including three or more 5-membered heterocycles, as described with reference to Formulas 1 to 3 can be employed, may include, for example, an organic light emitting diode (OLED), an organic solar cell, an organic photo conductor (OPC) drum, an organic transistor (organic TFT), a photodiode, an organic laser, a laser diode, and the like.

As one example of the organic electronic devices in which compounds including three or more 5-membered heterocycles, as described with reference to Formulas 1 to 3, can be used, an organic light emitting diode (OLED) will be described below, but the present invention is not limited thereto. The above described compounds including three or more 5-membered heterocycles may be applied to various organic electronic devices.

In another embodiment of the present invention, there is provided an organic electronic device (organic electro-luminescence device) including a first electrode, a second electrode, and an organic material layer interposed between these electrodes, in which at least one of organic material layers includes the compounds represented by Formulas 1 to 3.

Figure 2:
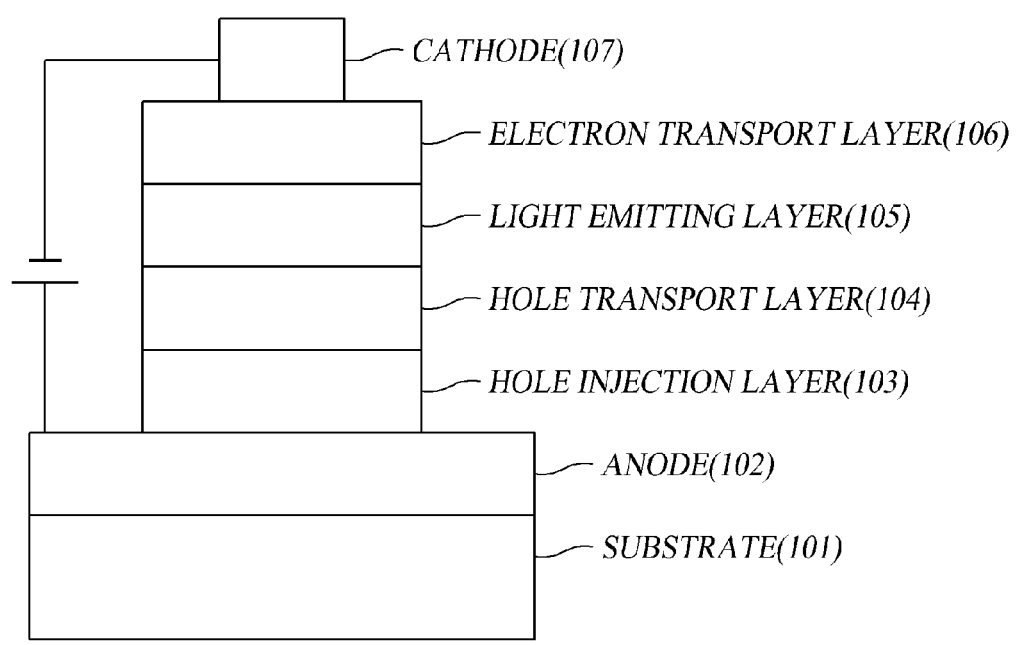
Figure 3:
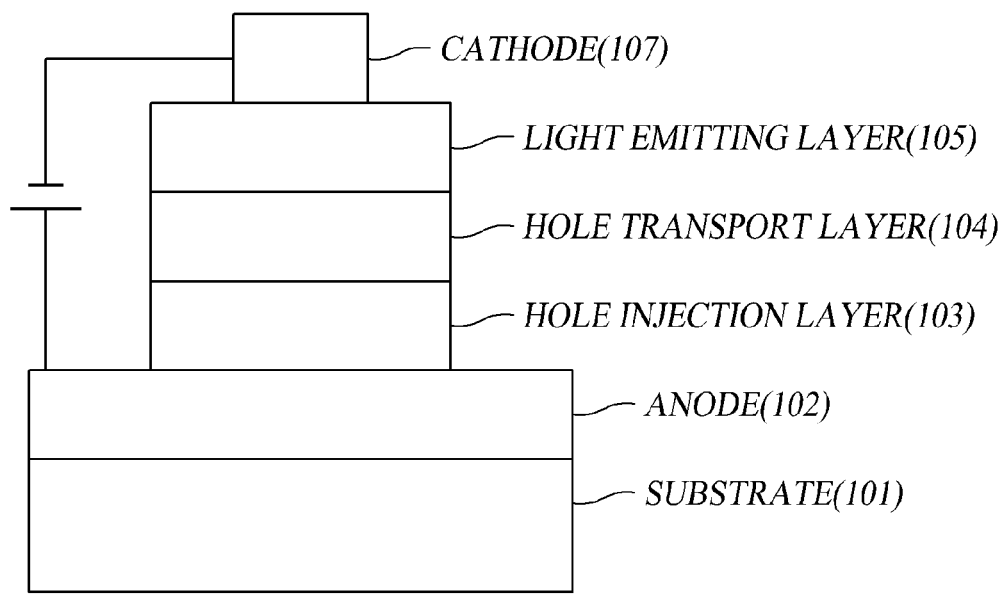
Figure 4:
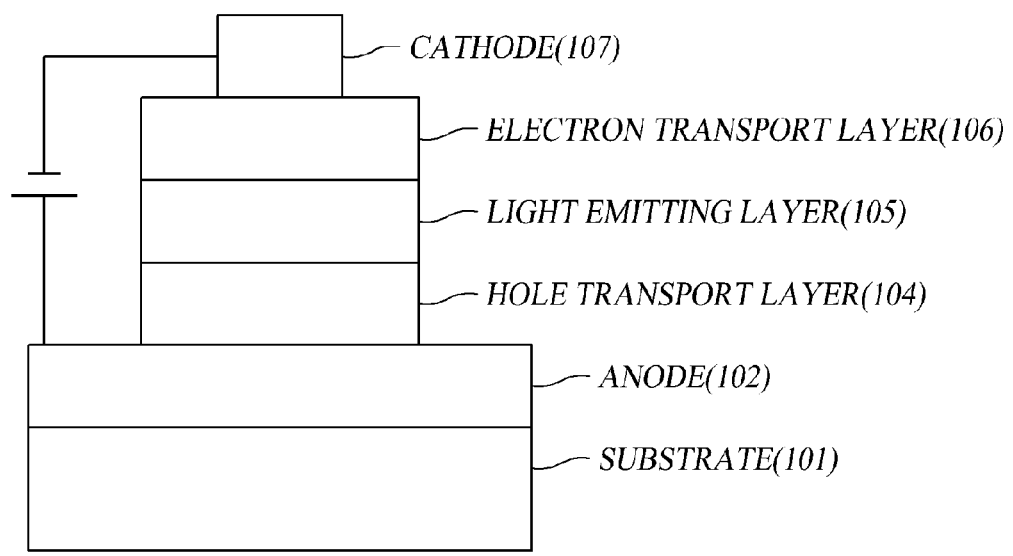
Figure 5:
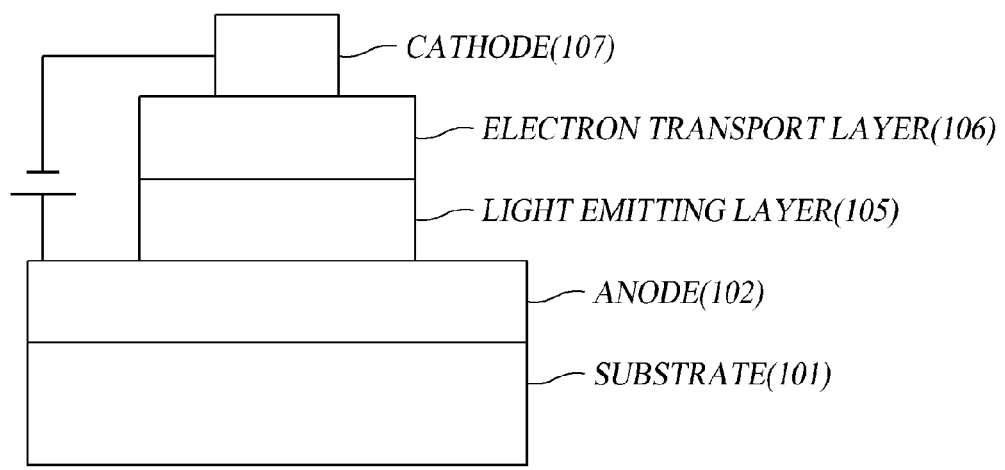
Figure 6:
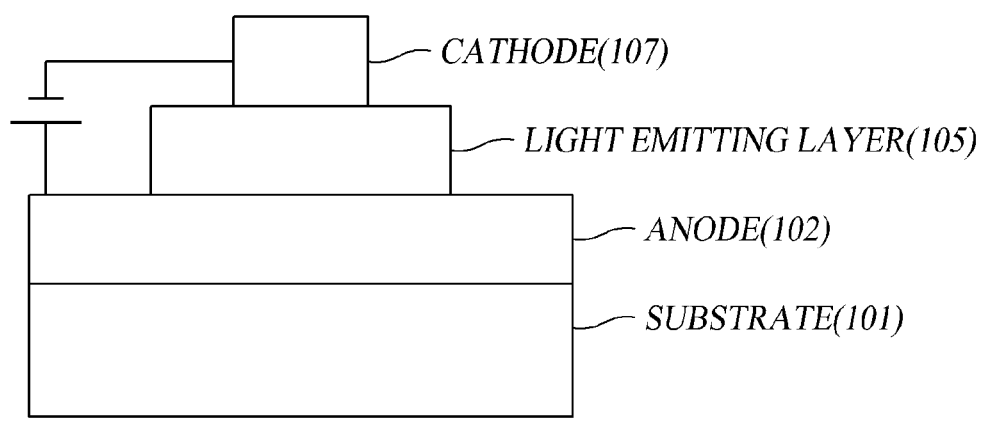

FIGS. 1 to 6 show examples of an organic electro-luminescence device which can employ a compound according to the present invention.

The organic electro-luminescence device according to another embodiment of the present invention may be manufactured by means of a manufacturing method and materials conventionally known in the art in such a manner that it can have a conventionally known structure, except that at least one of organic material layers including a hole injection layer, a hole transport layer, a light emitting layer, an electron transport layer, and an electron injection layer is formed in such a manner that it can include the compounds represented by Formulas 1 to 3.

The structures of the organic electro-luminescence device according to another embodiment of the present invention are shown in FIGS. 1 to 6, but the present invention is not limited to the structures. Herein, the reference numeral 101 indicates a substrate, 102 indicates an anode, 103 indicates a hole injection layer (HIL), 104 indicates a hole transport layer (HTL), 105 indicates a light emitting layer (EML), 106 indicates an electron injection layer (EIL), 107 indicates an electron transport layer (ETL), and 108 indicates a cathode. Although not shown, such an organic electro-luminescence device may further include a hole blocking layer (HBL) for blocking movement of holes, an electron blocking layer (EBL) for blocking movement of electrons, and a protective layer. The protective layer may be formed in such a manner that it, as an uppermost layer, can protect an organic material layer or a cathode.

Herein, the compound including three or more 5-membered heterocycles, as described with reference to Formulas 1 to 3, may be included in at least one of organic material layers including a hole injection layer, a hole transport layer, a light emitting layer, and an electron transport layer. Specifically, the compound including three or more 5-membered heterocycles, as described with reference to Formulas 1 to 3, may be substituted for at least one of a hole injection layer, a hole transport layer, a light emitting layer, an electron transport layer, an electron injection layer, a hole blocking layer, an electron blocking layer, and a protective layer, or may be used in combination with these layers. Of course, the compound may be used for not only one layer of the organic material layers but also two or more layers.

Especially, the compound including three or more 5-membered heterocycles, as described with reference to Formulas 1 to 3, may be used as a hole injection material, a hole transport material, a light emitting material, and/or an electron transport material appropriate for a fluorescent or phosphorescent device of all colors (such as red, green, blue, white, etc.), and especially is useful as a green phosphorescent host material.

For example, in manufacturing of the organic electro-luminescence device according to another embodiment of the present invention, a metal, a conductive metal oxide, or an alloy thereof is deposited on a substrate by means of PVD (physical vapor deposition) such as sputtering or e-beam evaporation so as to form an anode, and then an organic material layer including a hole injection layer, a hole transport layer, a light emitting layer, an electron transport layer, and an electron injection layer is formed thereon, and a material used as a cathode is deposited thereon.

Besides, on a substrate, a cathode material, an organic material layer, and an anode material may be sequentially deposited so as to provide an organic electronic device. The organic material layer may be formed in a multi-layered structure including a hole injection layer, a hole transport layer, a light emitting layer, an electron transport layer, and an electron injection layer, but the present invention is not limited thereto. It may be formed in a single layer structure. Further, the organic material layer may be manufactured with a smaller number of layers by using various polymer materials by means of a solvent process (e.g., spin coating, dip coating, doctor blading, screen printing, inkjet printing, or thermal transfer) instead of deposition.

In the organic electro-luminescence device according to another embodiment of the present invention, the organic material layer (e.g., a light emitting layer) may be formed by a soluble process of the above described compound including three or more 5-membered heterocycles.

The substrate is a support for the organic electro-luminescence device, and may employ a silicon wafer, a quartz or glass plate, a metallic plate, a plastic film or sheet.

On the substrate, an anode is positioned. Such an anode allows holes to be injected into a hole injection layer positioned thereon. As an anode material, a material having a high work function is preferably used so that injection of holes into an organic material layer can be smoothly carried out. Specific examples of an anode material used for the present invention may include: metals (such as vanadium, chromium, copper, zinc, gold) or alloys thereof; metallic oxides such as zinc oxide, indium oxide, indium tin oxide (ITO), indium zinc oxide (IZO); a metal-oxide combination such as ZnO:Al or $SnO_2$:Sb; and conductive polymers such as poly(3-methylthiophene), poly[3,4-(ethylene-1,2-dioxy)thiophene](PEDT), polypyrrole and polyaniline, but the present invention is not limited thereto.

On the anode, a hole injection layer is positioned. A material for such a hole injection layer is required to have a high efficiency for injecting holes from an anode, and to be able to efficiently transport the injected holes. For this, the material has a low ionization potential, a high transparency against visible light, and a high stability for holes.

As a hole injection material, a material into which holes can be well injected from an anode at a low voltage is used. Preferably, HOMO (highest occupied molecular orbital) of the hole injection material ranges from a work function of an anode material to HOMO of adjacent organic material layers. Specific examples of the hole injection material may include metal porphyrine-, oligothiophene-, and arylamine-based organic materials, hexanitrile hexaazatriphenylene- and quinacridone-based organic materials, perylene-based organic materials, and anthraquinone-, polyaniline-, and polythiophene-based conductive polymers, but the present invention is not limited thereto.

On the hole injection layer, a hole transport layer is positioned. Such a hole transport layer receives holes transferred from the hole injection layer and transfers them to an organic light emitting layer positioned thereon. Further, the hole transport layer has a high hole mobility and a high hole stability and performs a role of blocking electrons. Besides these general requirements, it requires heat-resistance against a device when applied to an automobile display, and thus is preferably made of a material having a glass transition temperature (Tg) of 70° C. or more. The examples of a material satisfying these conditions may include NPD (or NPB), spiro-arylamine-based compound, perylene-arylamine-based compound, azacycloheptatriene compound, bis(diphenylvinylphenyl)anthracene, silicongermaniumoxide compound, silicon-based arylamine compound, and the like.

On the hole transport layer, an organic light emitting layer is positioned. Such an organic light emitting layer is made of a material having a high quantum efficiency, in which holes and electrons which are injected from an anode and a cathode, respectively, are recombined so as to emit light. As a light emitting material, a material allowing holes and electrons transferred from a hole transport layer and an electron transport layer, respectively, to be combined so as to emit visible light is used. Preferably, a material having a high quantum efficiency against fluorescence or phosphorescence is used.

As a material or a compound satisfying these conditions, for a green color, Alq3 may be used, and for a blue color, Balq(8-hydroxyquinoline beryllium salt), DPVBi(4,4'-bis(2, 2-diphenylethenyl)-1,1'-biphenyl) based material, Spiro material, spiro-DPVBi(Spiro-4,4'-bis(2,2-diphenylethenyl)-1,1'-biphenyl), LiPBO (2-(2-benzoxazoyl)-phenol lithium salt), bis(diphenylvinylphenylvinyl)benzene, aluminum-quinoline metal complex, imidazole, thiazol and oxazole-metal complex, or the like may be used. In order to improve the luminous efficiency of a blue color, perylene, and BczVBi (3,3'[(1,1'-biphenyl)-4,4'-diyldi-2,1-ethenediyl]bis(9-ethyl)-9H-carbazole; DSA(distrylamine)) may be doped in a small amount. For a red color, a green light emitting material may be doped with DCJTB([2-(1,1-dimethylethyl)-6-[2-(2,3,6,7-tetrahydro-1,1,7,7-tetramethyl-1H,5H-benzo(ij)quinolizin-9-yl)ethenyl]-4H-pyran-4-ylidene]-propanedinitrile) in a small amount. When a process such as inkjet printing, roll coating, spin coating, is used to form a light emitting layer, polyphenylenevinylene (PPV)-based polymer or poly fluorene may be used for an organic light emitting layer.

On the organic light emitting layer, an electron transport layer is positioned. Such an electron transport layer requires a material which has a high efficiency for electrons injected from a cathode positioned thereon, and can efficiently transport the injected electrons. For this, a material having a high electron affinity, a high electron mobility, and a high electron stability is required. The examples of an electron transport material satisfying these conditions may include Al complex of 8-hydroxyquinoline; complex including $Alq_3$; organic radical compound; and hydroxyflavone-metal complex, but the present invention is not limited thereto.

On the electron transport layer, an electron injection layer is layered. The electron injection layer may be manufactured by using a metal complex compound (such as Balq, Alq3, Be(bq)2, Zn(BTZ)2, Zn(phq)2, PBD, spiro-PBD, TPBI, and Tf-6P) or a low molecular material including an aromatic compound having an imidazole ring or a boron compound. Herein, the electron injection layer may be formed in a thickness range of 100 Å to 300 Å.

On the electron injection layer, a cathode is positioned. Such a cathode performs a role of injecting electrons into the electron injection layer. As a material for the cathode, the same material as that used for an anode may be used. In order to achieve efficient electron injection, a metal having a low work function is more preferable. Especially, metals such as tin, magnesium, indium, calcium, sodium, lithium, aluminum, silver, or alloys thereof may be used. Further, a double-layered electrode (e.g., lithiumfluoride and aluminum, lithium oxide and aluminum, and strontium oxide and aluminum) with a thickness of 100 μm or less may be used.

As described above, the compound including three or more 5-membered heterocycles, as described with reference to Formulas 1 to 3, may be used as a hole injection material, a hole transport material, a light emitting material, an electron transport material and/or an electron injection material appropriate for a fluorescent or phosphorescent device of all colors (such as red, green, blue, white, etc.), and may be used as a host material for various colors of a phosphorescent dopant.

The organic electro-luminescence device according to the present invention may be manufactured in a front luminescent type, a rear luminescent type, or a both-side luminescent type according to its materials.

Meanwhile, the present invention provides a terminal which includes a display device and a control part for driving the display device, the display device including the above described organic electronic device. The terminal means a wired/wireless communication terminal which is currently used or will be used in the future. The above described terminal according to the present invention may be a mobile communication terminal such as a cellular phone, and may include all kinds of terminals such as a PDA, an electronic dictionary, a PMP, a remote control, a navigation unit, a game player, various kinds of TVs, and various kinds of computers.

EXAMPLE

Hereinafter, the present invention will be described more specifically with reference to Preparation Examples and Experimental Examples. However, the following examples are only for illustrative purposes and are not intended to limit the scope of the invention.

PREPARATION EXAMPLE

Hereinafter, Preparation Examples or Synthesis Examples of the compounds including three or more 5-membered heterocycles, represented by Formula 3, will be described. However, since there are many compounds including three or more 5-membered heterocycles, represented by Formula 3, one compound or two compounds from among the compounds will be exemplified. A person skilled in the art of the invention should realize that other compounds including three or more 5-membered heterocycles can be prepared through Preparation Examples as described below although they are not exemplified.

Step 1) Synthesis of Intermediate A

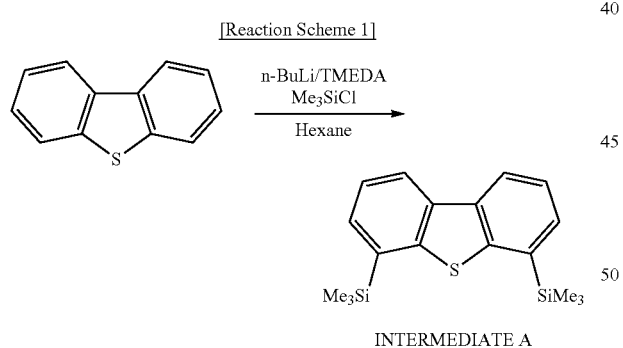

In a 250 mL round-bottom flask, N,N,N',N'-Tetramethylenediamine (TMEDA) was dissolved in anhydrous Hexane. At 0° C., n-BuLi (1.6 M in hexane) was slowly added thereto for 30 minutes, and the mixture was stirred for 30 minutes at room temperature. Dibenzothiophene diluted with Hexane was added thereto, and the resultant product was stirred at 60° C. for 2 hours. Then, the temperature of the product was lowered to −70° C., and chlorotrimethylsilane was added thereto, followed by stirring for 1 hour. After the completion of the reaction, the resultant product was extracted with Hexane, and washed with water.

From the extract, a small amount of water was removed by MgSO$_4$ (anhydrous), followed by vacuum-filtration. Then, the product obtained after concentration of an organic solvent was purified by column chromatography (solvent: Pentane) to give a required intermediate A (yield: 30%).

Step 2) Synthesis of Intermediate B

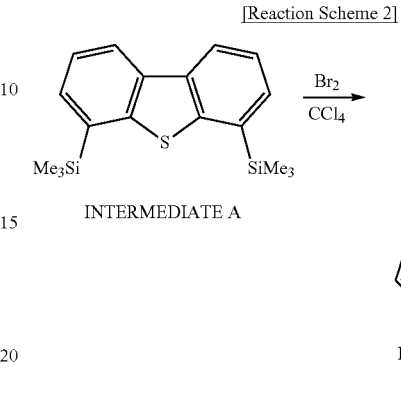

The intermediate A obtained from the step 1) was dissolved in Carbon tetrachloride. The temperature of the resultant product was lowered to −15° C., and Bromine was slowly added thereto. Then, the resultant product was stirred at 0° C. for 1 hour, and water was added thereto to quench the reaction. The organic layer was washed with Brine. Anhydrous MgSO$_4$ was used to remove water within the resultant product. After vacuum-filtration, the product obtained by concentration of an organic solvent was purified by column chromatography to give a required intermediate B (yield: 89%).

Step 3) Synthesis of Intermediate C

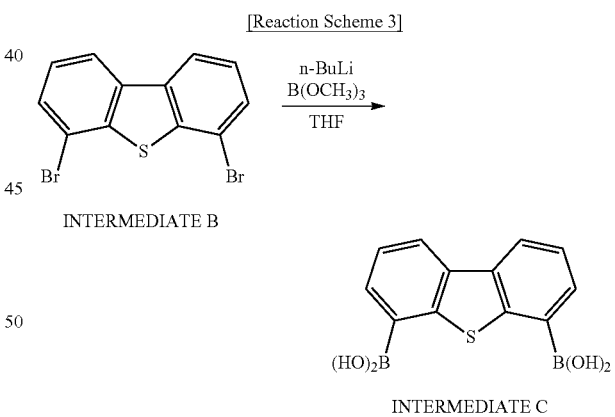

The intermediate B obtained from the step 2) was dissolved in anhydrous THF. The temperature of the resultant product was lowered to −78° C., and n-BuLi (1.6 M in Hexane) was slowly added thereto. Then, the resultant product was stirred at 0° C. for 1 hour. Then, the temperature of the resultant product was lowered to −78° C., and Trimethyl borate was added thereto, followed by stirring at room temperature for 12 hours. After the completion of the reaction, the resultant product was added with 2N HCl aqueous solution, stirred for minutes, and extracted with Ether. From the extract, a small amount of water was removed by anhydrous MgSO$_4$, followed by vacuum-filtration. Then, the product obtained after concentration of an organic solvent was purified by column chromatography to give a required intermediate C (yield: 70%).

Step 4) Synthesis of Intermediate D

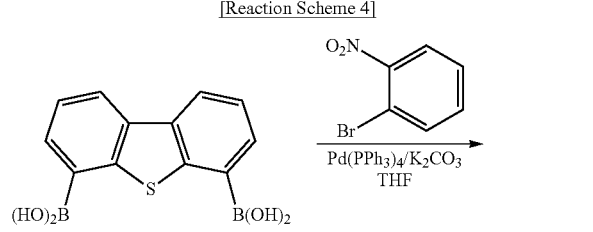

INTERMEDIATE D

The intermediate C obtained from the step 3), Pd(PPh$_3$)$_4$, and K$_2$CO$_3$ were dissolved in anhydrous THF and a small amount of water, followed by reflux for 24 hours. After the completion of the reaction, the resultant product was cooled to room temperature, extracted with CH$_2$Cl$_2$, and washed with water. From the extract, a small amount of water was removed by anhydrous MgSO$_4$, followed by vacuum-filtration. Then, the product obtained after concentration of an organic solvent was purified by column chromatography to give a required intermediate D (yield: 77%).

Step 5) Synthesis of Intermediate E

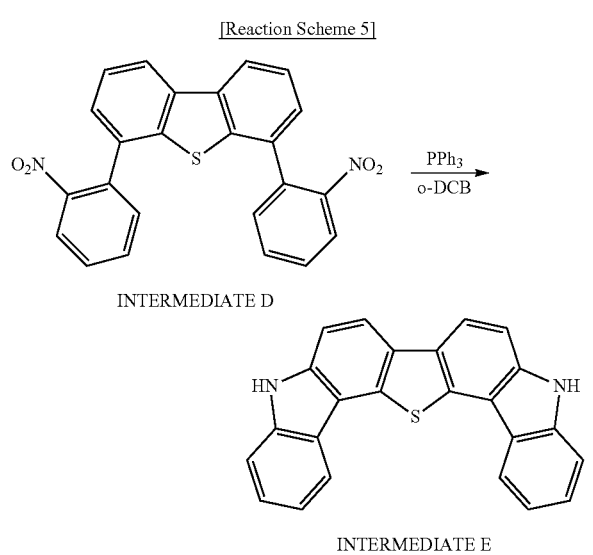

INTERMEDIATE E

The intermediate D obtained from the step 4) and triphenylphosphine were dissolved in o-dichlorobenzene, followed by reflux for 24 hours. After the completion of the reaction, the solvent was removed by vacuum distillation. Then, the concentrated product was purified by column chromatography to give a required intermediate E (yield: 57%).

SYNTHESIS EXAMPLE 1

Synthesis of Compound 1

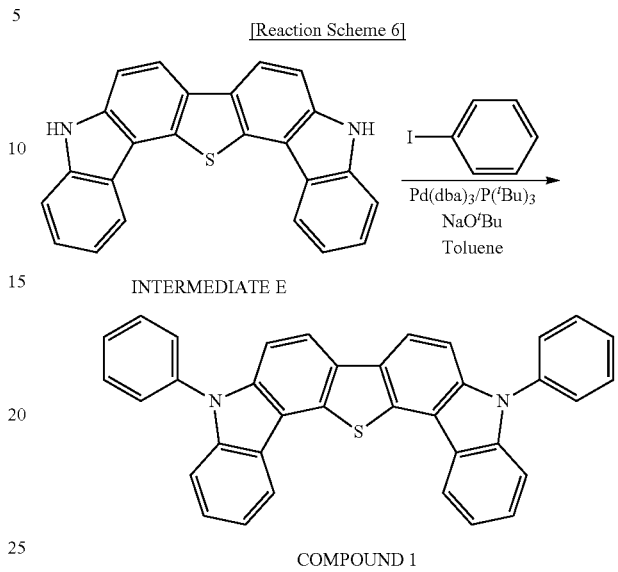

COMPOUND 1

The intermediate E synthesized from the step 5), Iodobenzene, Pd$_2$(dba)$_3$, P($^t$Bu)$_3$ and NaO$^t$Bu were dissolved in Toluene solvent, followed by stirring at 110° C. for 6 hours. After the completion of the reaction, the resultant product was cooled to room temperature, extracted with CH$_2$Cl$_2$, and washed with water. From the extract, a small amount of water was removed by anhydrous MgSO$_4$, followed by vacuum-filtration. Then, the product obtained after concentration of an organic solvent was purified by column chromatography to give a required compound 1 (yield: 65%).

SYNTHESIS EXAMPLE 2

Synthesis of Compound 10

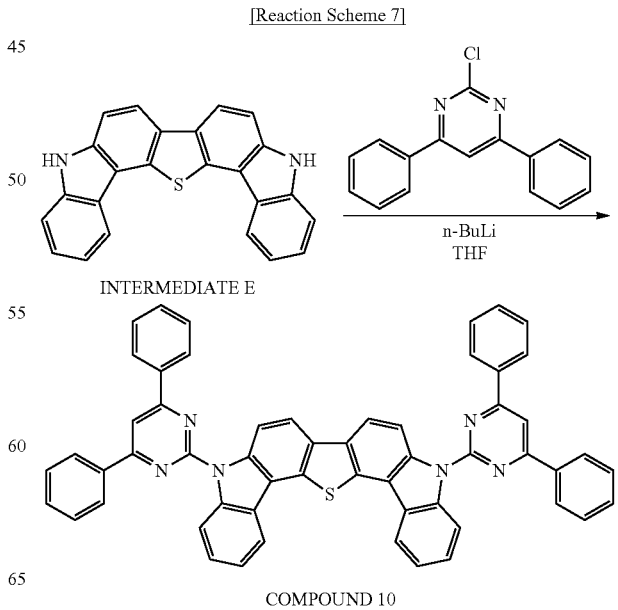

COMPOUND 10

The intermediate E synthesized from the step 5) was dissolved in anhydrous THF. The temperature of the resultant product was lowered to −78° C., and n-BuLi (1.6 M in Hexane) was slowly added thereto. Then, the resultant product was stirred at 0° C. for 1 hour. Then, the temperature of the resultant product was lowered to −78° C., and 2-Chloro-4,6-diphenylpyrimidine dissolved in anhydrous THF was slowly added thereto, followed by stirring at 60° C. for 12 hours. After the completion of the reaction, the resultant product was cooled to room temperature, extracted with $CH_2Cl_2$, and washed with water. From the extract, a small amount of water was removed by anhydrous $MgSO_4$, followed by vacuum-filtration. Then, the product obtained after concentration of an organic solvent was purified by column chromatography to give a required compound 10 (yield: 48%).

Step 6) Synthesis of Intermediate F

[Reaction Scheme 8]

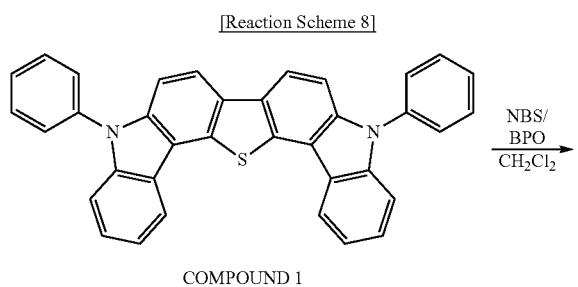

COMPOUND 1

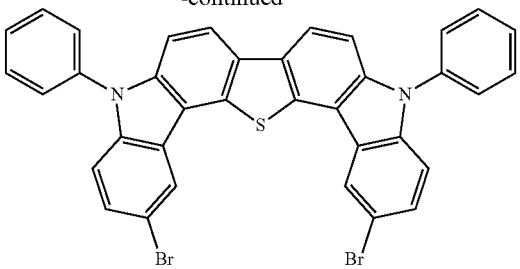

INTERMEDIATE F

The compound 1 obtained from Synthesis Example 1, NBS (N-bromosuccinimide), and BPO (benzoyl peroxide) were dissolved in $CH_2Cl_2$, followed by stirring at room temperature for 6 hours. After the completion of the reaction, the resultant product was added with a sodium bicarbonate aqueous solution, stirred for 30 minutes, and extracted with $CH_2Cl_2$. Anhydrous $MgSO_4$ was used to remove water within the resultant product. After vacuum-filtration, the product obtained by concentration of an organic solvent was purified by column chromatography to give a required intermediate F (yield: 77%).

SYNTHESIS EXAMPLE 3

Synthesis of Compound 27

[Reaction Scheme 9]

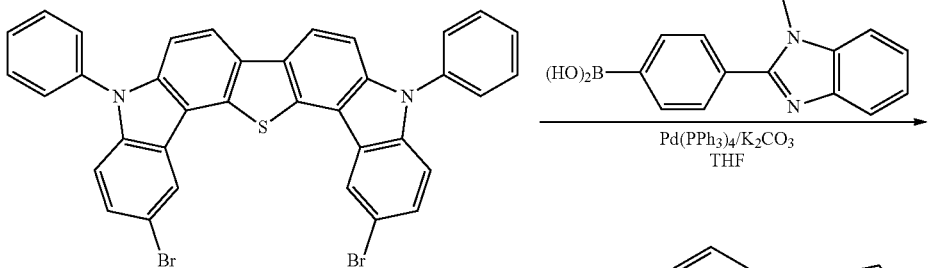

INTERMEDIATE F

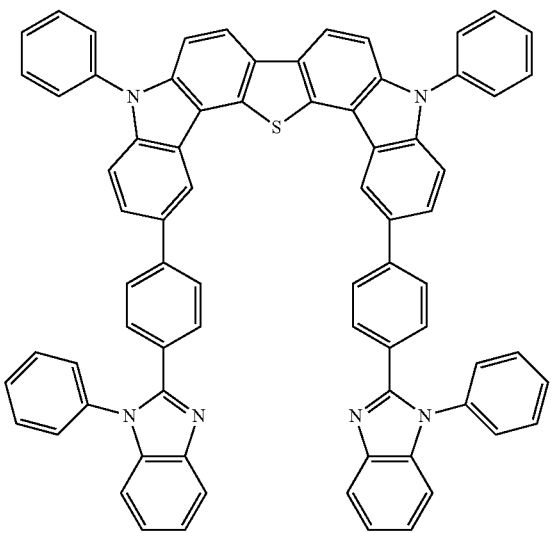

COMPOUND 27

The intermediate F obtained from the step 6), 4-(1-Phenyl-1H-benzo[d]imidazol-2-yl)phenylboronic acid, Pd(PPh₃)₄, and K₂CO₃ were dissolved in anhydrous THF and a small amount of water, followed by reflux for 24 hours. After the completion of the reaction, the resultant product was cooled to room temperature, extracted with CH₂Cl₂, and washed with water. From the extract, a small amount of water was removed by anhydrous MgSO₄, followed by vacuum-filtration. Then, the product obtained after concentration of an organic solvent was purified by column chromatography to give a required compound 27 (yield: 57%).

SYNTHESIS EXAMPLE 4

Synthesis of Compound 58

[Reaction Scheme 10]

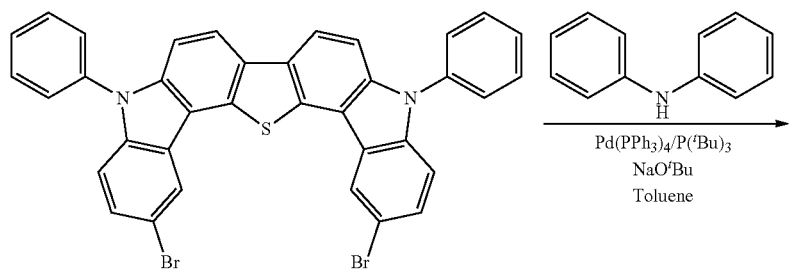

INTERMEDIATE F

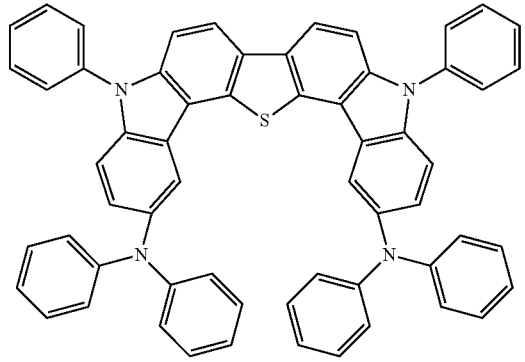

COMPOUND 58

The intermediate F obtained from the step 6), diphenylamine, Pd₂(dba)₃, P(tBu)₃ and NaOᵗBu were dissolved in Toluene solvent, followed by stirring at 110° C. for 9 hours. After the completion of the reaction, the resultant product was cooled to room temperature, extracted with CH₂Cl₂, and washed with water. From the extract, a small amount of water was removed by anhydrous MgSO₄, followed by vacuum-filtration. Then, the product obtained after concentration of an organic solvent was purified by column chromatography to give a required compound 58 (yield: 60%).

SYNTHESIS EXAMPLE 5

Synthesis of Compound 83

[Reaction Scheme 11]

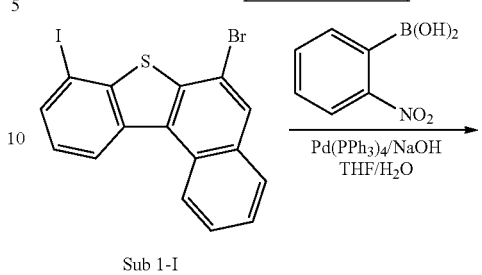

Sub 1-I

-continued

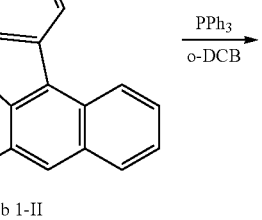

Sub 1-II

-continued

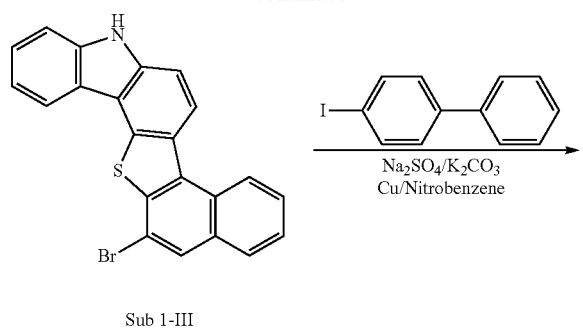

Sub 1-III

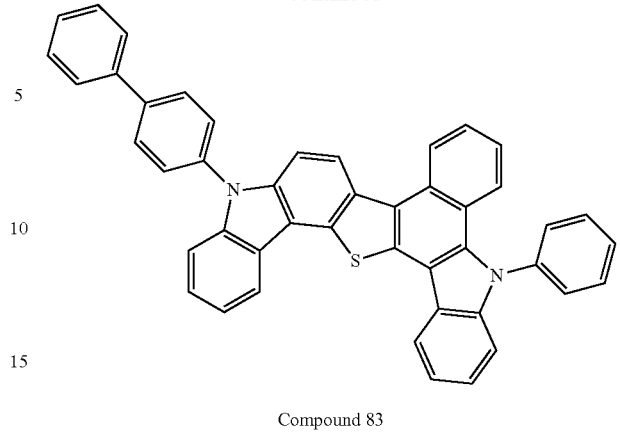

Compound 83

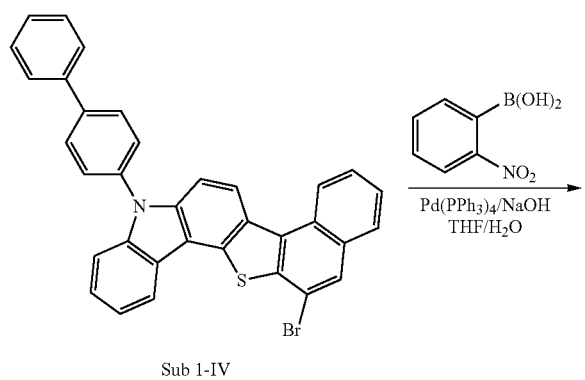

Sub 1-IV

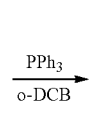

Sub 1-V

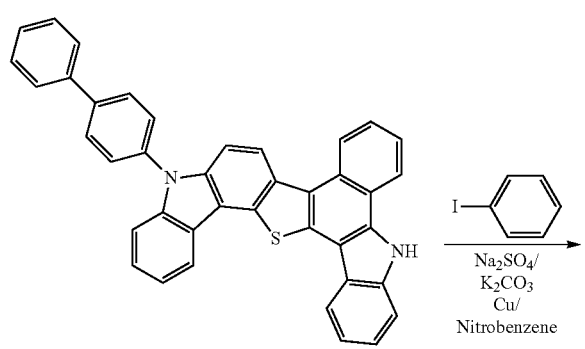

INTERMEDIATE G (1) Synthesis Method of Sub 1-II

In a round-bottom flask, Sub 1-I (308 g, 701.42 mmol), (2-nitrophenyl)boronic acid (117.1 g, 701.42 mmol), Pd(PPh3)$_4$ (24.32 g, 21.04 mmol), NaOH (84.17 g, 2104 mmol), THF (3086 ml), and water (1543 ml) were placed and heated to reflux at 80~90° C. Upon completion of the reaction, the reaction product was diluted with distilled water at room temperature and then extracted with $CH_2Cl_2$ and water. The extracted organic layer was dried with $MgSO_4$ and concentrated, and then the produced organic material was separated by a silica gel column and recrystallized to obtain 219.3 g of product (yield: 72).

(2) Synthesis Method of Sub 1-III

The obtained Sub 1-II (219 g, 504.25 mmol) was dissolved in o-dichlorobenzene (2017 ml) in a round bottom flask, and triphenylphosphine (396.8 g, 1512 mmol) was added to the reaction solution, followed by stirring at 200° C. Upon completion of the reaction, o-dichlorobenzene was removed by distillation, and the reaction product was extracted with $CH_2Cl_2$ and water. The extracted organic layer was dried with $MgSO_4$ and concentrated, and then the produced organic material was separated by a silica gel column and recrystallized to obtain 87.2 g of product (yield: 43%).

(3) Synthesis Method of Sub 1-IV

The obtained Sub 1-III (79 g, 196.36 mmol) was dissolved in nitrobenzene (981 ml) in a round bottom flask, and 4-iodo-1,1'-biphenyl (60.5 g, 216 mmol), $Na_2SO_4$ (27.9 g, 196.36 mmol), $K_2CO_3$ (27.1 g, 196.36 mmol), and Cu (3.7 g, 58.9 mmol) were added to the reaction solution, followed by stirring at 200° C. Upon completion of the reaction, nitrobenzene was removed by distillation, and the reaction product was extracted with $CH_2Cl_2$ and water. The extracted organic layer was dried with $MgSO_4$ and concentrated, and then the produced organic material was separated by a silica gel column and recrystallized to obtain 48.9 g of product (yield: 45%).

(4) Synthesis Method of Sub 1-V

In a round-bottom flask, Sub 1-IV (48 g, 86.6 mmol), (2-nitrophenyl)boronic acid (14.45 g, 86.6 mmol), Pd(PPh$_3$)$_4$ (3.0 g, 2.6 mmol), NaOH (10.39 g, 259.7 mmol), THF (380 ml), and water (190 ml) were placed and heated to reflux at 80~90° C. Upon completion of the reaction, the reaction product was diluted with distilled water at room temperature and then extracted with $CH_2Cl_2$ and water. The extracted organic layer was dried with $MgSO_4$ and concentrated, and then the produced organic material was separated by a silica gel column and recrystallized to obtain 35.12 g of product (yield: 68%)

(5) Synthesis Method of Intermediate G

The obtained Sub 1-V (31 g, 51.95 mmol) was dissolved in o-dichlorobenzene (208 ml) in a round bottom flask, and triphenylphosphine (40.9 g, 155.86 mmol) was added to the reaction solution, followed by stirring at 200° C. Upon completion of the reaction, o-dichlorobenzene was removed by distillation, and the reaction product was extracted with $CH_2Cl_2$ and water. The extracted organic layer was dried with $MgSO_4$ and concentrated, and then the produced organic material was separated by a silica gel column and recrystallized to obtain 13.2 g of product (yield: 45%).

(6) Synthesis Method of Compound 83

The obtained Intermediate G (13.2 g, 23.38 mmol) was dissolved in nitrobenzene (117 ml) in a round bottom flask, and iodo-phenyl (5.2 g, 25.71 mmol), $Na_2SO_4$ (3.3 g, 23.38 mmol), $K_2CO_3$ (3.2 g, 23.38 mmol), and Cu (0.4 g, 7.013 mmol) were added to the reaction solution, followed by stirring at 200° C. Upon completion of the reaction, nitrobenzene was removed by distillation, and the reaction product was extracted with $CH_2Cl_2$ and water. The extracted organic layer was dried with $MgSO_4$ and concentrated, and then the produced organic material was separated by a silica gel column and recrystallized to obtain 7.19 g of product (yield: 48%).

SYNTHESIS EXAMPLE 6

Synthesis of Compound 84

[Reaction Scheme 12]

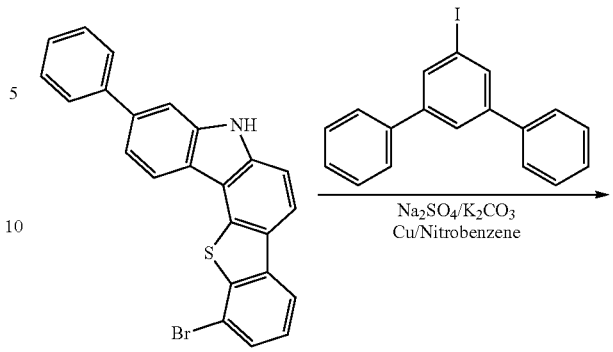

Sub 2-III

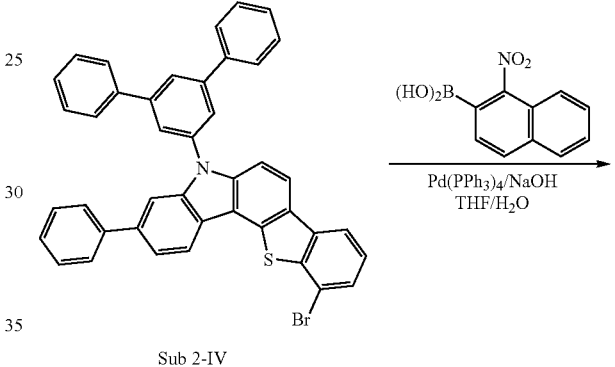

Sub 2-IV

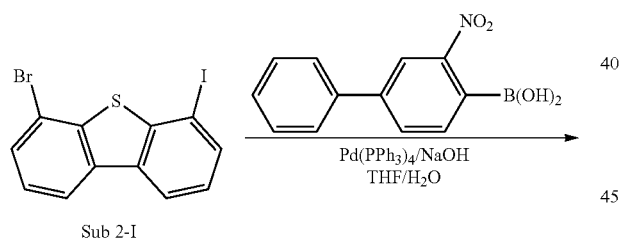

Sub 2-I

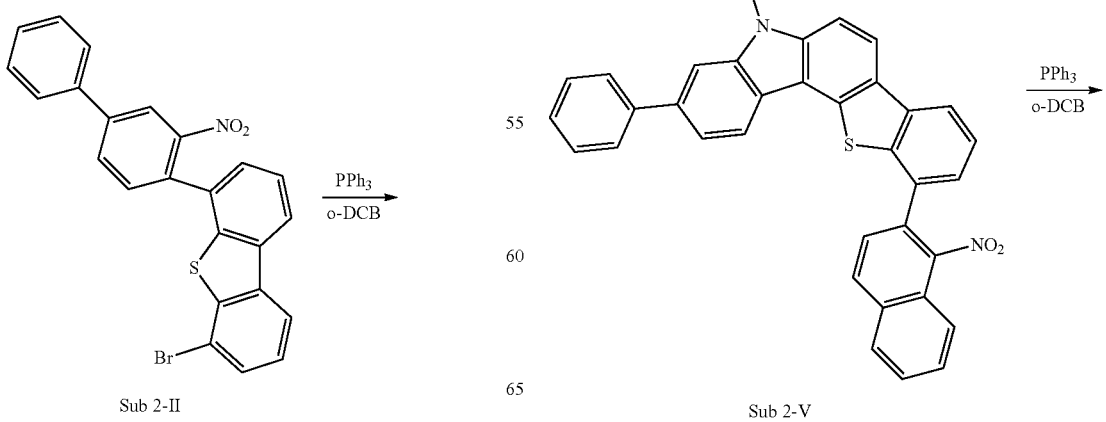

Sub 2-II

Sub 2-V

-continued

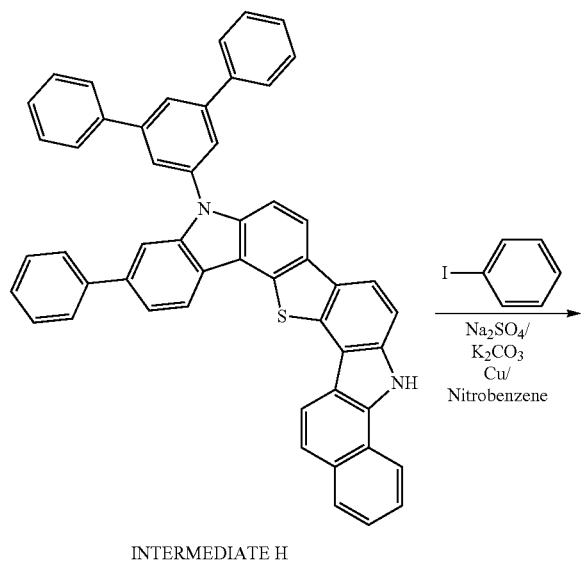

INTERMEDIATE H

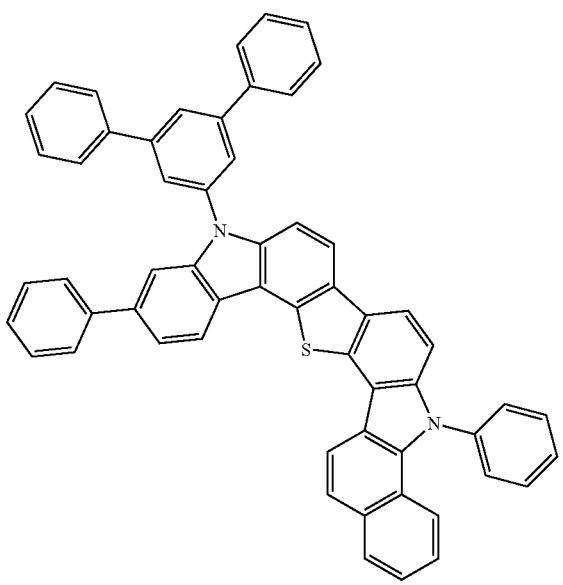

Compound 84

(1) Synthesis Method of Sub 2-II

Using Sub 2-I (260 g, 668.3 mmol), (3-nitro-[1,1'-biphenyl]-4-yl)boronic acid (162.41 g, 668.3 mol), Pd(PPh$_3$)$_4$ (23.17 g, 20.05 mmol), NaOH (80.2 g, 2004.9 mmol), THF (2940 ml), and water (1470 ml), the same procedure as described in the synthesis method of Sub 1-II was carried out to obtain 215.35 g of product (yield: 70%).

(2) Synthesis Method of Sub 2-III

Using Sub 2-II (190 g, 412.7 mmol), o-dichlorobenzene (1651 ml), and triphenylphosphine (324.8 g, 1238.2 mmol), the same procedure as described in the synthesis method of Sub 1-III was carried out to obtain 83.09 g of product (yield: 47%).

(3) Synthesis Method of Sub 2-IV

Using Sub 1-III (83 g, 193.77 mmol), nitrobenzene (969 ml), 5'-iodo-1,1':3',1''-terphenyl (75.9 g, 213.15 mmol), Na$_2$SO$_4$ (27.5 g, 193.77 mmol), K$_2$CO$_3$ (26.8 g, 193.78 mmol), and Cu (3.7 g, 58.13 mmol), the same procedure as described in the synthesis method of Sub 1-IV was carried out to obtain 62.35 g of product (yield: 49%).

(4) Synthesis Method of Sub 2-V

Using Sub 2-IV (62 g, 94.42 mmol), (1-nitronaphthalen-2-yl)boronic acid (20.49 g, 94.42 mmol), Pd(PPh$_3$)$_4$ (3.27 g, 2.83 mmol), NaOH (11.33 g, 283.27 mmol), THF (415 ml), and water (208 ml), the same procedure as described in the synthesis method of Sub 2-V was carried out to obtain 36.06 g of product (yield: 51%).

(5) Synthesis Method of Intermediate H

Using the obtained Sub 2-V (36 g, 48.07 mmol), o-dichlorobenzene (192 ml), and triphenylphosphine (37.8 g, 144 mmol), the same procedure as described in the synthesis method of Intermediate G was carried out to obtain 16.89 g of product (yield: 49%).

(6) Synthesis Method of Compound 84

The obtained Intermediate H (16.8 g, 23.44 mmol) was dissolved in nitrobenzene (117 ml) in a round bottom flask, and iodo-phenyl (5.3 g, 25.78 mmol), Na$_2$SO$_4$ (3.3 g, 23.44 mmol), K$_2$CO$_3$ (3.2 g, 23.44 mmol), and Cu (0.4 g, 7.03 mmol) were added to the reaction solution, followed by stirring at 200° C. Upon completion of the reaction, nitrobenzene was removed by distillation, and the reaction product was extracted with CH$_2$Cl$_2$ and water. The extracted organic layer was dried with MgSO$_4$ and concentrated, and then the produced organic material was separated by a silica gel column and recrystallized to obtain 8.18 g of product (yield: 44%).

SYNTHESIS EXAMPLE 7

Synthesis of Compound 85

[Reaction Scheme 13]

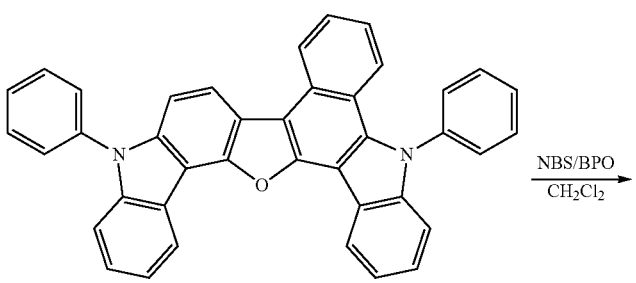

Compound 82

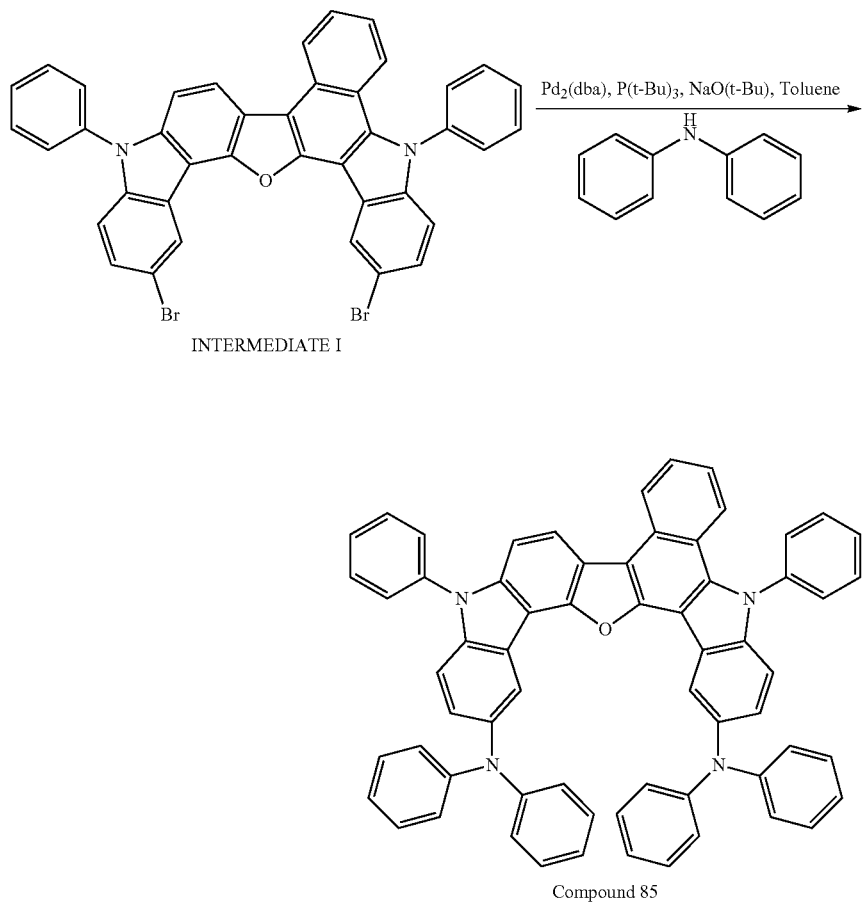

INTERMEDIATE I

Compound 85

(1) Synthesis Method of Intermediate I

In a round-bottom flask, compound 82 (30 g, 54.68 mmol), NBS (20.4 g, 114.83 mmol) and BPO (1.3 g, 5.47 mmol) were placed and $CH_2Cl_2$ (164 ml) as a solvent were added to the reaction solution, followed by stirring at room temperature for 5 hrs. Upon completion of the reaction, the reaction product was diluted with dichrolomethane as a solvent and then extracted. The extracted solution was dried with $MgSO_4$ and vacuum-dried, and then crude product was obtained. The obtained crude product was recrystallized with diethylether and n-hexane and then separated by a silica gel column to obtain 28.2 g of intermediate I (yield: 73%).

(2) Synthesis Method of Compound 85

In a round-bottom flask, intermaeiate I (2.4 g, 14.01 mmol), diphenylamine (9 g, 12.74 mmol), $Pd_2(dba)_3$ (1.2 g, 1.27 mmol), P(t-Bu)3 (0.5 g, 2.55 mmol), NaO(t-Bu) (6.1 g, 63.7 mmol), and Toluene (134 mL) were placed and heated to reflux at 110° C. for 3 hrs. Upon completion of the reaction, the reaction product was diluted with dichrolomethane as a solvent and then extracted. Upon completion of the reaction, the reaction product was diluted with distilled water at room temperature and then extracted with methylene chloride and water. The extracted organic layer was dried with $MgSO_4$ and concentrated, and then the produced organic material was dissolved in toluene and separated by a silica filter. Upon completion of the filter, the solution was concentrated, and recrystallized with toluene and acetone to obtain 7.43 g of product (yield: 66%).

SYNTHESIS EXAMPLE 8

Synthesis of Compound 89

[Reaction Scheme 14]

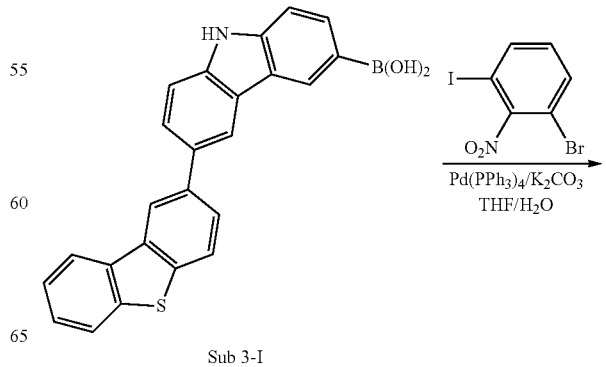

Sub 3-I

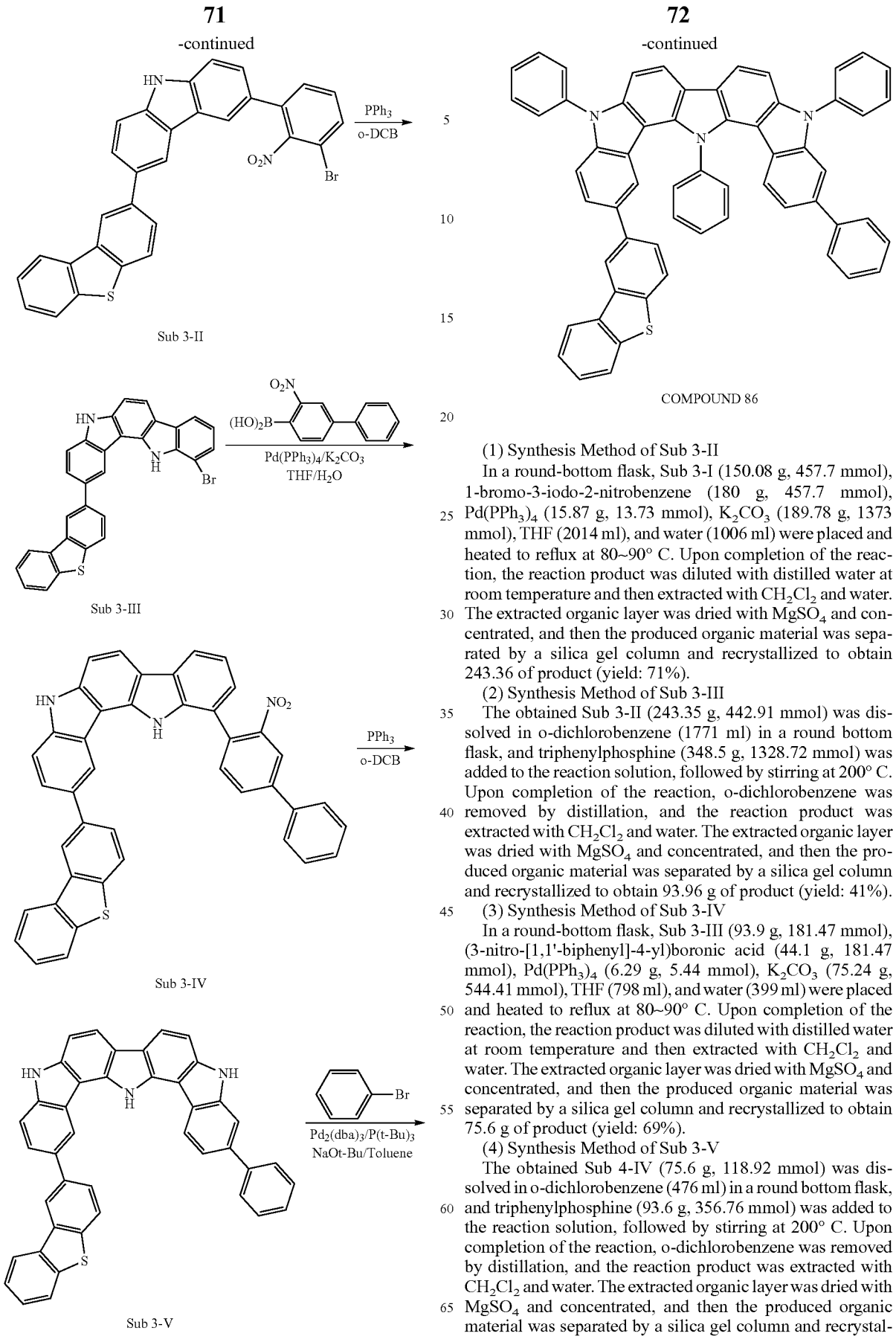

COMPOUND 86

(1) Synthesis Method of Sub 3-II

In a round-bottom flask, Sub 3-I (150.08 g, 457.7 mmol), 1-bromo-3-iodo-2-nitrobenzene (180 g, 457.7 mmol), Pd(PPh$_3$)$_4$ (15.87 g, 13.73 mmol), K$_2$CO$_3$ (189.78 g, 1373 mmol), THF (2014 ml), and water (1006 ml) were placed and heated to reflux at 80~90° C. Upon completion of the reaction, the reaction product was diluted with distilled water at room temperature and then extracted with CH$_2$Cl$_2$ and water. The extracted organic layer was dried with MgSO$_4$ and concentrated, and then the produced organic material was separated by a silica gel column and recrystallized to obtain 243.36 of product (yield: 71%).

(2) Synthesis Method of Sub 3-III

The obtained Sub 3-II (243.35 g, 442.91 mmol) was dissolved in o-dichlorobenzene (1771 ml) in a round bottom flask, and triphenylphosphine (348.5 g, 1328.72 mmol) was added to the reaction solution, followed by stirring at 200° C. Upon completion of the reaction, o-dichlorobenzene was removed by distillation, and the reaction product was extracted with CH$_2$Cl$_2$ and water. The extracted organic layer was dried with MgSO$_4$ and concentrated, and then the produced organic material was separated by a silica gel column and recrystallized to obtain 93.96 g of product (yield: 41%).

(3) Synthesis Method of Sub 3-IV

In a round-bottom flask, Sub 3-III (93.9 g, 181.47 mmol), (3-nitro-[1,1'-biphenyl]-4-yl)boronic acid (44.1 g, 181.47 mmol), Pd(PPh$_3$)$_4$ (6.29 g, 5.44 mmol), K$_2$CO$_3$ (75.24 g, 544.41 mmol), THF (798 ml), and water (399 ml) were placed and heated to reflux at 80~90° C. Upon completion of the reaction, the reaction product was diluted with distilled water at room temperature and then extracted with CH$_2$Cl$_2$ and water. The extracted organic layer was dried with MgSO$_4$ and concentrated, and then the produced organic material was separated by a silica gel column and recrystallized to obtain 75.6 g of product (yield: 69%).

(4) Synthesis Method of Sub 3-V

The obtained Sub 4-IV (75.6 g, 118.92 mmol) was dissolved in o-dichlorobenzene (476 ml) in a round bottom flask, and triphenylphosphine (93.6 g, 356.76 mmol) was added to the reaction solution, followed by stirring at 200° C. Upon completion of the reaction, o-dichlorobenzene was removed by distillation, and the reaction product was extracted with CH$_2$Cl$_2$ and water. The extracted organic layer was dried with MgSO$_4$ and concentrated, and then the produced organic material was separated by a silica gel column and recrystallized to obtain 30.87 g of product (yield: 43%).

(5) Synthesis Method of Compound 86

In a round-bottom flask, Sub 3-V (30.8 g, 51.02 mmol), bromobenzene (24.8 g, 158.15 mmol), Pd$_2$(dba)$_3$ (2.8 g, 3.06 mmol), P(t-Bu)$_3$ (3.1 g, 15.31 mmol), NaO(t-Bu) (34.3 g, 357.11 mmol), and Toluene (536 mL) were placed and heated to reflux at 110° C. for 3 hrs. Upon completion of the reaction, the reaction product was diluted with dichrolomethane as a solvent and then extracted. Upon completion of the reaction, the reaction product was diluted with distilled water at room temperature and then extracted with methylene chloride and water. The extracted organic layer was dried with MgSO$_4$ and concentrated, and then the produced organic material was dissolved in toluene and separated by a silica filter. Upon completion of the filter, the solution was concentrated, and recrystallized with toluene and acetone to obtain 28.44 g of product (yield: 67%).

SYNTHESIS EXAMPLE 9

Synthesis of Compound 89

[Reaction Scheme 15]

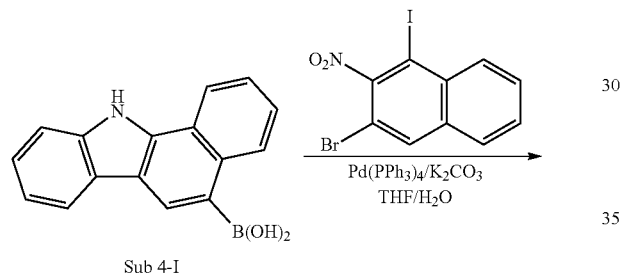

Sub 4-I

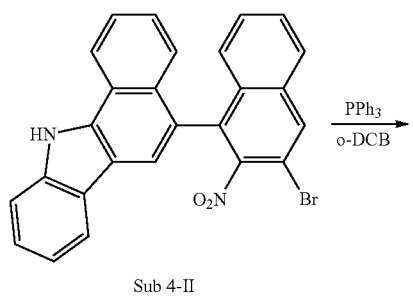

Sub 4-II

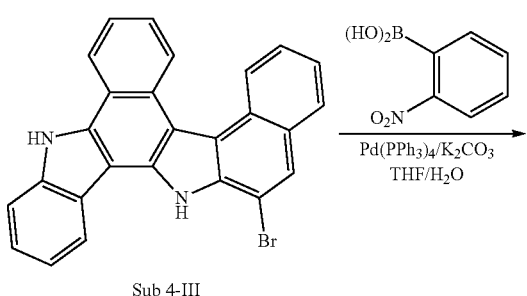

Sub 4-III

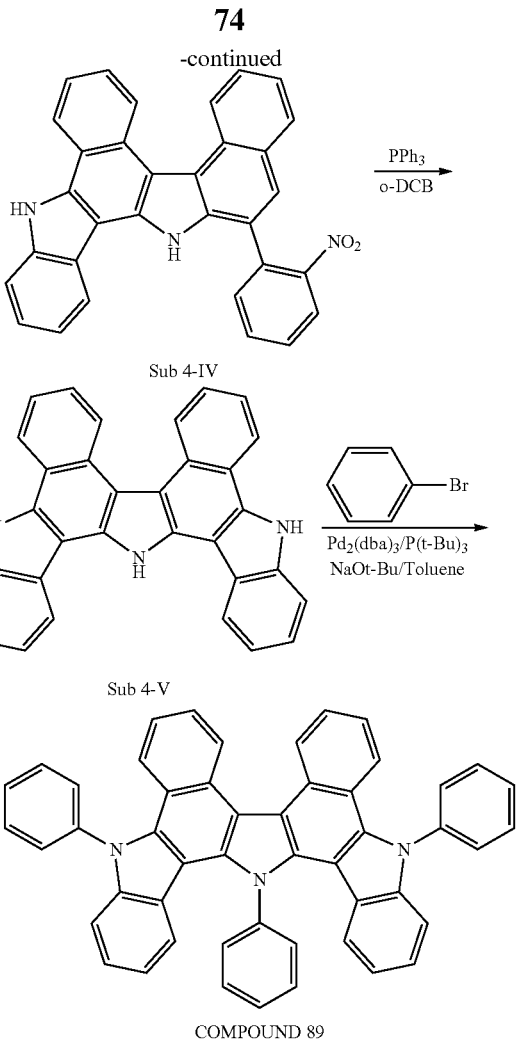

COMPOUND 89

(1) Synthesis Method of Sub 4-II

In a round-bottom flask, Sub 4-I (180 g, 689.44 mmol), 3-bromo-1-iodo-2-nitronaphthalene (260.6 g, 689.44 mmol), Pd(PPh$_3$)$_4$ (23.9 g, 20.68 mmol), K$_2$CO$_3$ (285.9 g, 2068.33 mmol), THF (3034 ml), and water (1517 ml) were placed and heated to reflux at 80~90° C. Upon completion of the reaction, the reaction product was diluted with distilled water at room temperature and then extracted with CH$_2$Cl$_2$ and water. The extracted organic layer was dried with MgSO$_4$ and concentrated, and then the produced organic material was separated by a silica gel column and recrystallized to obtain 238.42 of product (yield: 74%).

(2) Synthesis Method of Sub 4-III

The obtained Sub 4-II (238 g, 509.3 mmol) was dissolved in o-dichlorobenzene (2037 ml) in a round bottom flask, and triphenylphosphine (400.8 g, 1527.89 mmol) was added to the reaction solution, followed by stirring at 200° C. Upon completion of the reaction, o-dichlorobenzene was removed by distillation, and the reaction product was extracted with CH$_2$Cl$_2$ and water. The extracted organic layer was dried with MgSO$_4$ and concentrated, and then the produced organic material was separated by a silica gel column and recrystallized to obtain 88.68 g of product (yield: 40%).

(3) Synthesis Method of Sub 4-IV

In a round-bottom flask, Sub 4-III (88.3 g, 233.65 mmol), (2-nitrophenyl)boronic acid (61 g, 233.65 mmol), Pd(PPh$_3$)$_4$ (8.1 g, 7.01 mmol), K$_2$CO$_3$ (96.9 g, 700.94 mmol), THF (1028 ml), and water (514 ml) were placed and heated to reflux at 80~90° C. Upon completion of the reaction, the reaction product was diluted with distilled water at room temperature and then extracted with CH₂Cl₂ and water. The extracted organic layer was dried with MgSO₄ and concentrated, and then the produced organic material was separated by a silica gel column and recrystallized to obtain 82.98 g of product (yield: 76%).

(4) Synthesis Method of Sub 4-V

The obtained Sub 4-IV (82 g, 171.72 mmol) was dissolved in o-dichlorobenzene (687 ml) in a round bottom flask, and triphenylphosphine (135.1 g, 515.17 mmol) was added to the reaction solution, followed by stirring at 200° C. Upon completion of the reaction, o-dichlorobenzene was removed by distillation, and the reaction product was extracted with CH₂Cl₂ and water. The extracted organic layer was dried with MgSO₄ and concentrated, and then the produced organic material was separated by a silica gel column and recrystallized to obtain 33.66 g of product (yield: 44%).

(5) Synthesis Method of COMPOUND 89

In a round-bottom flask, Sub 4-V (33.5 g, 75.2 mmol), bromobenzene (36.6 g, 233.104 mmol), Pd₂(dba)₃ (4.1 g, 4.51 mmol), P(t-Bu)₃ (4.6 g, 22.56 mmol), NaO(t-Bu) (50.6 g, 526.36 mmol), and Toluene (789 mL) were placed and heated to reflux at 110° C. for 3 hrs. Upon completion of the reaction, the reaction product was diluted with dichrolomethane as a solvent and then extracted. Upon completion of the reaction, the reaction product was diluted with distilled water at room temperature and then extracted with methylene chloride and water. The extracted organic layer was dried with MgSO₄ and concentrated, and then the produced organic material was dissolved in toluene and separated by a silica filter. Upon completion of the filter, the solution was concentrated, and recrystallized with toluene and acetone to obtain 31.41 g of product (yield: 62%).

SYNTHESIS EXAMPLE 10

Synthesis of Compound 92

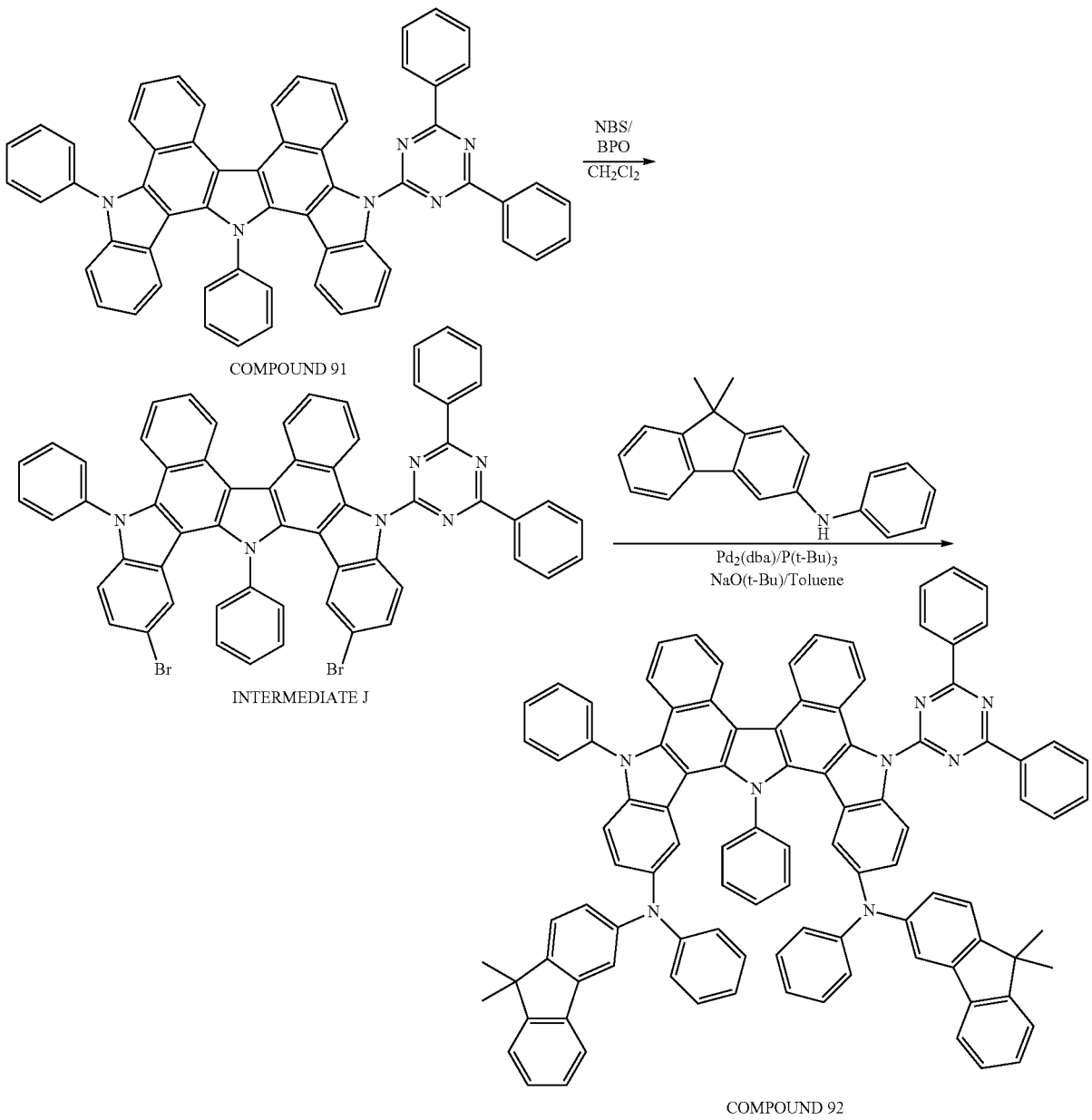

[Reaction Scheme 15]

(1) Synthesis Method of Intermediate J

In a round-bottom flask, compound 91 (30 g, 36.19 mmol), NBS (13.5 g, 76 mmol) and BPO (0.9 g, 3.62 mmol) were placed and $CH_2Cl_2$(109 ml) as a solvent were added to the reaction solution, followed by stirring at room temperature for 5 hrs. Upon completion of the reaction, the reaction product was diluted with dichrolomethane as a solvent and then extracted. The extracted solution was dried with $MgSO_4$ and vacuum-dried, and then crude product was obtained. The obtained crude product was recrystallized with diethylether and n-hexane and then separated by a silica gel column to obtain 24.64 g of intermediate J (yield: 69%)

(2) Synthesis Method of Compound 92

In a round-bottom flask, intermaeiate J (15 g, 15.2 mmol), 9,9-dimethyl-N-phenyl-9H-fluoren-3-amine (9.1 g, 31.92 mmol), $Pd_2(dba)_3$ (0.6 g, 0.608 mmol), P(t-Bu)$_3$ (0.6 g, 3.04 mmol), NaO(t-Bu) (8.8 g, 91.21 mmol), and Toluene (160 mL) were placed and heated to reflux at 110□ for 3 hrs. Upon completion of the reaction, the reaction product was diluted with dichrolomethane as a solvent and then extracted. Upon completion of the reaction, the reaction product was diluted with distilled water at room temperature and then extracted with methylene chloride and water. The extracted organic layer was dried with $MgSO_4$ and concentrated, and then the produced organic material was dissolved in toluene and separated by a silica filter. Upon completion of the filter, the solution was concentrated, and recrystallized with toluene and acetone to obtain 13.37 g of product (yield: 63%).

Fabrication Test of Organic Electro-luminescence Device

An organic electro-luminescence device was manufactured according to a conventional method by using each of compounds 1, 10, 27, and 58 obtained by synthesis as a light emitting host material for a light emitting layer. First, on an ITO layer (anode) formed on a glass substrate, a copper phthalocyanine (hereinafter, referred to as CuPc) film as a hole injection layer was vacuum-deposited with a thickness of 10 nm.

Then, on this film, 4,4-bis[N-(1-naphthyl)-N-phenylamino]biphenyl (hereinafter, referred to as a-NPD) as a hole transport compound was vacuum-deposited with a thickness of 30 nm so as to form a hole transport layer. After the hole transport layer was formed, each of the compounds 1, 10, 27 and 58 as a phosphorescence host material was deposited on the hole transport layer so as to form a light emitting layer.

At the same time, as a phosphorescent Ir metal complex dopant, tris(2-phenylpyridine)iridium (hereinafter, referred to as Ir(ppy)$_3$) was added. Herein, in the light emitting layer, the concentration of Ir(ppy)$_3$ was 5 wt %. As a hole blocking layer, (1,1-bisphenyl)-4-olato)bis(2-methyl-8-quinolinolato) aluminum (hereinafter, referred to as BAlq) was vacuum-deposited with a thickness of 10 nm, and then as an electron injection layer, tris(8-quinolinol)aluminum (hereinafter, referred to as Alg$_3$) was film-formed with a thickness of 40 nm. Then, LiF (alkali-metal halide) was deposited with a thickness of 0.2 nm, and Al was deposited with a thickness of 150 nm. The Al/LiF was used as a cathode while the organic electro-luminescence device was fabricated.

COMPARISON EXAMPLE 1

For comparison, instead of the inventive compound, a compound (hereinafter, referred to as CBP) represented by Formula 4 was used as a light emitting host material so as to fabricate an organic electro-luminescence device with the same structure as that of Test Example.

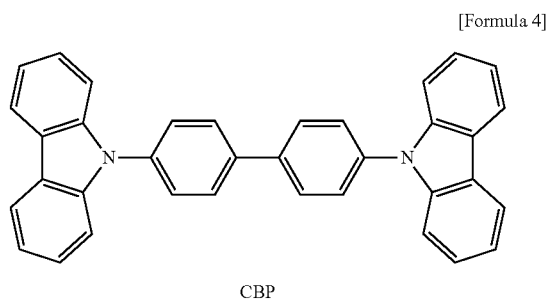 [SMILES: c1ccc2c(c1)c1ccccc1n2-c1ccc(-c2ccc(-n3c4ccccc4c4ccccc43)cc2)cc1 ; "CBP"]

[Formula 4]

CBP

TABLE 1

| | Host material of light emitting layer | Voltage (V) | current density (mA/cm$^2$) | luminance (cd/m$^2$) | luminous efficiency (cd/A) | chromaticity co-ordinates (x, y) |
|---|---|---|---|---|---|---|
| Example 1 | compound 1 | 5.8 | 0.31 | 107 | 45.3 | (0.30, 0.60) |
| Example 2 | compound 10 | 5.6 | 0.33 | 105 | 52.2 | (0.32, 0.61) |
| Example 3 | compound 27 | 5.6 | 0.31 | 107 | 50.3 | (0.30, 0.60) |
| Example 4 | compound 58 | 5.0 | 0.31 | 107 | 38.3 | (0.30, 0.60) |
| Comparative Example 1 | CBP | 6.1 | 0.31 | 101 | 32.6 | (0.33, 0.61) |

From the results noted in Table 1, it can be seen that in an organic electro-luminescence device using the inventive material for the organic electro-luminescence device, it is possible to obtain long-life green light with a high efficiency, and an improved color purity. Thus, the inventive material as a green phosphorescence host material for an organic electro-luminescence device can significantly improve the luminous efficiency and life span.

It is natural that even though the inventive compounds are applied to other organic material layers of an organic electro-luminescence device, e.g., an electron injection layer, an electron transport layer, a hole injection layer and a hole transport layer as well as a light emitting layer, it is possible to achieve the same effects.

Although a preferred embodiment of the present invention has been described for illustrative purposes, those skilled in the art will appreciate that various modifications, additions and substitutions are possible, without departing from the scope and spirit of the invention as disclosed in the accompanying claims. Therefore, the embodiments disclosed in the present invention are intended to illustrate the scope of the technical idea of the present invention, and the scope of the present invention is not limited by the embodiment.

The scope of the present invention shall be construed on the basis of the accompanying claims in such a manner that all of the technical ideas included within the scope equivalent to the claims belong to the present invention.

What is claimed is:

1. A compound represented by Formula 1 below:

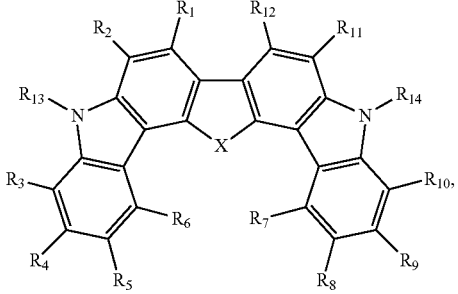

[Formula 1]

wherein

X is O, S, C($R_a$)($R_b$), N($R_c$), P($R_d$), Si($R_e$)($R_f$) or Ge($R_g$)($R_h$), wherein $R_a$, $R_b$, $R_c$, $R_d$, $R_e$, $R_f$, $R_g$ and $R_h$ are each independently selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, a $C_1$-$C_{30}$ alkoxy group, a $C_6$-$C_{30}$ aryloxy group, and -L-N(R')(R"), $R_1$ to $R_{14}$ are each independently selected from the group consisting of hydrogen, deuterium, halogen, a cyano group, a $C_6$-$C_{60}$ aryl group, a fluorenyl group, a fused ring group of a $C_3$-$C_{60}$ aliphatic ring and a $C_6$-$C_{60}$ aromatic ring, a $C_2$-$C_{60}$ heterocyclic group containing at least one heteroatom selected from the group consisting of O, N, S, Si and P, a $C_1$-$C_{50}$ alkyl group, a $C_2$-$C_{20}$ alkenyl group, a $C_1$-$C_{30}$ alkoxy group, a $C_6$-$C_{30}$ aryloxy group, and -L-N(R')(R"), wherein at least one of, but not all of, $R_1$ to $R_{14}$ is linked to an adjacent group to form a monocyclic or polycyclic ring, L is selected from the group consisting of a single bond; a $C_6$-$C_{60}$ arylene group; a fluorenyl group; a $C_2$-$C_{60}$ heterocyclic group containing at least one heteroatom selected from the group consisting of O, N, S, Si, and P; and a bivalent aliphatic hydrocarbon group, wherein the arylene group, the fluorenyl group, the heterocyclic group, and the bivalent aliphatic hydrocarbon group are optionally substituted by one or more substituents selected from the group consisting of a nitro group, a cyano group, a halogen group, a $C_1$-$C_{20}$ alkyl group, a $C_6$-$C_{20}$ aryl group, a $C_2$-$C_{20}$ heterocyclic group, a $C_1$-$C_{20}$ alkoxy group, and an amino group; and R' and R" are each independently a $C_2$-$C_{60}$ heterocyclic group containing at least one heteroatom selected from the group consisting of O, N, S, Si, and P, a $C_6$-$C_{20}$ aryl group, or a fluorenyl group;

with the proviso that when $R_1$ to $R_{14}$, $R_a$, $R_b$, $R_c$, $R_d$, $R_e$, $R_f$, $R_g$ and $R_h$ are an aryl group, a fluorenyl group, a fused ring group, a heterocyclic group, a alkyl group, a alkenyl group, a alkoxy group, or a aryloxy group, $R_1$ to $R_{14}$, $R_a$, $R_b$, $R_c$, $R_d$, $R_e$, $R_f$, $R_g$ and $R_h$ are optionally substituted by one or more substituents selected from the group consisting of deuterium, halogen, a silane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

2. The compound as claimed in claim 1, wherein at least one group of $R_1$ and $R_2$, $R_3$ and $R_4$, $R_4$ and $R_5$, $R_5$ and $R_6$, $R_7$ and $R_8$, $R_8$ and $R_9$, $R_9$ and $R_{10}$, and $R_{11}$ and $R_{12}$ forms a monocyclic or polycyclic ring.

3. The compound as claimed in claim 1, wherein at least one group of $R_2$ and $R_{13}$, $R_3$ and $R_{13}$, $R_{10}$ and $R_{14}$, and $R_{11}$ and $R_{14}$ forms a monocyclic or polycyclic ring.

4. A compound represented by Formula 2 below:

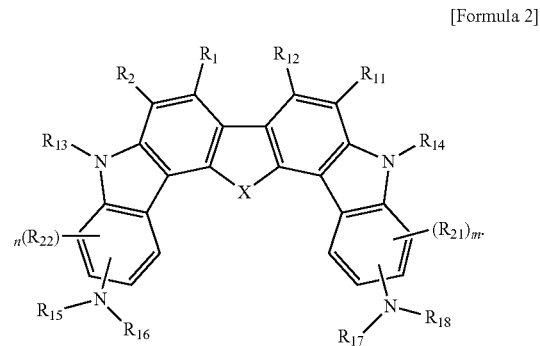

[Formula 2]

in Formula 2,

X is O, S, C($R_a$)($R_b$), N($R_c$), P($R_d$), Si($R_e$)($R_f$) or Ge($R_g$)($R_h$), wherein $R_a$, $R_b$, $R_c$, $R_d$, $R_e$, $R_f$, $R_g$ and $R_h$ are each independently selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, a $C_1$-$C_{30}$ alkoxy group, a $C_6$-$C_{30}$ aryloxy group, and -L-N(R')(R"), $R_1$, $R_2$, and $R_{11}$ to $R_{18}$ are each independently selected from the group consisting of hydrogen, deuterium, halogen, a cyano group, a $C_6$-$C_{60}$ aryl group, a fluorenyl group, a fused ring group of a $C_3$-$C_{60}$ aliphatic ring and a $C_6$-$C_{60}$ aromatic ring, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, a $C_1$-$C_{30}$ alkoxy group, a $C_6$-$C_{30}$ aryloxy group, and -L-N(R')(R"), $R_{21}$ and $R_{22}$ are each independently selected from the group consisting of deuterium, halogen, a cyano group, a $C_6$-$C_{60}$ aryl group, a fluorenyl group, a fused ring group of a $C_3$-$C_{60}$ aliphatic ring and a $C_6$-$C_{60}$ aromatic ring, a $C_2$-$C_{60}$ heterocyclic group containing at least one heteroatom selected from the group consisting of O, N, S, Si, and P, a $C_1$-$C_{50}$ alkyl group, a $C_2$-$C_{20}$ alkenyl group, a $C_1$-$C_{30}$ alkoxy group, a $C_6$-$C_{30}$ aryloxy group, and -L-N(R')(R"), m and n are each an integer of 0 to 3, wherein at least one of $R_1$, $R_2$, $R_{11}$ to $R_{14}$, $R_{21}$ and $R_{22}$, but not all of them, is optionally linked to an adjacent group to form a monocyclic or polycyclic ring, L is selected from the group consisting of a single bond; a $C_6$-$C_{60}$ arylene group; a fluorenyl group; a $C_2$-$C_{60}$ heterocyclic group containing at least one heteroatom selected from the group consisting of O, N, S, Si, and P; and a bivalent aliphatic hydrocarbon group, Wherein, the arylene group, the fluorenyl group, the heterocyclic group, and the bivalent aliphatic hydrocarbon group are optionally substituted by one or more substituents selected from the group consisting of a nitro group, a cyano group, a halogen group, a $C_1$-$C_{20}$ alkyl group, a $C_6$-$C_{20}$ aryl group, a $C_2$-$C_{20}$ heterocyclic group, a $C_1$-$C_{20}$ alkoxy group, and an amino group;

R' and R" are each independently a $C_2$-$C_{60}$ heterocyclic group containing at least one heteroatom selected from the group consisting of O, N, S, Si, and P, a $C_6$-$C_{20}$ aryl group, or a fluorenyl group;

with the proviso that when $R_1$, $R_2$, and $R_{11}$ to $R_{18}$ are an aryl group, a fluorenyl group, a fused ring group, a heterocyclic group, a alkyl group, a alkenyl group, a alkoxy group, or a aryloxy group, $R_1$ to $R_{14}$, $R_a$, $R_b$, $R_c$, $R_d$, $R_e$, $R_f$, $R_g$ and $R_h$ are optionally substituted by one or more substituents selected from the group consisting of deuterium, halogen, a silane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a $C_2$-$C_{20}$ heterocyclic group, a $C_3$-$C_{20}$ cycloalkyl group, a $C_7$-$C_{20}$ arylalkyl group, and a $C_8$-$C_{20}$ arylalkenyl group.

5. The compound as claimed in claim 4, at least one group of $R_1$ and $R_2$, $R_{11}$ and $R_{12}$, two adjacent $R_{21}$, and two adjacent $R_{22}$ forms a monocyclic or polycyclic ring.

6. The compound as claimed in claim 4, wherein at least one group of $R_2$ and $R_{13}$, and $R_{11}$ and $R_{14}$ are linked together to form a monocyclic or polycyclic ring.

7. A compound selected from the group consisting of Compounds 1 to 96:

Compound 1

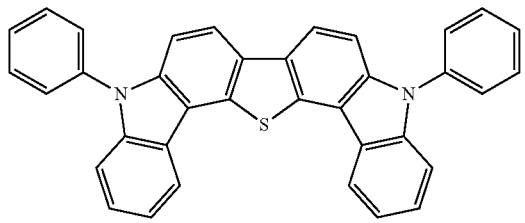

Compound 2

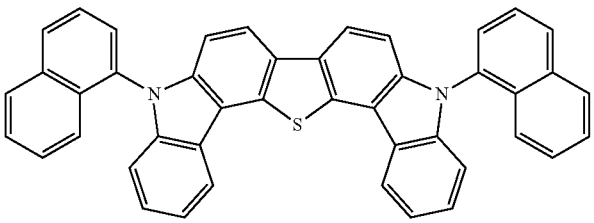

Compound 3

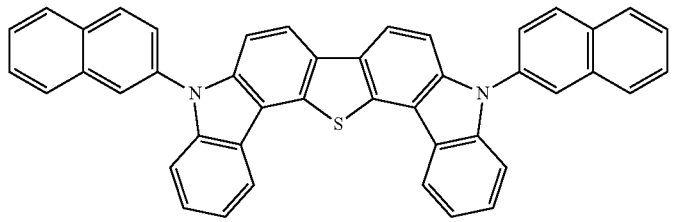

Compound 4

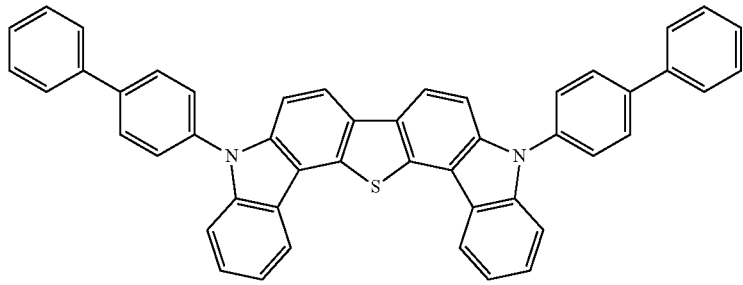

Compound 5

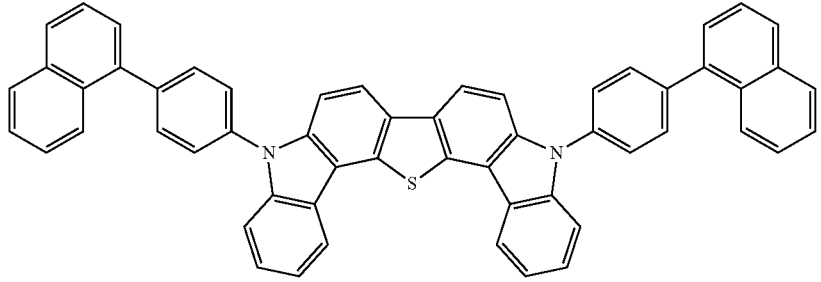

Compound 6
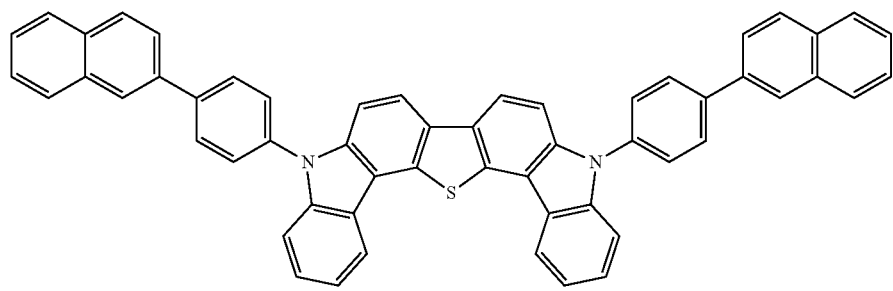
Compound 7
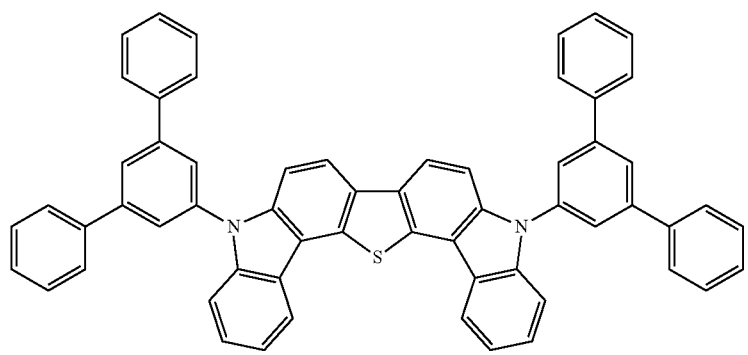
Compound 8
Compound 9
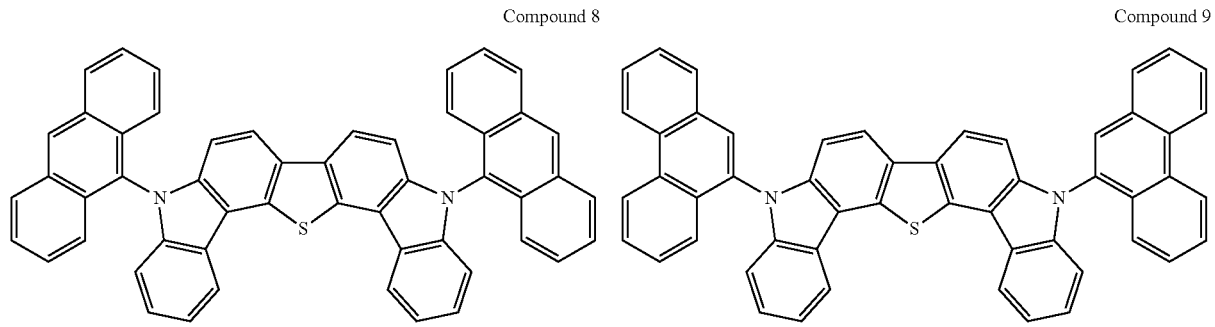
Compound 10
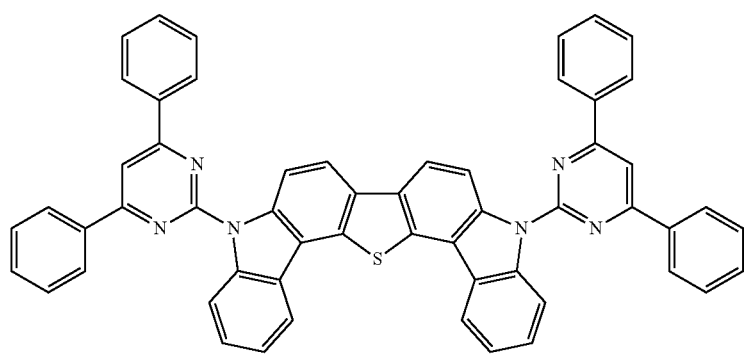

Compound 11
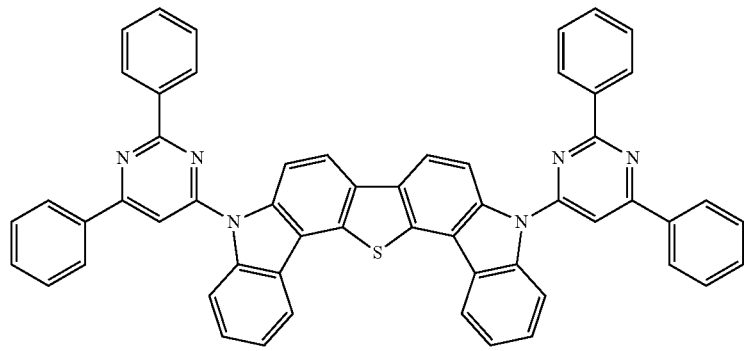
Compound 12
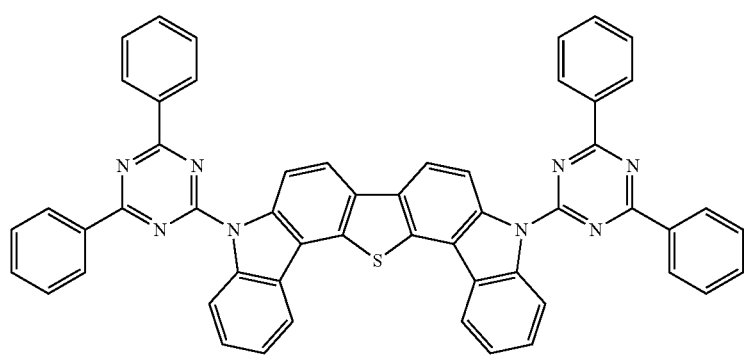
Compound 13
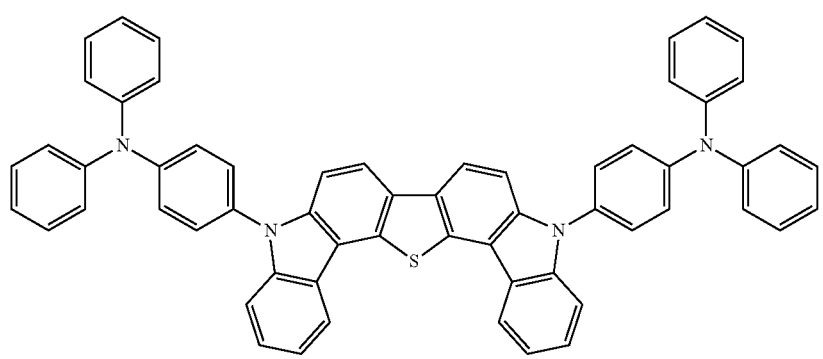
Compound 14
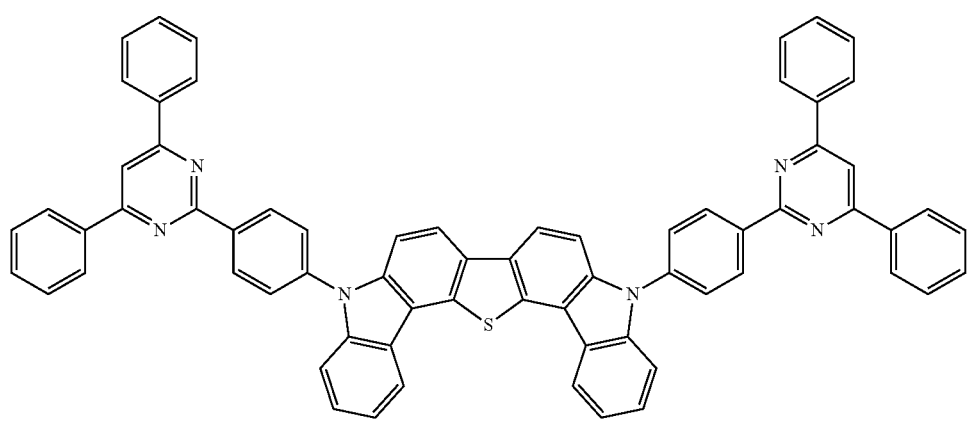

Compound 15
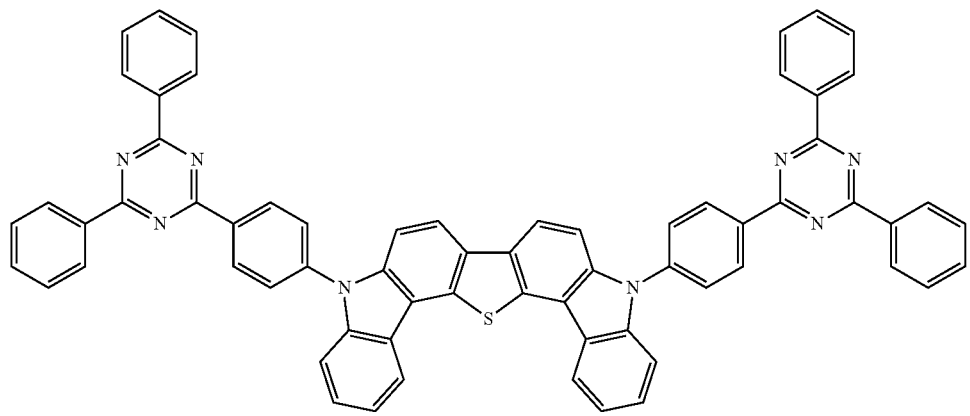
Compound 16
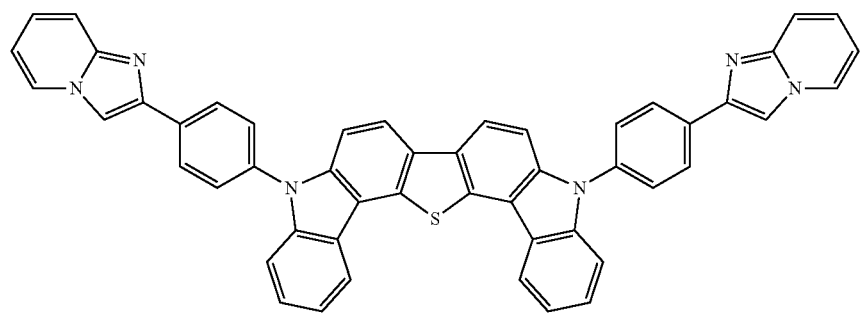
Compound 17
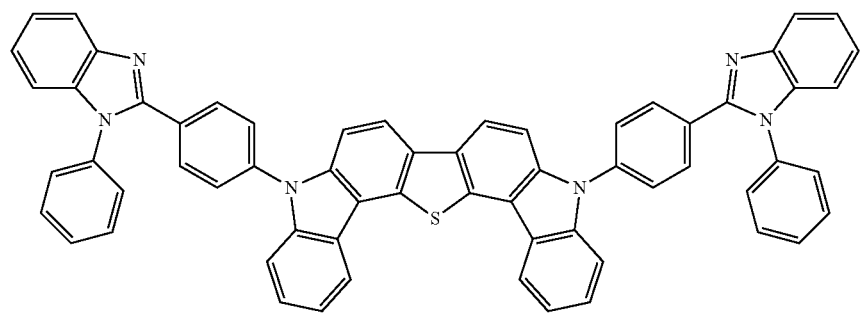
Compound 18
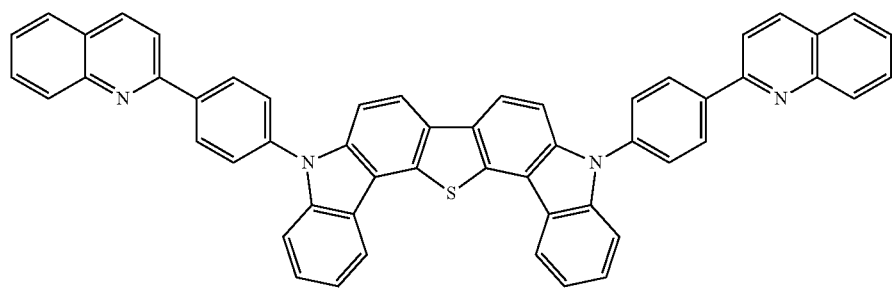

-continued
Compound 19
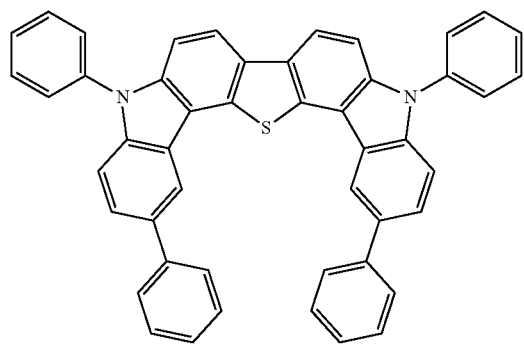
Compound 20
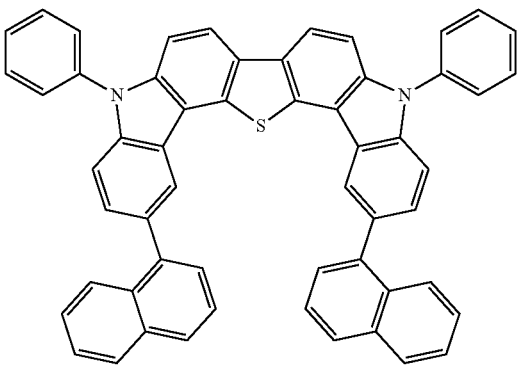
Compound 21
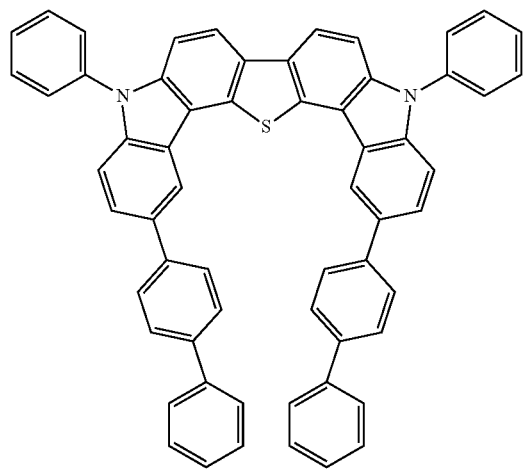
Compound 22
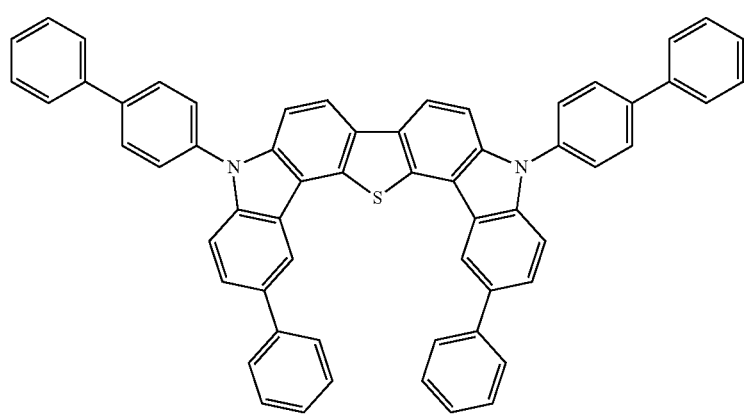

-continued
Compound 23
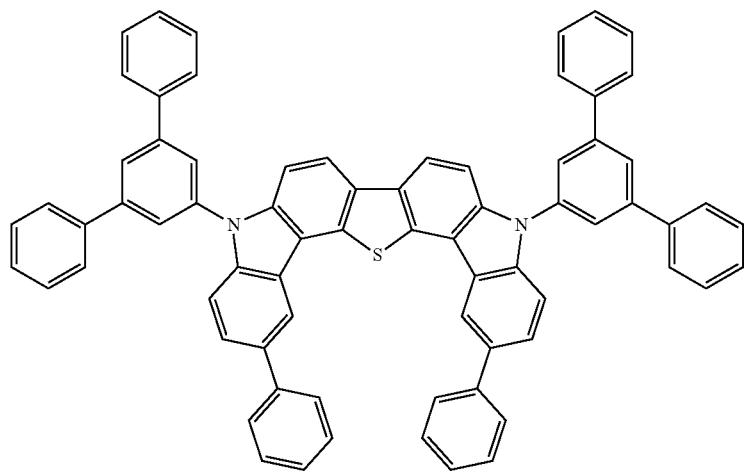
Compound 24
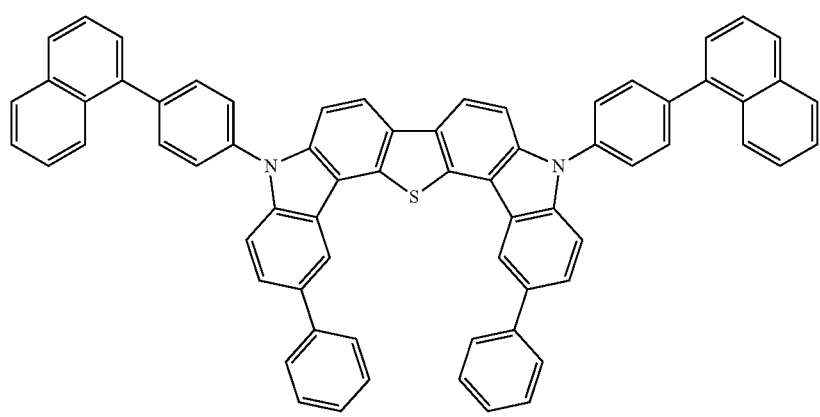
Compound 25
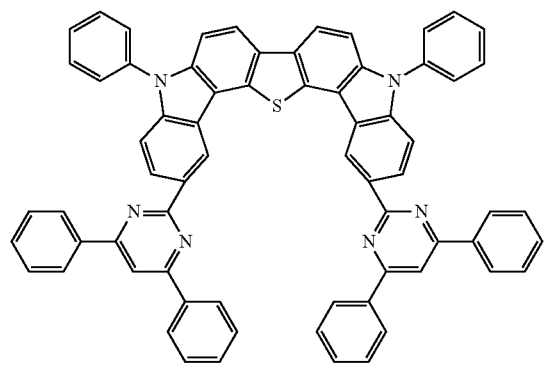
Compound 26
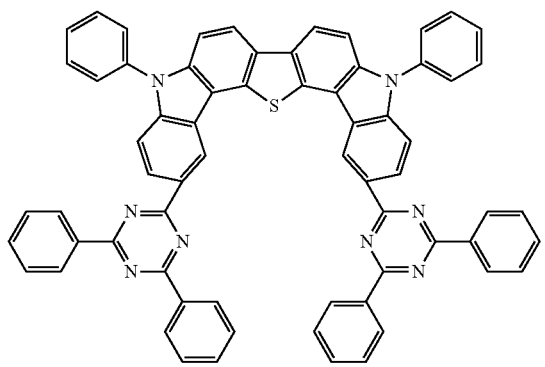

-continued
Compound 27
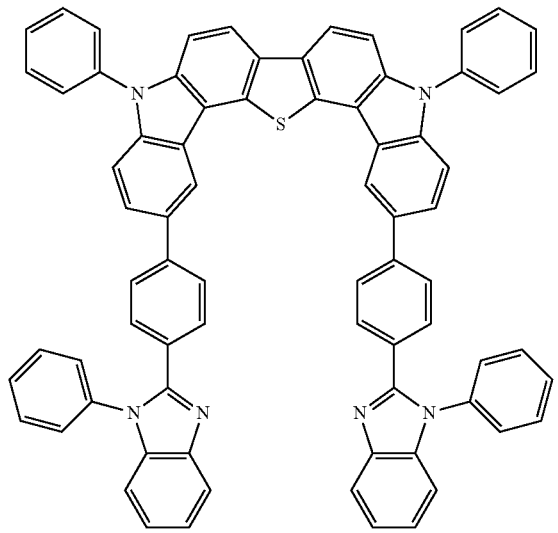
Compound 28
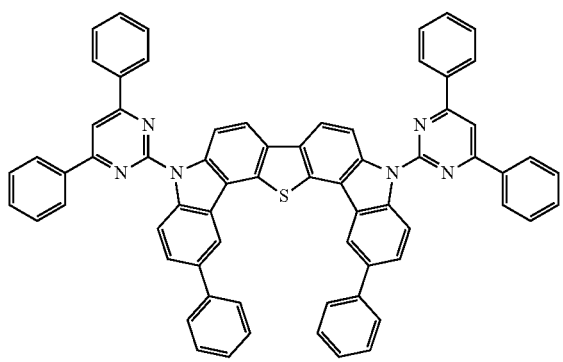
Compound 29
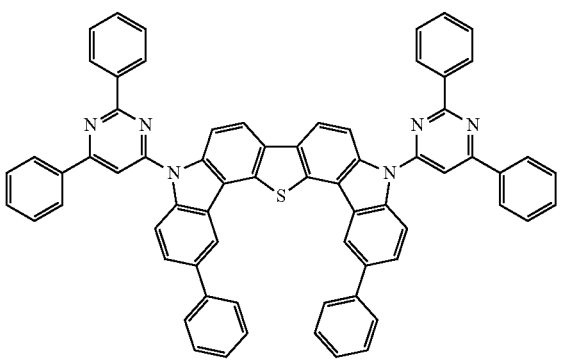
Compound 30
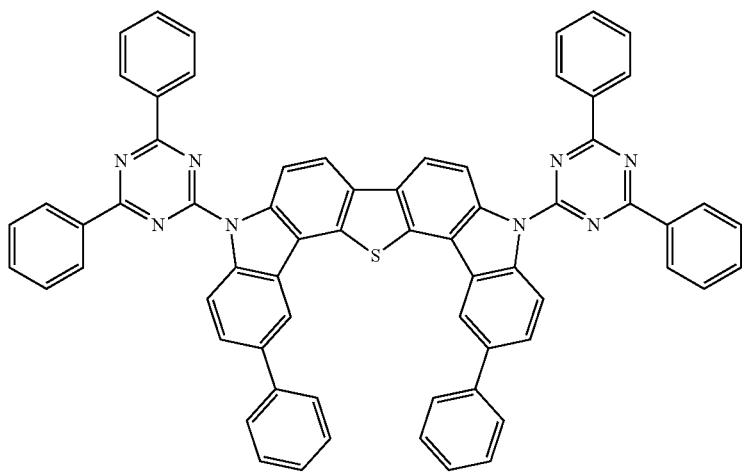

-continued
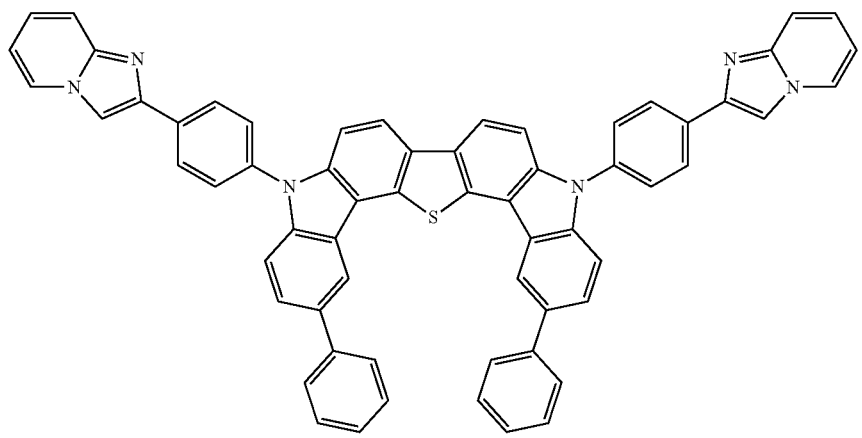
Compound 31
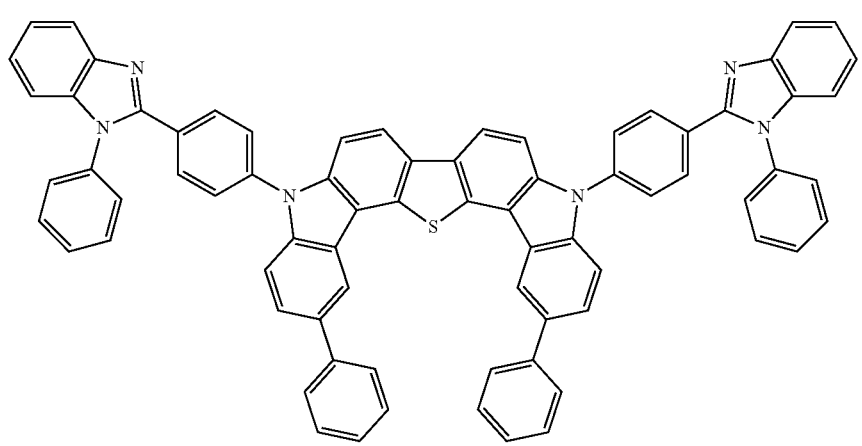
Compound 32
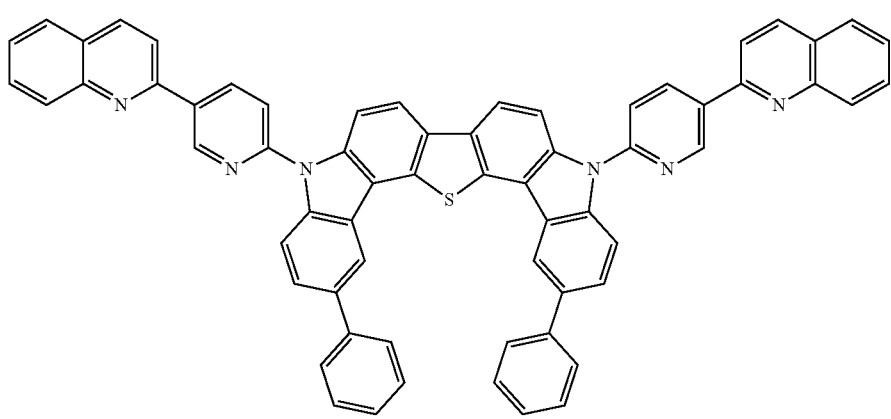
Compound 33

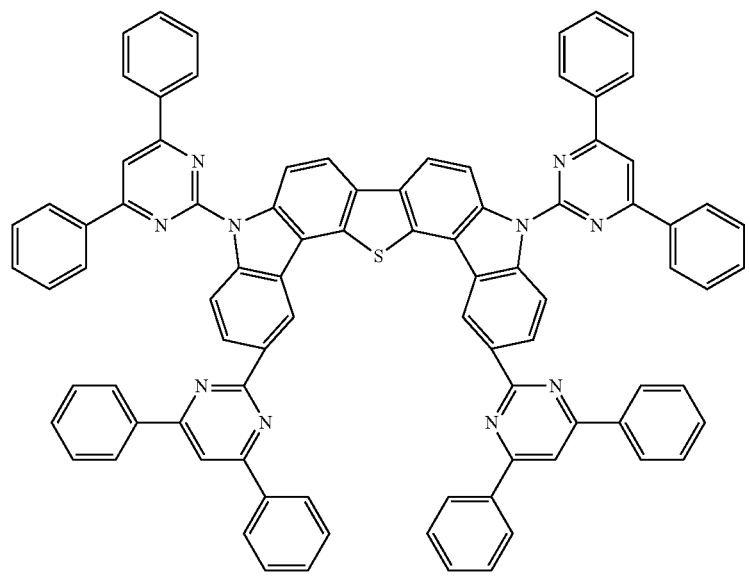
Compound 34
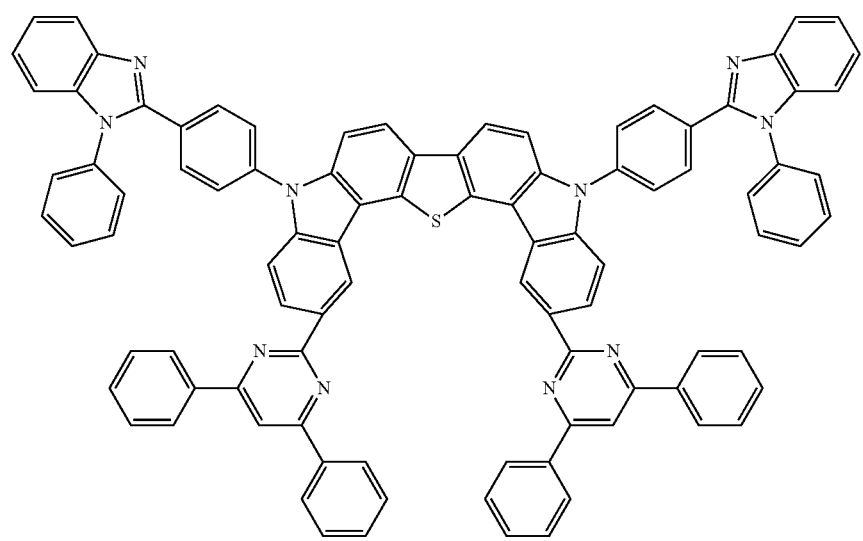
Compound 35

-continued
Compound 36
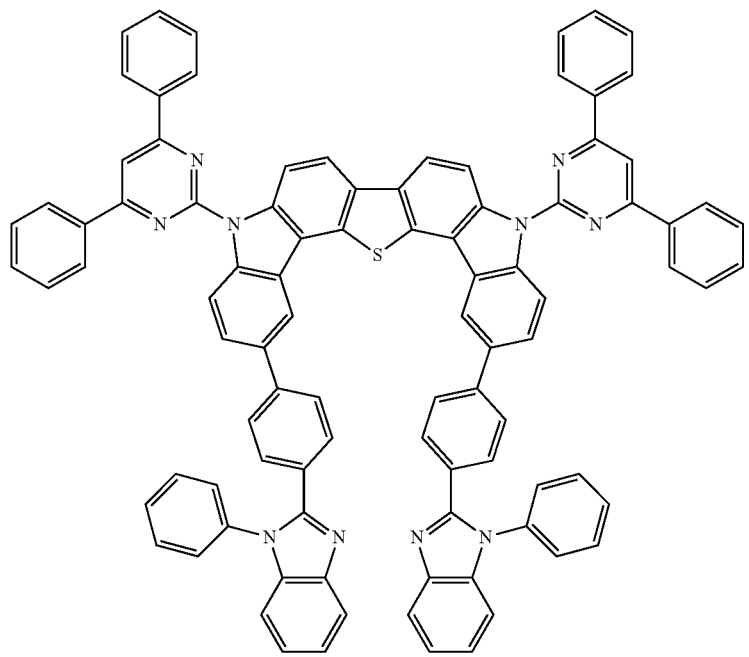
Compound 37
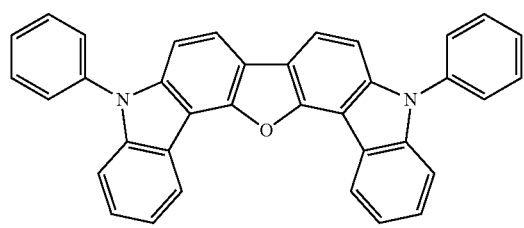
Compound 38
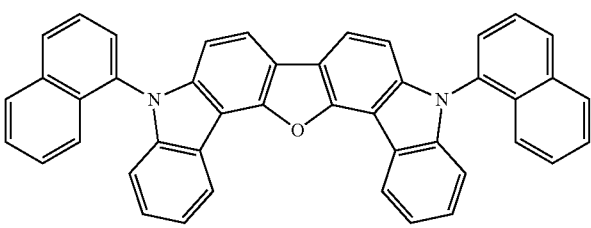
Compound 39
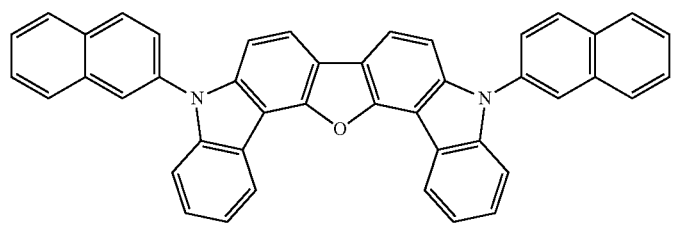
Compound 40
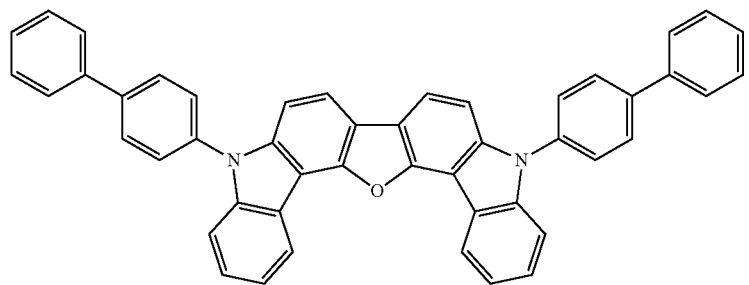

-continued
Compound 41
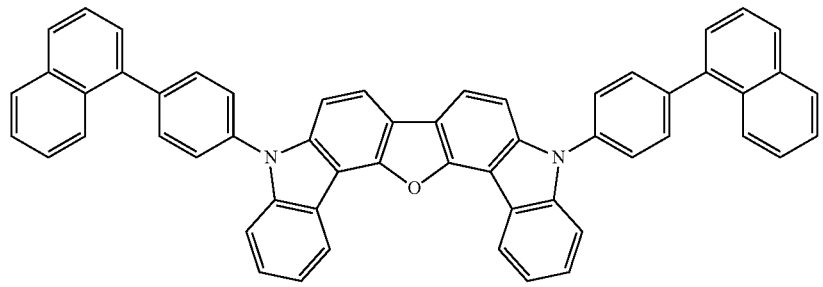
Compound 42
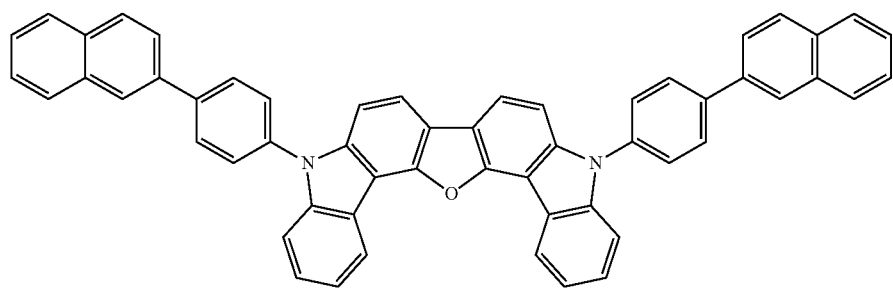
Compound 43
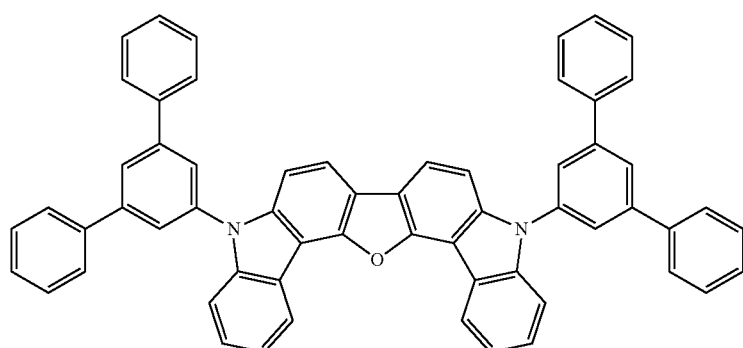
Compound 44 Compound 45
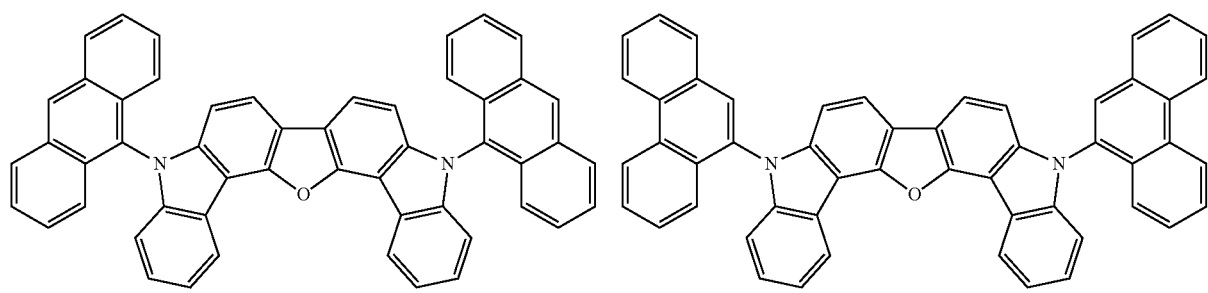
Compound 46 Compound 47
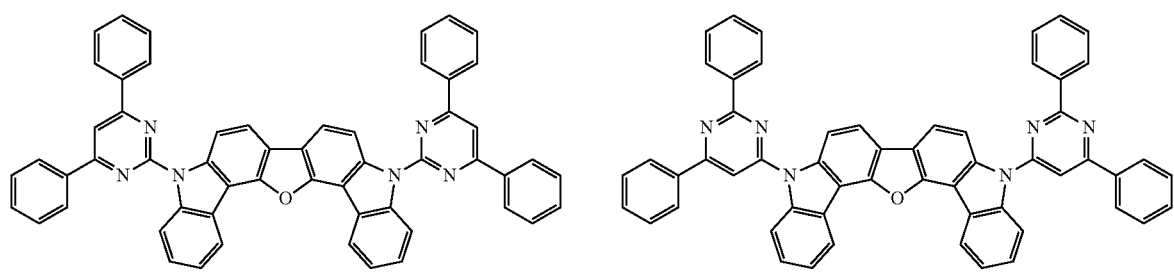

Compound 48
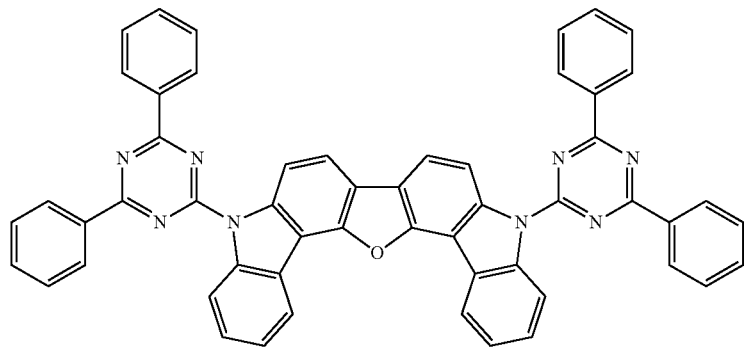
Compound 49
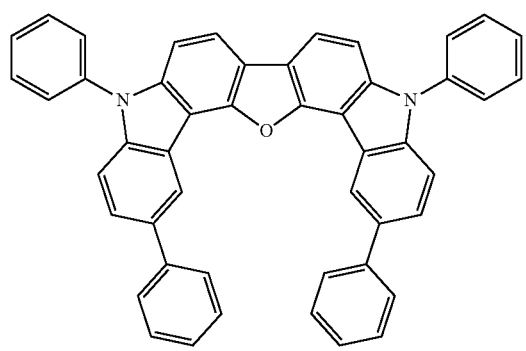
Compound 50
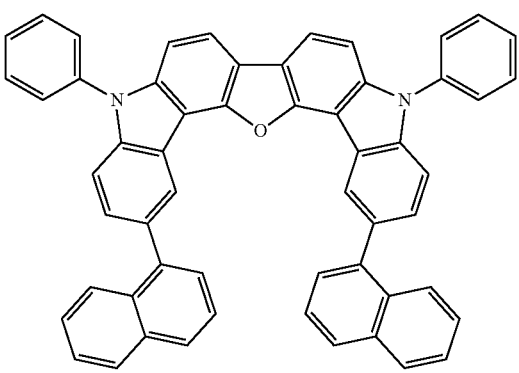
Compound 51
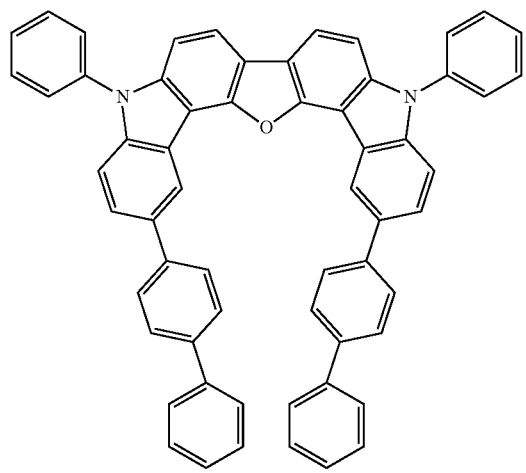
Compound 52
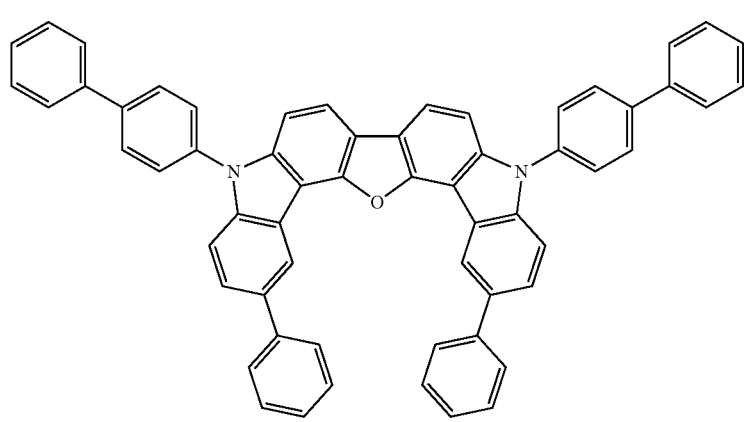

-continued
Compound 53
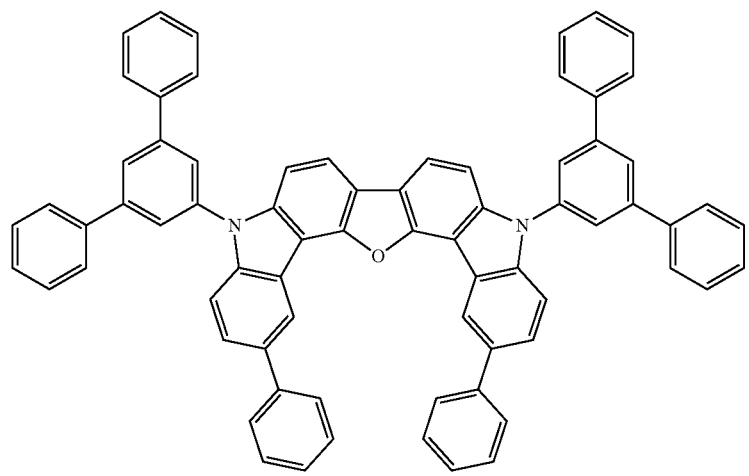
Compound 54
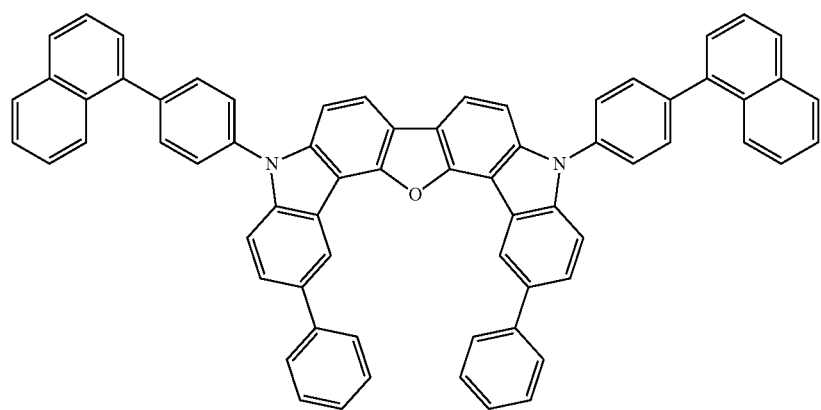
Compound 55
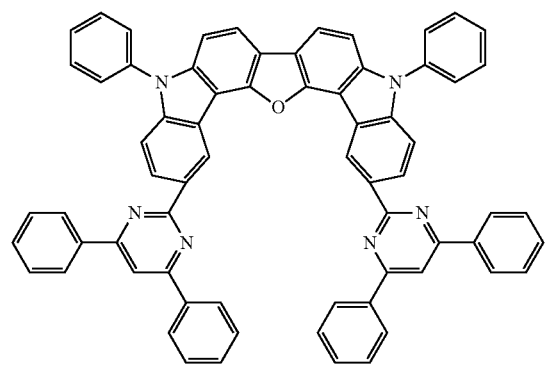
Compound 56
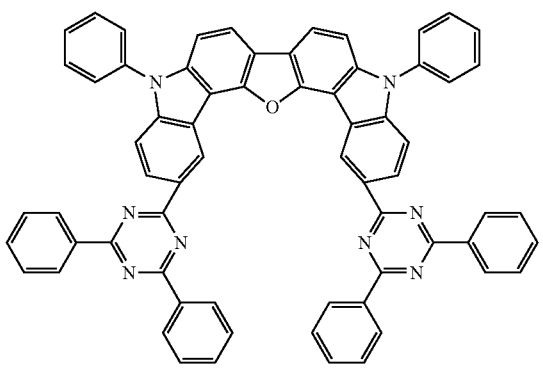

-continued
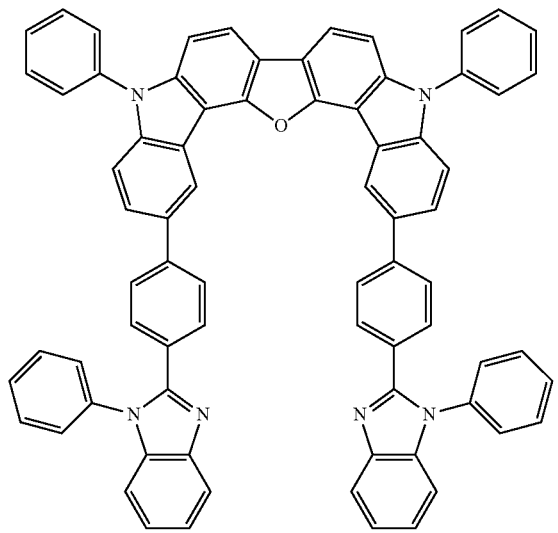
Compound 57
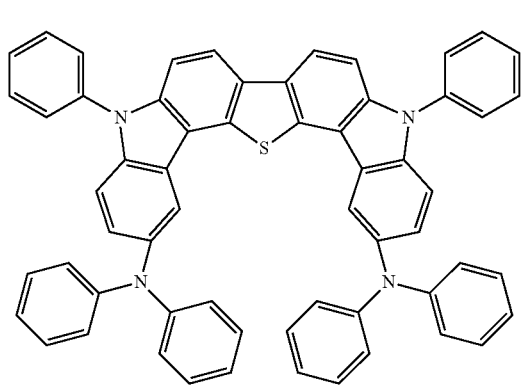
Compound 58
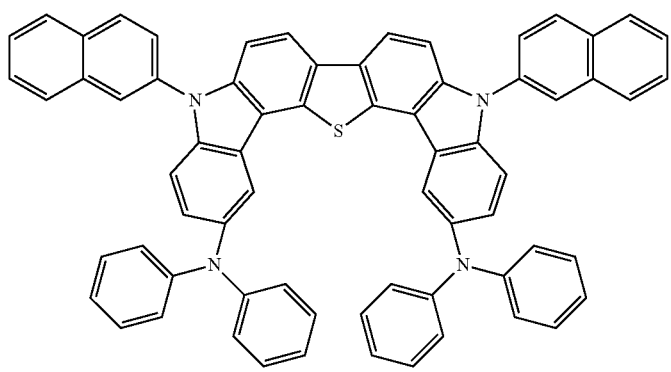
Compound 59

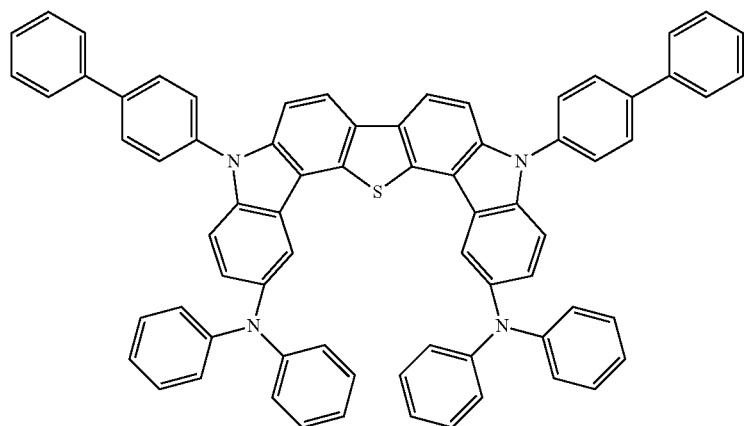
Compound 60
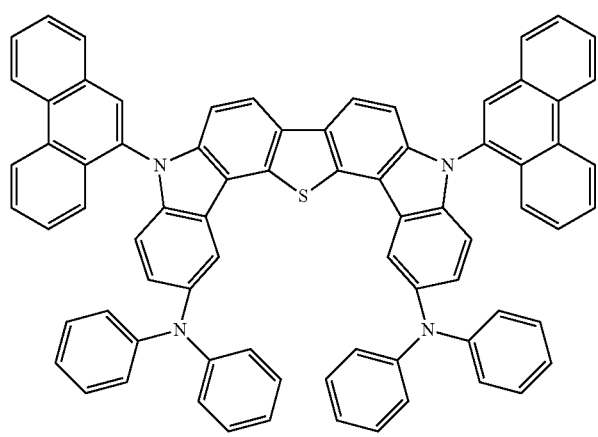
Compound 61
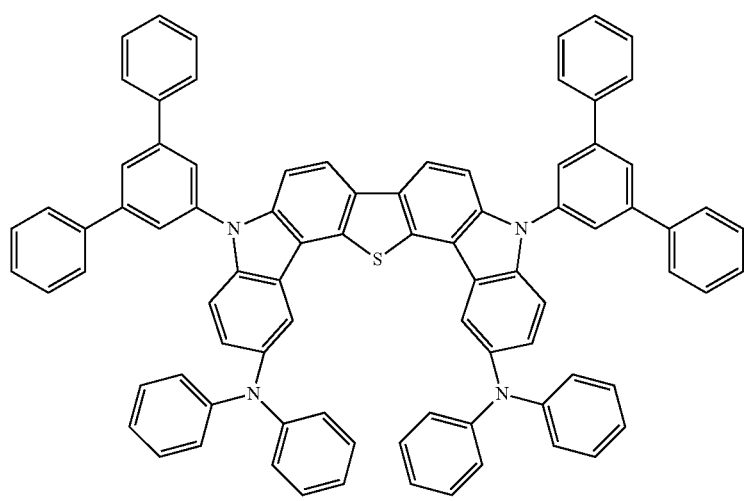
Compound 62

-continued
Compound 63
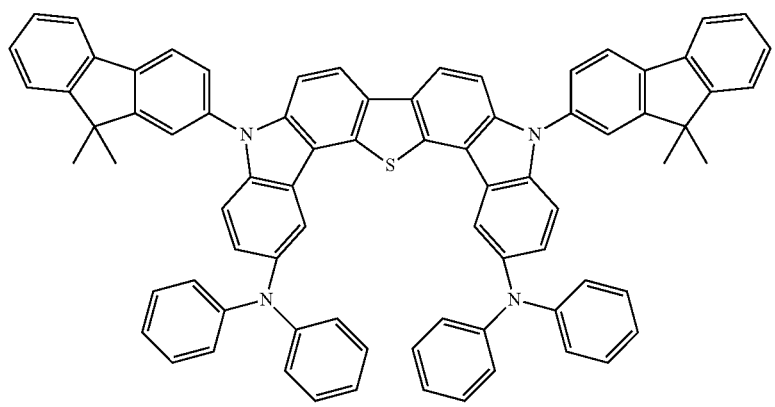
Compound 64
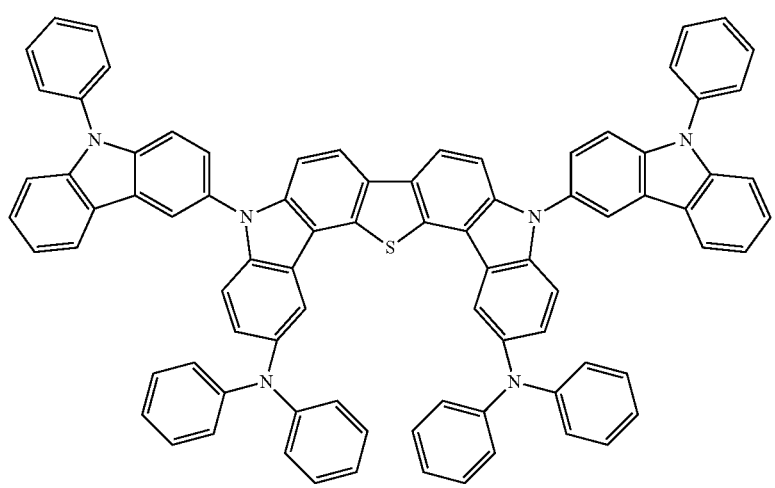
Compound 65
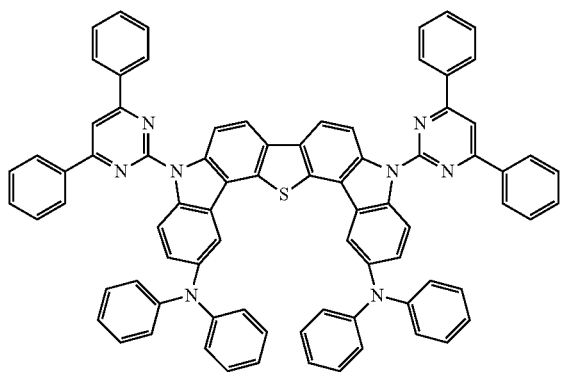
Compound 66
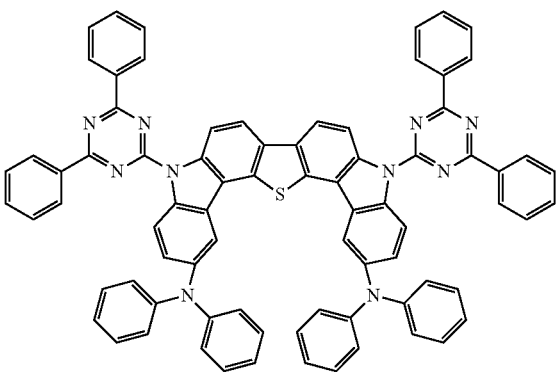
Compound 67
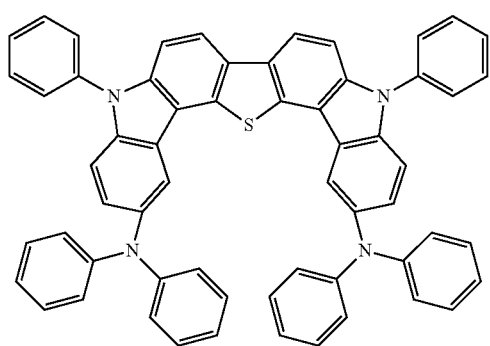
Compound 68
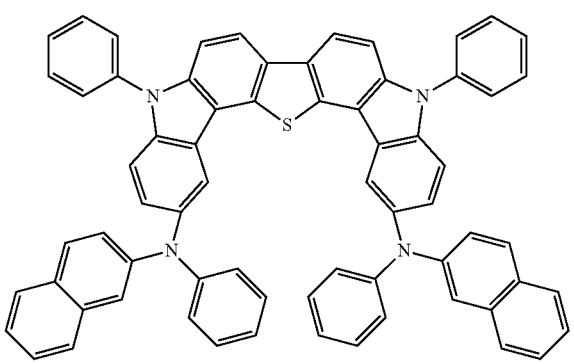

-continued
Compound 69
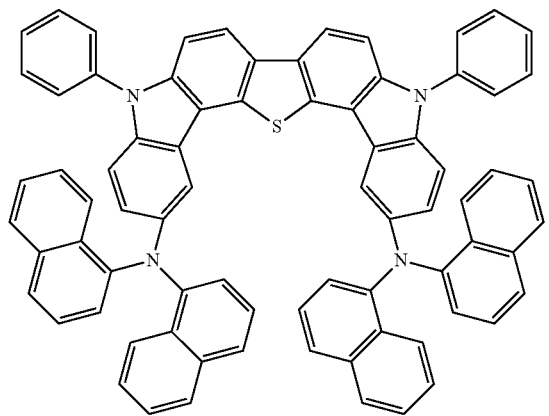
Compound 70
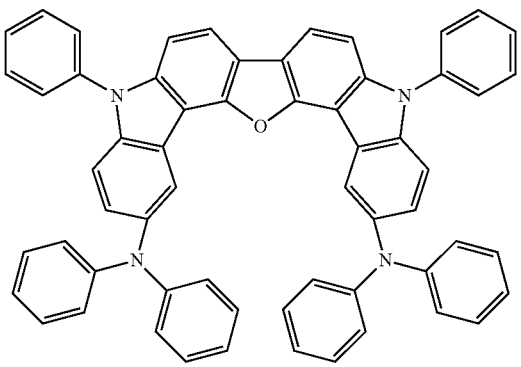
Compound 71
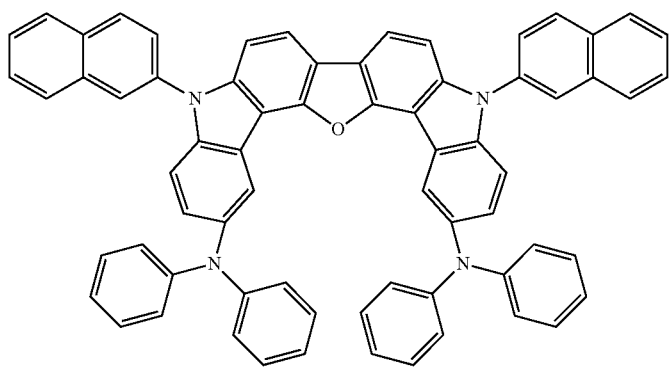
Compound 72
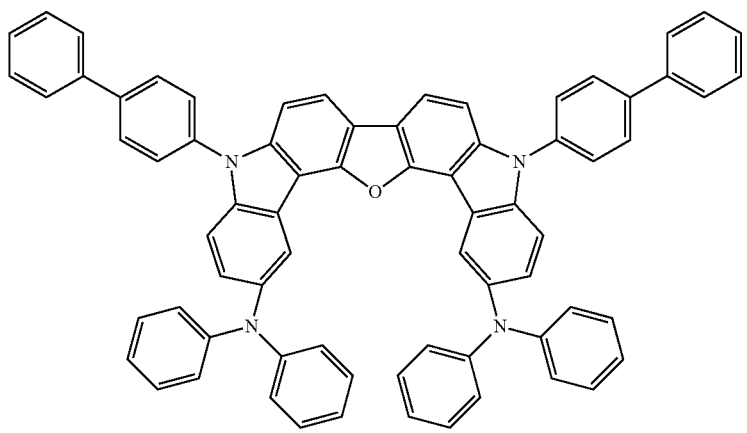

Compound 73
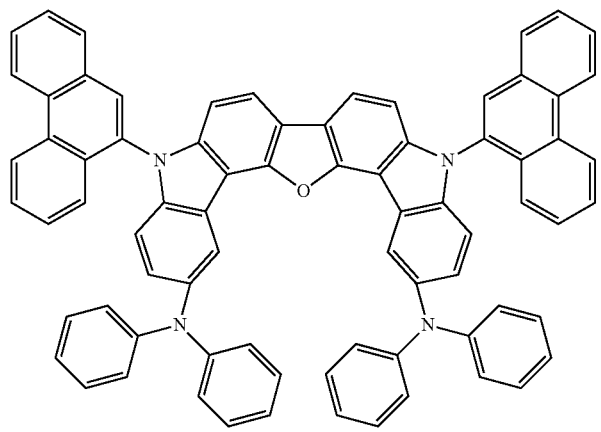
Compound 74
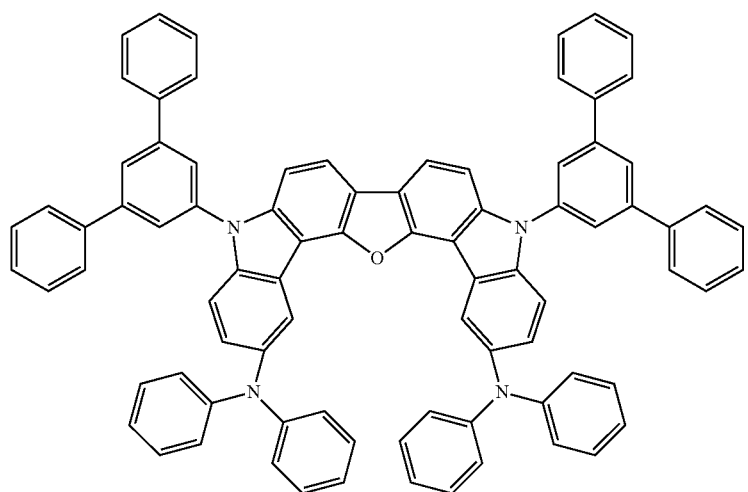
Compound 75
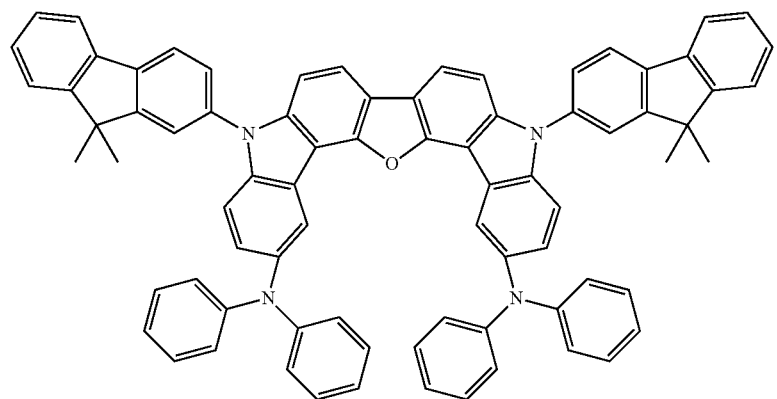

-continued
Compound 76
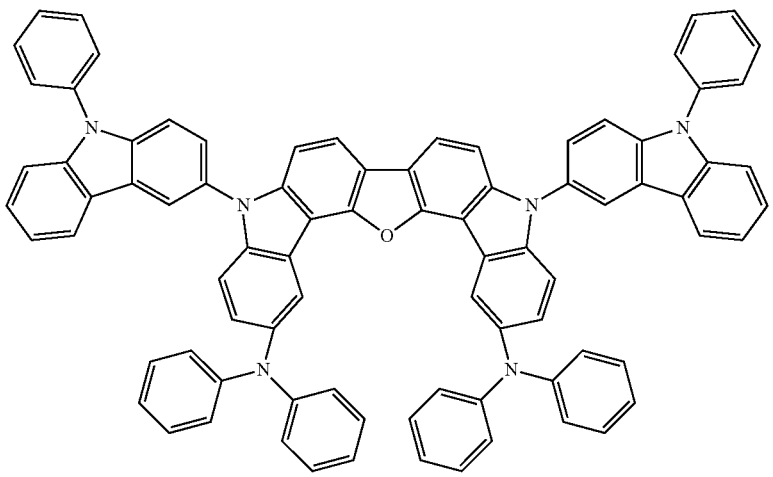
Compound 77
Compound 78
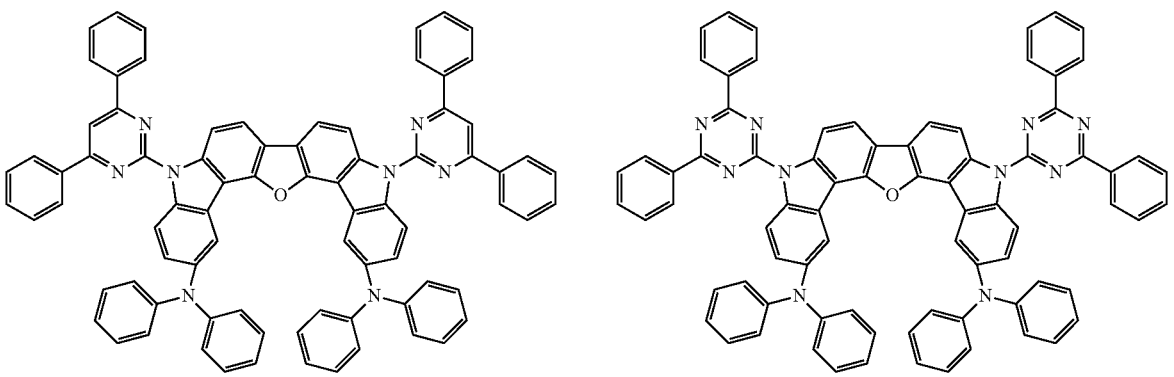
Compound 79
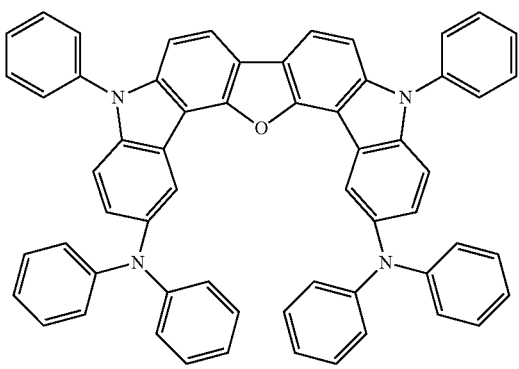
Compound 80
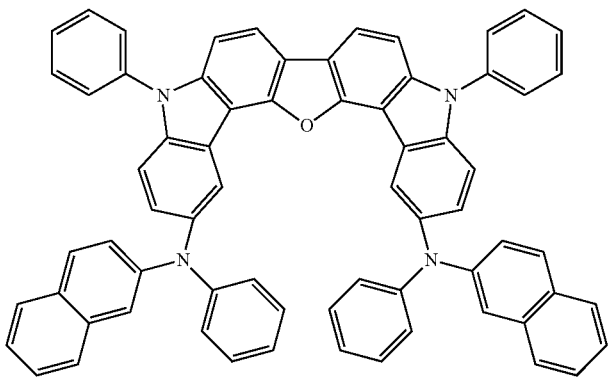

-continued
Compound 81
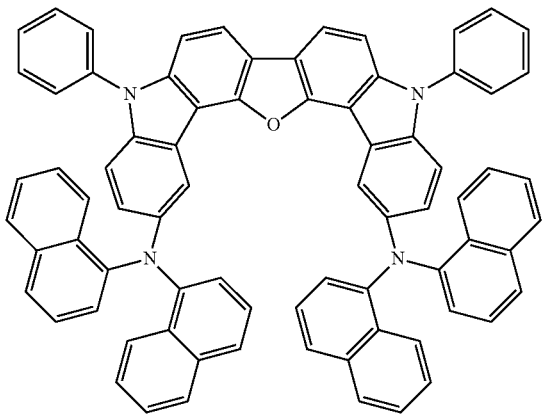
Compound 82
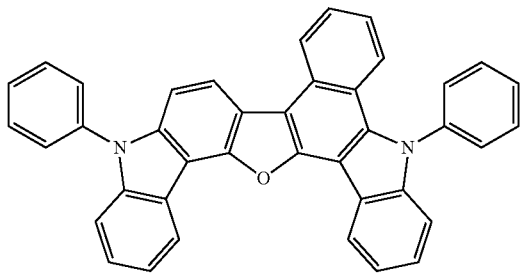
Compound 83
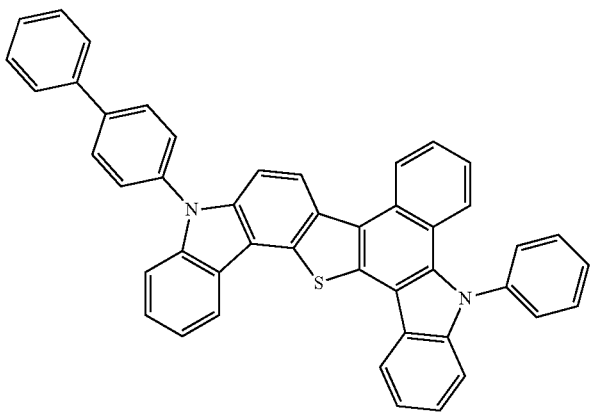
Compound 84
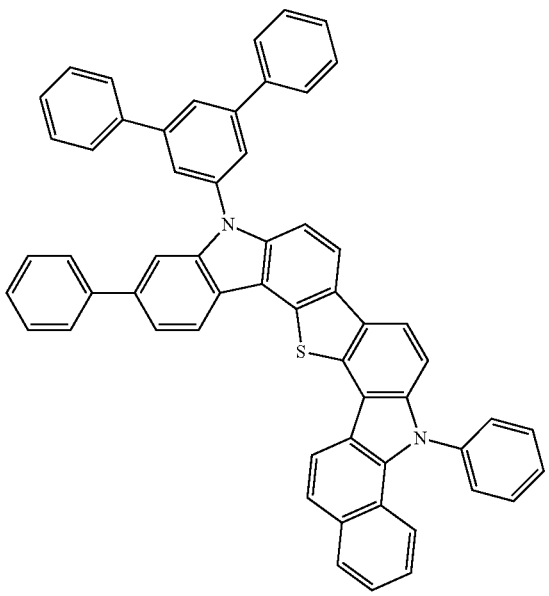
Compound 85
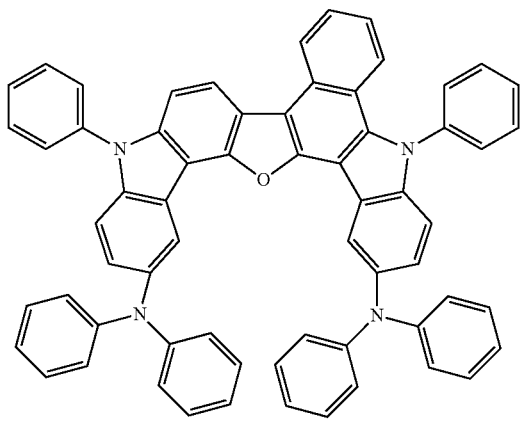

-continued
COMPOUND 86
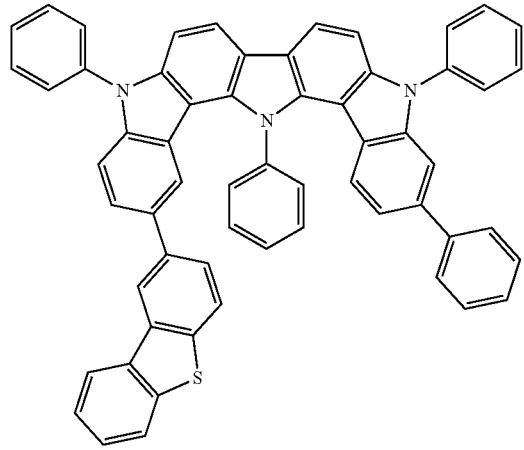
COMPOUND 87
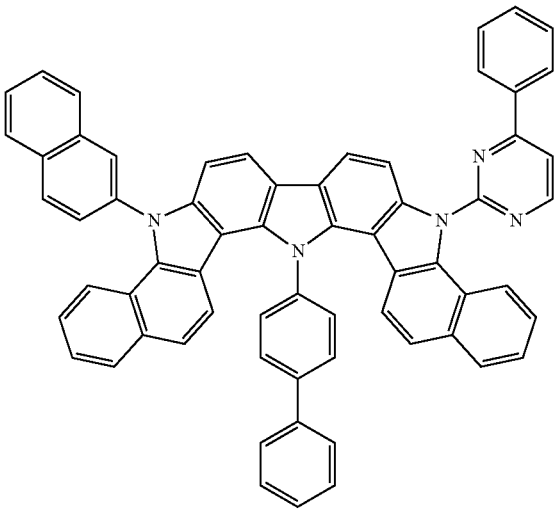
COMPOUND 88
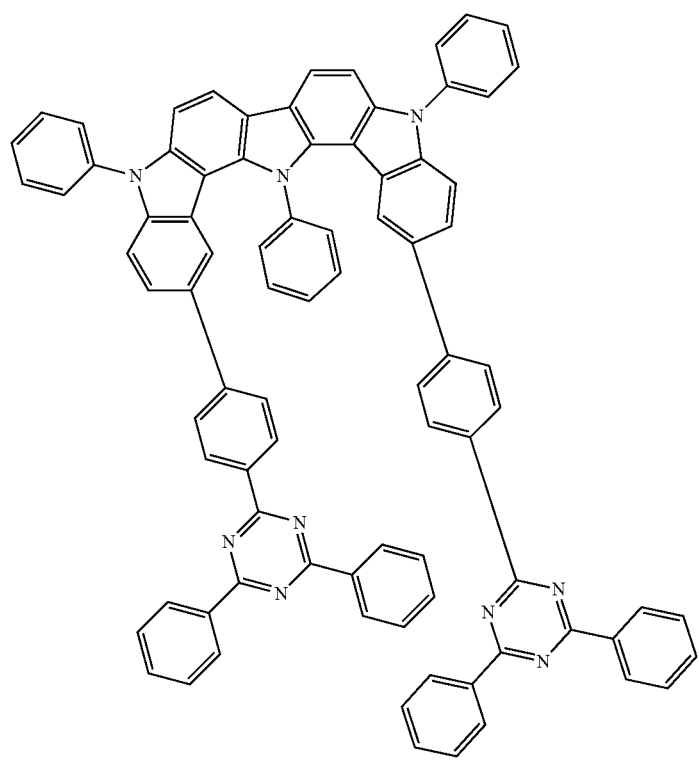
COMPOUND 89
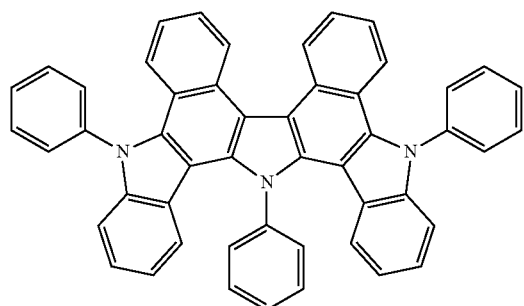

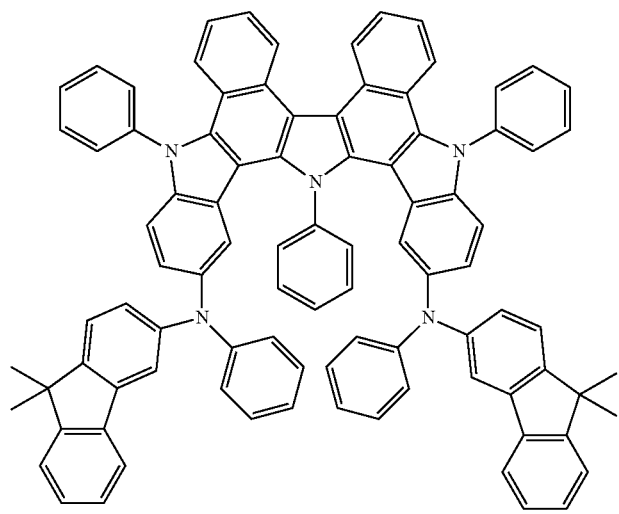
COMPOUND 90
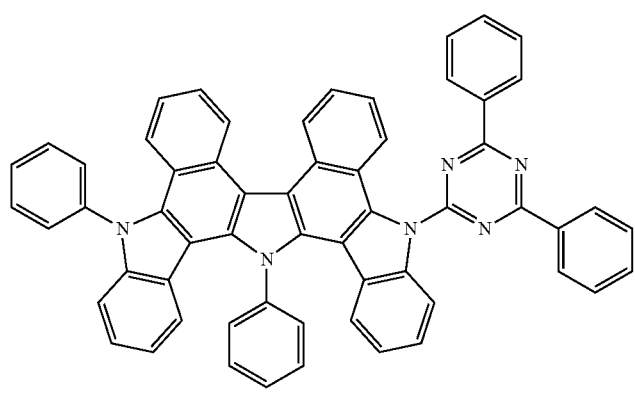
COMPOUND 91
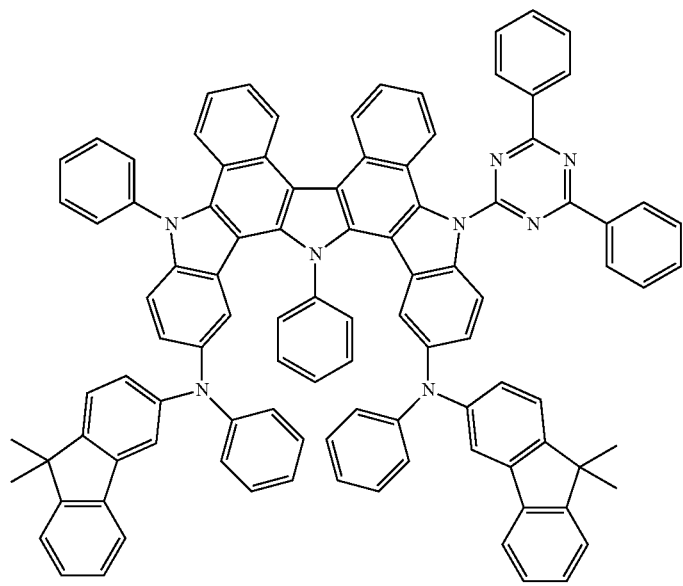
COMPOUND 92

COMPOUND 93
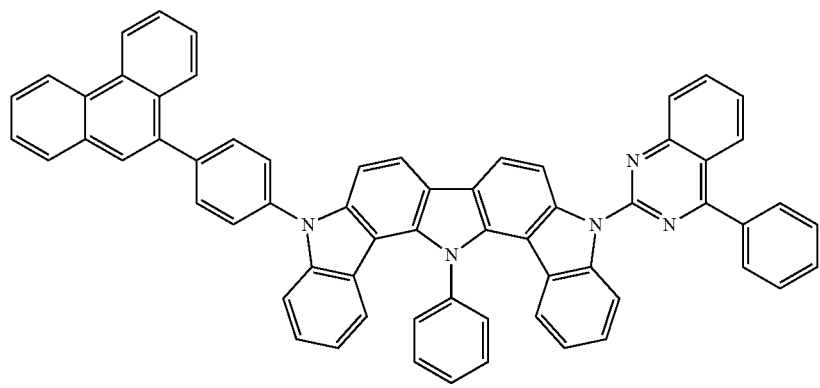
COMPOUND 94
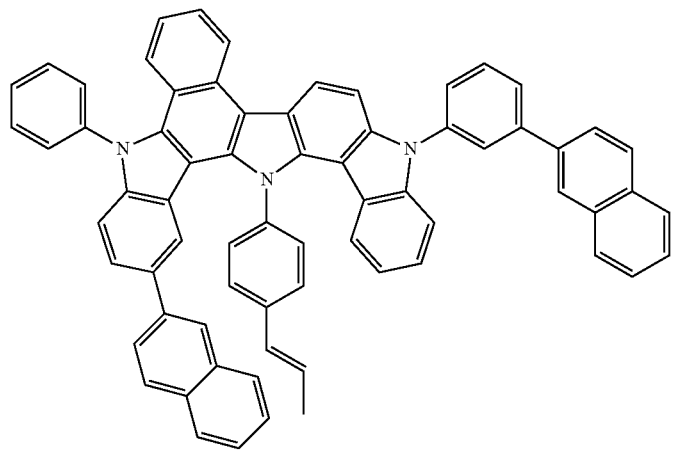
COMPOUND 95
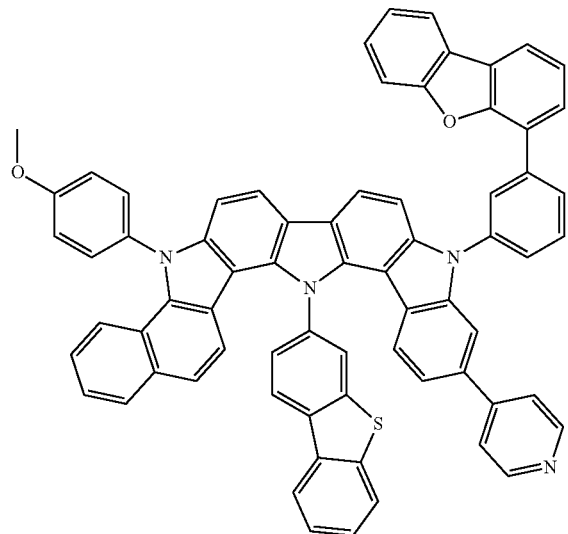

COMPOUND 96

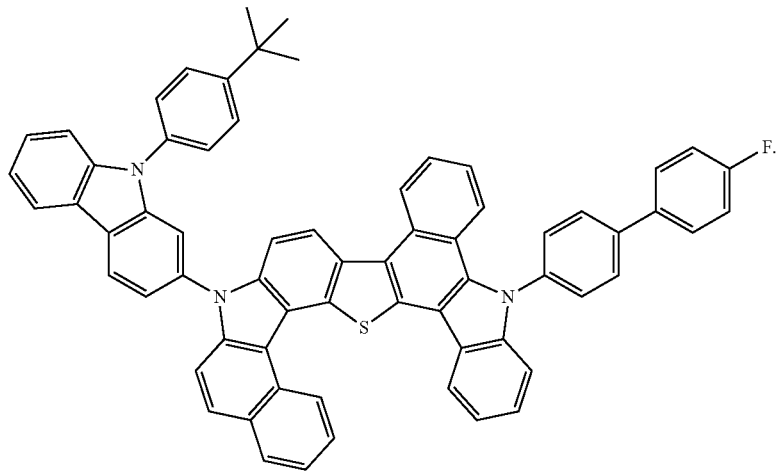

8. An organic electronic device comprising one or more organic material layers comprising the compound as claimed in claim 1.

9. An organic electronic device comprising one or more organic material layers comprising the compound as claimed in claim 4.

10. An organic electronic device comprising one or more organic material layers comprising the compound as claimed in claim 7.

11. The organic electronic device as claimed in claim 8, wherein the organic material layers comprise a light emitting layer comprising the compound.

12. The organic electronic device as claimed in claim 9, wherein the organic material layers comprise a light emitting layer comprising the compound.

13. The organic electronic device as claimed in claim 10, wherein the organic material layers comprise a light emitting layer comprising the compound.

14. The organic electronic device as claimed in claim 12, wherein the compound is used as a host material of the light emitting layer.

15. A terminal comprising a display device and a control part for driving the display device, the display device comprising the organic electronic device as claimed in claim 7.

16. A terminal comprising a display device and a control part for driving the display device, the display device comprising the organic electronic device as claimed in claim 8.

17. A terminal comprising a display device and a control part for driving the display device, the display device comprising the organic electronic device as claimed in claim 9.

18. The terminal as claimed in claim 15, wherein the organic electronic device is any one of an organic light-emitting diode, an organic solar cell, an organic photo conductor drum, an organic transistor, a photodiode, an organic laser, and a laser diode.

19. The terminal as claimed in claim 16, wherein the organic electronic device is any one of an organic light-emitting diode, an organic solar cell, an organic photo conductor drum, an organic transistor, a photodiode, an organic laser, and a laser diode.

20. The terminal as claimed in claim 17, wherein the organic electronic device is any one of an organic light-emitting diode, an organic solar cell, an organic photo conductor drum, an organic transistor, a photodiode, an organic laser, and a laser diode.

* * * * *